US012336955B2

(12) United States Patent
AlGhazi et al.

(10) Patent No.: US 12,336,955 B2
(45) Date of Patent: Jun. 24, 2025

(54) MOBILITY ASSISTANCE APPARATUS

(71) Applicants: CAN MOBILITIES, INC., Menlo Park, CA (US); Ahmad AlGhazi, Palo Alto, CA (US); Abdullah Hejazi, Fremont, CA (US)

(72) Inventors: Ahmad AlGhazi, Palo Alto, CA (US); Abdullah Hejazi, Fremont, CA (US)

(73) Assignee: CAN Mobilities, Inc., Menlo Park, CA (US)

( * ) Notice: Subject to any disclaimer, the term of this patent is extended or adjusted under 35 U.S.C. 154(b) by 688 days.

(21) Appl. No.: 17/612,175

(22) PCT Filed: May 18, 2020

(86) PCT No.: PCT/US2020/033459
§ 371 (c)(1),
(2) Date: Nov. 17, 2021

(87) PCT Pub. No.: WO2020/236747
PCT Pub. Date: Nov. 26, 2020

(65) Prior Publication Data
US 2022/0211568 A1 Jul. 7, 2022

Related U.S. Application Data

(60) Provisional application No. 62/849,337, filed on May 17, 2019.

(51) Int. Cl.
*A61H 3/04* (2006.01)
*A61H 3/02* (2006.01)

(52) U.S. Cl.
CPC ....... *A61H 3/04* (2013.01); *A61H 2003/0227* (2013.01); *A61H 2003/0233* (2013.01);
(Continued)

(58) Field of Classification Search
CPC .... A61H 3/04; A61H 3/02; A61H 2003/0227; A61H 2003/0233; A61H 2201/0161; A61H 2201/0184; A61H 2201/5043
See application file for complete search history.

(56) References Cited

U.S. PATENT DOCUMENTS 8,974,232 B2 * 3/2015 Behrenbruch ........... A45B 3/00
135/65
10,136,841 B2 * 11/2018 Alghazi ................... A61B 5/11
(Continued)

FOREIGN PATENT DOCUMENTS

| DE | 10318929 B3 | 8/2004 |
| EP | 2777677 A1 | 9/2014 |
| JP | 2009247411 A | 10/2009 |
| KR | 101278579 B1 | 6/2013 |
| KR | 101592321 B1 | 2/2016 |
| WO | 2017094018 A2 | 6/2017 |

OTHER PUBLICATIONS

EESR dated May 8, 2023 for EP Application No. 20808727.0.
International Search Report and Written Opinion for Application No. PCT/US2020/033459, dated Oct. 20, 2020.

*Primary Examiner* — Kevin Hurley
*Assistant Examiner* — Michael R Stabley
(74) *Attorney, Agent, or Firm* — Dorsey & Whitney LLP

(57) ABSTRACT

The application describes example of enhanced capability (also referred to as smart) mobility aid devices, such as rollators, wheel-chairs, walkers, crutches, canes and the like, as well as apparatuses, systems, and processes for enhancing the capabilities of mobility aid devices.

22 Claims, 29 Drawing Sheets

(52) U.S. Cl.
CPC ............... *A61H 2201/0103* (2013.01); *A61H 2201/0161* (2013.01); *A61H 2201/0176* (2013.01); *A61H 2201/0184* (2013.01); *A61H 2201/0188* (2013.01); *A61H 2201/0196* (2013.01); *A61H 2201/1253* (2013.01); *A61H 2201/1633* (2013.01); *A61H 2201/1635* (2013.01); *A61H 2201/5028* (2013.01); *A61H 2201/503* (2013.01); *A61H 2201/5043* (2013.01); *A61H 2201/5048* (2013.01); *A61H 2201/5061* (2013.01); *A61H 2201/5071* (2013.01); *A61H 2201/5092* (2013.01); *A61H 2203/0406* (2013.01); *A61H 2203/0431* (2013.01); *A61H 2230/08* (2013.01); *A61H 2230/30* (2013.01)

(56) References Cited

U.S. PATENT DOCUMENTS

| | | | |
|---|---|---|---|
| 10,267,648 B2 * | 4/2019 | Turitz | ............... A61G 5/10 |
| 2001/0028301 A1 | 10/2001 | Geiger et al. | |
| 2005/0076940 A1 | 4/2005 | Larson et al. | |
| 2006/0124366 A1 | 6/2006 | Le | |
| 2012/0029696 A1 | 2/2012 | Ota et al. | |
| 2012/0256384 A1 | 10/2012 | Schaaper et al. | |
| 2013/0231595 A1 | 9/2013 | Zoss et al. | |
| 2016/0095397 A1 | 4/2016 | Crowhurst | |
| 2017/0172462 A1 | 6/2017 | Alghazi | |
| 2017/0227376 A1 | 8/2017 | Turitz | |
| 2018/0168908 A1 | 6/2018 | Han et al. | |

* cited by examiner

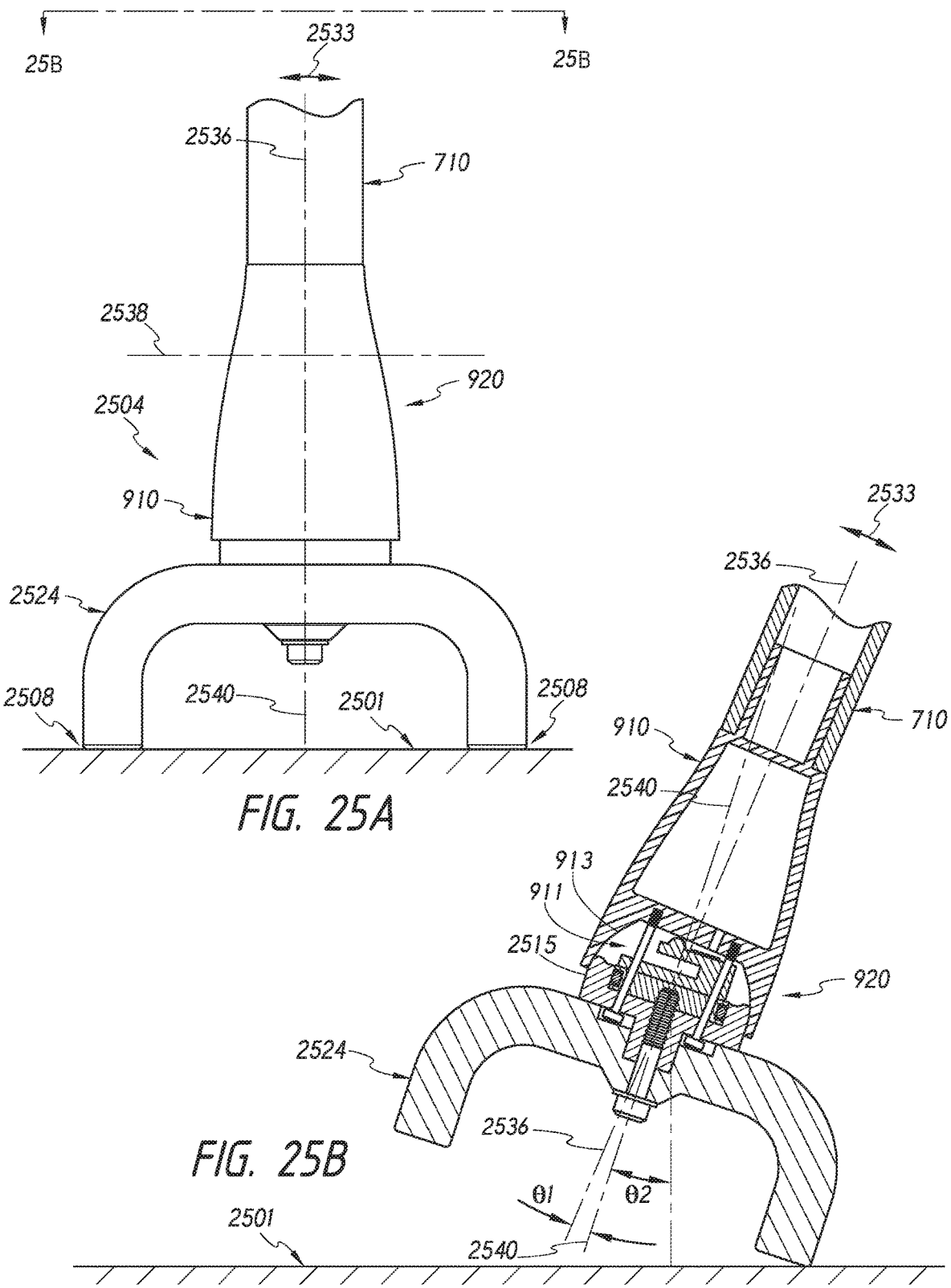

MOBILITY ASSISTANCE APPARATUS

CROSS-REFERENCE TO RELATED APPLICATIONS

The present application is a 35 U.S.C. § 371 National Stage Application of PCT Application No. PCT/US2020/033459, filed May 18, 2020, which claims the benefit of U.S. Provisional Patent Application No. 62/849,337, filed May 17, 2019, and entitled "Mobility Assistance Apparatus," the entirety of which is incorporated herein by reference for all purposes.

TECHNICAL FIELD

The application describes example of enhanced capability (also referred to as smart) mobility aid devices, such as rollators, walkers, crutches, canes and the like, as well as apparatuses, systems, and processes for enhancing the capabilities of mobility aid devices.

BACKGROUND

A variety of mobility aid devices, or simply mobility device, have been developed including canes, crutches, walkers, and rollators. Mobility aids can assist a user with various mobility challenges, such as due to age, injury or other mobility-impairing condition. For example, after an injury, a mobility aid device can help the user keep the weight of the injured limb, assist with balance, and generally help the user perform day-to-day activities. Mobility aid devices, for examples walkers and rollators, have become ubiquitous with the aging population, and can provide an important service to allow people to maintain a degree of independence, despite increasing age, injury, or other mobility-impairing condition. Canes and crutches typically have a single leg with a foot provided at the bottom of the leg and are configured to be gripped by the user for supporting one side of the user's body, e.g., to reduce the amount of weight on an injured or otherwise weakened, such as due to aging, limb. Walkers and rollators are another popular type of mobility device, which can provide a greater level of balance assistance and unloading of weight from the user's lower body. Such devices typically include a plurality of legs, usually four, that contact the ground to provide a more stable base and typically include two handles to support both of the user's left and right hands. Walker and rollators may thus al low the user to use both arms to support their weight thus allowing the user to take more of the weight off of the user's lower body when walking. Conventional mobility devices generally only assist the user with mobility challenges, such as when walking and/or participating in day-to-day activities. Thus, as mobility devices are becoming ubiquitous in daily life for certain users, designers and manufacturers of mobility devices continue to seek improvements thereto such as by enhancing the capabilities provided by mobility devices.

SUMMARY

The present disclosure relates to smart mobility devices, such as walkers, rollators, canes, crutches, wheelchairs or others, with a variety of features that enhance the capability of the mobility aid device beyond just assisting the user with a mobility challenge.

In accordance with some embodiments, a smart mobility device may include a frame configured to be rolled along a support surface, the frame including a plurality of wheels for rolling contact with the support surface, and a seat positioned above the plurality of wheels and configured to support the user in a seated position. The smart mobility device may further include a display, which in some embodiments may be positioned on the frame to face the user's back when the user is seated on the seat. The smart mobility device may further include a handle configured to be gripped by the user, and the display may be configured to be automatically powered on responsive to the handle being gripped.

In some embodiments, the smart mobility device may include multiple displays, one located in a handle of the smart mobility device and one located elsewhere. At least one of the displays of the smart mobility device may be arranged to be visible to the user when gripping the handle. In some embodiments, both of the displays may be visible to the user when gripping the handle. The smart mobility device may be configured to enable the user to set a user preference identifying one of the plurality of displays as a primary display when using the device. In some such cases, the primary display may be powered (e.g., for displaying information to the user) when the handle is being gripped, while the other display may be deactivated when the primary display is active, e.g., for conserving power. In some embodiments, one or more of the multiple displays may not be visible when the user is seated on the seat. For example, one of the displays may be located in the backrest of the seat and may face the user's back when the user is seated on the seat. In some such embodiments, the smart mobility device may be configured to detect when the user is in a seated position and may automatically deactivate at least one of the displays (e.g., the display located in the backrest) upon detection of the user in a seated position. In some such embodiments, the smart mobility device may be further configured to detect a change in condition such as a change from the user being in a seated position to the user being no longer in a seated position and may, in some such examples, re-activate the display which was de-activated upon the detected seated position.

In some embodiments, one or more sensors may be integrated into the smart mobility device for determining a change in condition (e.g., for detecting a grip of the handle, detecting a user in a seated position or a transition from a seated position to the user no longer being seated). The smart mobility device may include at least one sensor configured to detect a grip of the handle, and more specifically of a grip portion of the handle. In some examples, the one or more sensors may include one or more touch sensors, capacitive sensors, pressure sensors, force sensors, and/or strain gauge on the handle. In some examples, a grip may be detected based on detected touch at two different peripherally spaced locations on the handle (e.g., a location likely to be contacted by the user's palm and by a user's finger). In some examples, a grip may be detected responsive to detection of a squeezing force on the handle, which may be detected using one or more pressure sensor, force sensors, or strain gauges. Sensor data from the one or more sensors may be communicated to a processor onboard the smart mobility device, which may analyze the sensor data to detect the change in condition (e.g., to detect a grip, a seated position, or unloading of the seat indicating the user had stood up).

In some embodiments, the smart mobility device may include at least one sensor configured to detect whether the user is in a seated position and/or has stood up following being seated. In some such examples, the smart mobility device may include a proximity sensor having its detection beam directed to the seating area of the smart mobility device. For example, a proximity sensor, such as and without limitation an optical sensor, an ultrasonic sensor or a suitable RF sensor, may be located on the backrest (e.g., proximate the display on the backrest, or elsewhere on the backrest), on the frame, or on the seat and facing in a direction pointed in the general area between the seat and the backrest for detecting an object, such as the user, within the seating area. In some embodiments, the smart mobility device may include one or more load cells, strain gauges or another suitable sensor to detect a load being supported by the seat. In some embodiments, sensor data from a load-measuring sensor on the seat may be analyzed in conjunction with load data from other locations of the smart mobility device, e.g., from the storage container, the handle(s), or elsewhere on the frame, to identify the source of a loading condition (e.g., the user being seated on the seat, items being supported in the storage container, or force being applied on the handles) and thus isolate a condition representative of the user being in a seated position from other loading conditions of the smart mobility device. The smart mobility device may include any suitable number or combination of sensors, such as and without limitation a load cell, a strain gauge, a camera, a proximity sensor, or a touch sensor, to determine whether the user is in a seated position. In some embodiments, upon the determination that the user is in a seated position, the processor may generate a seated mode signal which may be communicated to one or more other electronic components of the smart mobility device and/or used to control operation of the one or more electronic components (e.g., to deactivate or power down a given component such as the back rest display).

In some embodiments, the processor may analyze the sensor data, e.g., for identifying a load on the smart mobility device, for tracking user activity, and/or deriving information pertaining to the user's health. The smart mobility device may be configured to generate a gait measurement and/or a standing/walking load on the device. A load on the smart mobility device may be measured in a variety of ways. For example, a load cell may be located in the base (e.g., the tip in the case of a cane or crutch) of the smart mobility device. The load cell may be provided with a hard stop to prevent or restrict the load cell from over deflecting, which may damage the load cell. The load cell may be positioned in the base, such that it is deflected every time a load is placed on the mobility aid device, such as by the user at least partially supporting their weight with the mobility aid device, and the amount of deflection of the load cell may be used to determine the amount of load being placed on the smart mobility device each time. In other examples, a load cell (e.g., a coin load cell) may be placed at other locations, for example in the wheel (e.g., in the wheel shaft), in the handle, between the handle and the body (e.g., leg or frame) of the smart mobility device or within the body of the smart mobility device and operatively arranged to deflect and measure a downward load on the device. In yet further examples, a strain gauge may be used instead of or in combination with a load cell or other suitable load-measuring sensor. A strain gauge may be located on any surface or component, which deflects during loading of the smart mobility device, One or more strain gauges can be placed on a structural component of the smart mobility device (e.g., the handle, the body, the frame, the wheels, the tip) or a non-structural component, including but not limited to any flexible printed circuit board (PCB) which may also deflect during use of the device. In the case of the latter, cadence measurements may be obtained from the periodic deflection of the non-structural component, while for an accurate determination of loading on the device, sensor data may be obtained from sensors operatively associated with structural (i.e., load-bearing) components of the smart mobility device. In some embodiments, the motion (e.g., kinematics) of the smart mobility device may be derived from on-board sensors, including but not limited to motion sensors, accelerometers, inertial measurement units (IMUs) or others, embedded in the smart mobility device, and based on which information about the user's activities and/or health may be derived. In some examples, the sensor data from multiple sensors (e.g., an IMU or other type of motion sensor in the handle and another in the base of the mobility device) may be used in conjunction to derive motion or kinematics of the mobility device.

In some embodiments, the smart mobility device may be configured to generate a gait measurement and/or track trends relating to the user's gait. In some embodiments, the load measurements may be used to derive a cadence, which may be used in combination with distance travelled to derive a gait measurement (e.g., a length of the user's step). Gait measurements may include measurement of one instance in time or an average of a plurality of measurements over a period of time and/or the gait measurements may be recorded and analyzed for trends (e.g., a user's step increasing or decreasing in length, stability, etc.). A distance travelled may be obtained using a variety of suitable techniques including but not limited to measuring the rotation of the wheels and computing the distance from the number of rotations and diameter of the wheels, or via a GPS or other geolocation system. Gait measurements may additionally or alternatively be obtained using other sensors, such as a camera, which capture image data of the user's lower body (e.g., legs and or feet). The image data from the camera may be processed using any suitable computer vision technique (e.g., image segmentation, or machine-learning object recognition) to identify the user's legs or feet in the image data and measure the distance between the user's legs or feet for obtaining a gait measurement. In some examples, a gait measurement may be taken from the frames or instances in time where the user's legs or feet are determined to be farthest apart. In some embodiments, the image data may be processed to instead identify instances in time or frames in which the user's feet contact the ground or are closed to the ground, and a gait measurement may be taken from those frames. Other techniques may be used to obtain gait measurements and/or other information about the user's kinematics.

In some embodiments, the smart mobility device may include one or more cameras. In some embodiments, the smart mobility device may include at least one forward facing camera and the smart mobility device may be configured to identify obstacles in the path of the smart mobility device for obstacle avoidance. In some such embodiments, the smart mobility device may be configured to provide autonomous (e.g., fully autonomous), semi-autonomous (e.g., steering only but no powered driving of the device) control and/or alerts to the user. In some embodiments, one or more of the cameras on the smart mobility device may be operated, per user preferences, for automatic or triggered recording images (e.g., still photos or video) for personal use by the user (e.g., for posting on a user's social media cite or otherwise sharing with others), which enables the user to capture the moment without having to relinquish control/handling of the mobility aid device. In some embodiments, the smart mobility device may include one or more rear-facing cameras 334-1 (e.g., a camera directed toward an upper body of the user, a camera directed toward the lower body of the user). Image data from such cameras may be used for various functions performed by the smart mobility device, such as for user identification, gait measurements, posture monitoring and alerts, or other activity or status tracking.

In some embodiments, upon user identification, which may be performed automatically in some cases by the smart mobility device using sensor data from one or more of the on-board sensors, the smart mobility device may automatically apply user-specific settings for the smart mobility device. For example, the smart mobility device may queue up (e.g., assign to speed dial or emergency protocol numbers) the user's specific contact list. Other user-specific settings may include but are not limited to applying, lighting level settings for the one or more lights of the smart mobility device and/or back lighting of the displays, present volume levels associated with various functions, such as listening to audio, making voice calls, sounding of alerts, and/or sounding of notification to bystanders. Other user-specific settings may include but are not limited to autonomous/semi-autonomous driving settings (e.g., amount of braking force, normal travel speed), sensitivity of controls (e.g., sensitivity of touch-sensors, microphones, etc.), noise cancellation functions, etc.

In some embodiments, the smart mobility device may include one or more light sources (or simply lights) configured to operate (e.g., turn on and off, or activate/illuminate in a pattern) in different modes based on a detected change of condition. For example, one or more of the lights of the smart mobility device may turn on and off in a pattern, they may light up in different colors or on/off frequencies depending on the detected condition or change of condition. In some such examples, at least one of the lights may be configured to operate at a first frequency (e.g., a relatively faster blinking rate) or have a first illumination color (e.g., illuminate in an orange color) when an emergency condition has been detected and to operate at a second frequency (e.g., a relatively slower, compared to the emergency condition, blinking rate) or have a second illumination color (e.g., illuminate in white) when no emergency condition has been detected.

In some embodiments, the smart mobility device may be configured to detect an emergency condition, such as detect if the user has fallen, and may perform certain automatic functions, such as initiate an emergency transmission, switch or activate the lighting to the emergency mode, sound an audible alert such as to alert any by passers, activate microphones, speakers and or emergency buttons at an appropriate location of the device such as near the base and in some cases on a particular side (e.g., left or right side) of the base where the user has been detected to have fallen. A variety of other functions may be tailored (such as tailoring the function associated with a soft control or other aspects of a graphical user interface) based on a detected change of condition, as described further below.

As described further below, the smart mobility aid device may include one or a plurality of electronic communication components configured to communicatively couple the smart mobility device to an external electronic device, for example a computing device (e.g., laptop, smartphone, tablet, smart watch, etc.) of the user, a care giver, or a healthcare provider. In some examples, the external electronic device may be the other one of a set of smart or semi-smart mobility aid devices. For example, each of a pair of smart crutches may be configured to be communicatively coupled to one another to share information and in some cases, at least one of the pair of smart crutches may be configured for communicatively coupling to an electronic device other than the set of crutches (e.g., a device of the user or the storage device on the cloud) for transmitting user data thereto. In some examples, transmission of user data may occur automatically and periodically, for example at pre-set intervals of time, which may be a user setting or controllable by a person other than the user (e.g., a guardian, caregiver, healthcare provider), or upon the meeting of a certain criteria, e.g., upon failing to detect the user in proximity to the smart mobility aid device, or detection by the smart mobility of a new user in proximity.

The smart mobility aid device may include additional or alternative features that enhance the usability or functionality of the smart mobility device. For example, the smart mobility device may be foldable, such as by using a scissor-type folding linkage or any other suitable folding linkage between the two sides of the frame. The frame or body of the smart mobility device may be otherwise adjustable, such as to adjust the length of the body or a frame member, and in some cases the body or frame member may be adjustable at two distinct spaced apart locations. In yet further embodiments, the smart mobility device may include removable and interchangeable (also referred to as modular) components for tailoring the mobility aid device for different use cases. For example, the mobility aid device (e.g., walker, roller, wheelchair) may include a storage container which is removably coupled to the mobility aid device and in some cases interchangeable with other storage containers that provide other functions, such as temperature control of the items in the storage container, secure storage that may be enhanced by biometric security features, aesthetics, division of the storage container into compartments, etc. In some embodiments, alternative to or in addition to the storage container, the mobility aid device may be equipped with one or more hooks or other suitable structures for connecting the user's belongings (e.g., a grocery bag, a purse, etc.) to the body of the mobility aid device. In some examples, a base or components associated therewith (e.g., a tip of a cane or crutch, a wheel of a rollator, wheelchair, or walker) of the mobility aid device may be removably coupled to the body of the mobility aid device for reconfiguring the mobility aid device for various use cases such as traveling on different surfaces requiring different traction, width, etc., and/or the addition of further functionality by adding electronic components via a smart base (e.g., the smart tip 900 or smart tip 2500 described below).

According to further examples herein, in use the smart mobility device user can receive applications and services from a cloud based software platform via the smart mobility device. In some examples, in use the smart mobility device user can order and receive services from a cloud based software platform via the smart mobility device. In some examples, in use the smart mobility device user can order and receive services from a cellular network via the smart mobility device. In further examples, in use the smart mobility device a user can receive applications and services from an application store via the smart mobility device. In other examples, the one or more electronic communication components can provide for entering user data into the smart mobility device using a smart device. In yet other examples, the smart device can be a smartphone, a smart watch, a smart glass, a tablet, a laptop or a computer. In still other examples, in use the display can provide information about the user progress on a game based on user targets. In some examples, in use the display can provide information about the result of a social game wherein the user's activity tracking can be compared to another user. In other examples, the memory can contain information about a daily activity pattern of the smart mobility device user. In yet other examples, the daily activity pattern can be a notification for the smart mobility device user's medication schedule. In another example, the notification can be sent automatically from the smart mobility device to a caregiver, a doctor or an involved party. In yet other examples, the smart mobility device can be adapted and configured for use with a mobile payment system. In further examples, the smart mobility device can be used by the smart mobility device user as a payment method for services available from a software platform or an app store. In yet further examples, the smart mobility device can be integrated with a mobile payment system. In still further examples, the smart mobility device can further include an emergency button that when pressed establishes communications with one or more of a caregiver or an emergency service (e.g., place a 911 call).

As will be further described below, the smart mobility device may provide reminders or alerts to the user. The smart mobility device may be configured to be connected to the user's electronic calendar and/or may be programmed with a schedule of events or appointment that the user would like to be reminded of. As an example, the smart mobility aid device can be configured to alarm, notify, and/or remind a mobility aid device user or another interested party (e.g., a caregiver) about a smart mobility device user medication schedule using a voice reminder, a vibration reminder and/or an on screen reminder, or in the case of a third party a text message, email, or the like. In another example, when a mobility aid device user takes a medication according to a medication schedule a caregiver or any other interested party (e.g., the user's doctor) may be notified. In other examples, the medication schedule of a smart mobility aid device user can be modified, entered, managed, updated and/or tracked by the mobility aid device user, a caregiver, or a doctor. In yet other examples, the smart mobility aid device can be adapted and configured to communicate and connect to a regular medicine container or a smart medication container, and/or to a merchant (e.g., a pharmacy) for re-ordering a medication of the user. The smart mobility aid device may provide a variety of other services or alerts to the user including but not limited to a daily or other periodic alert to charge the device, such as by wireless charging.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several examples in accordance with the disclosure and are, therefore, not to be considered limiting of its scope, the disclosure will be described with additional specificity and detail through use of the accompanying drawings, in which:

FIG. 25A shows a simplified elevation view of an example of a smart tip for use with a mobility aid device, including a flexible coupling.

FIG. 25B shows a cross section of the smart tip of FIG. 25A taken along section line 25B-25B of FIG. 25A, in an example of a tilted configuration.

DETAILED DESCRIPTION OF PREFERRED EMBODIMENTS

Figure 1:
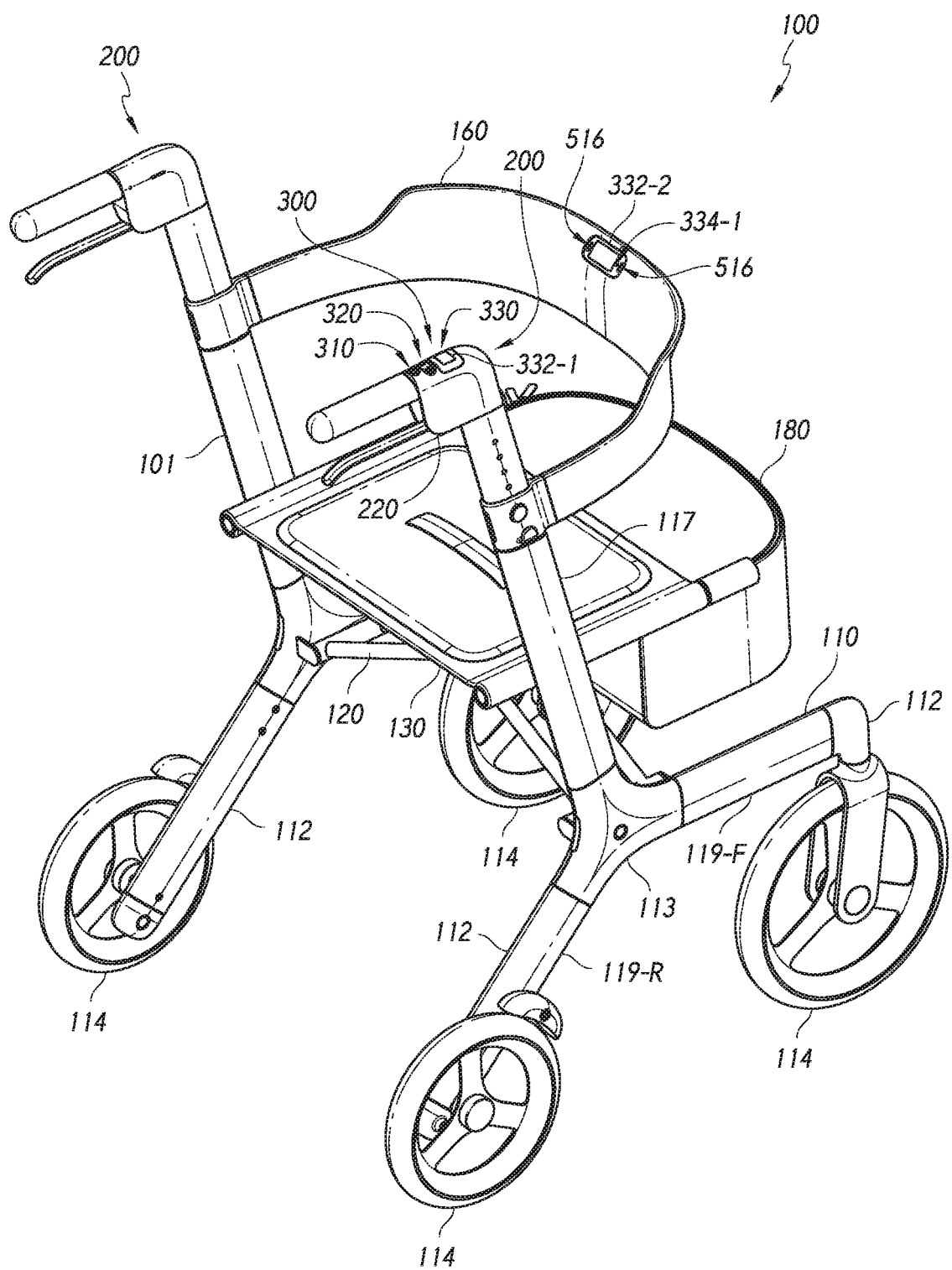
FIG. 1 shows a rear isometric view of a mobility aid device according to some examples of the present disclosure.

In the following detailed description, reference is made to the accompanying drawings, which form a part hereof. The illustrative examples described in the detailed description and illustrated in the drawings are not meant to be limiting but are provided as examples to aid in the understanding of the claims. In other examples, changes may be made without departing from the spirit or scope of the subject matter presented herein. It will be understood that the elements or components described herein, and illustrated in the Figures, can be arranged in other combinations, such as by substituting, combining, eliminating, or modifying components in other configurations, all of which modifications are contemplated herein.

Examples of enhanced mobility aid devices are described herein, which may provide a wide array of additional functions beyond simply mobility assistance. Such mobility aid devices may thus also be referred to herein as smart or multi-function mobility aid devices (or simply mobility devices). Examples of smart mobility aid devices according to the present disclosure may provide a variety of functions associated with user safety, user monitoring (e.g., health monitoring) or tracking of user activity, and connectivity. Such enhanced mobility aid devices may help the user to be more independent and healthier. Additionally, sensor data from a variety of health monitoring and/or biometrics sensors integrated into the mobility aid device may be used to analyze the user's use of the mobility aid device to determine whether the user is using the device properly and/or to provide recommendation for the proper use or reconfiguration of the device or for switching to a different type of a mobility aid device.

Smart mobility aid devices according to the present disclosure may include sensors to collect, monitor, analyze and/or represent data including but not limited to biometrics and activity tracking, safety and emergency functions, and general connectivity of the user via the mobility aid device. The activity tracking may include tracking a number of steps, distance (e.g. miles), activity speed and/or activity type, as well as user applied pressure on the mobility aid device (e.g., for assessing/monitoring the user's strength and thus health). Various data about the user that is recorded by the mobility aid device may be used (e.g., further analyzed or tracked over time) to determine parameters relating to the user's gait, which in turn can provide information about the user's health. Biometric data may include but is not limited to blood or heart-related information such as blood pressure, blood sugar, heart rate, oxygen level/rate, ECG data, EMG data, muscle strain, humidity, hydration level, and/or body temperature. In some embodiments, safety and emergency features of a smart mobility aid device may include an emergency button, one or more lights, fall detection and warning functionality, and/or user activity pattern collection and analysis of activity pattern changes. In some embodiments, sensors may be placed on the mobility aid device walker, rollator, crutches, wheelchair, etc.) to collect and monitor user data automatically. User data, such as activity tracking data, may in some cases be presented to the user in the form of visual information, sound/voice representation or alerts, and/or vibrational feedback or alerts. A smart mobility aid device may provide the user with connectivity to other electronic devices, such as a mobile phone, laptop, computer, or cloud storage or cloud based applications associated with the user or with a caregiver or healthcare provider. The smart mobility aid device may include an external communication interface, including at least one or in some cases a plurality of electronic communication devices such as Bluetooth, and or/and a SIM card or other communication module to enable authentication and communication via a cellular network. A smart mobility aid device according to the present disclosure may analyze how a user walks using the device and advise a user on how to improve his walking pattern, recommend the use of different mobility aid device and/or give the user and/or others (such as health care provider or caregiver) information about the user's health (e.g., current metrics and/or information about patterns such as declining or improving health) or status (e.g., location).

One example of information that may be tracked by the smart mobility aid device (also referred to as a smart mobility device) may be distance travelled, which may be achieved, for example, by way of odometry measurements/calculations. Any suitable odometer, such as a mechanical, electro-mechanical, or computerized (e.g., magnetic-based) odometer, may be operatively associated with a rotational component (e.g., at least one wheel of the rollable mobility aid device) to track the distance traveled. The distance travelled may be stored (e.g., in non-volatile memory 524), transmitted to the processor 530 for use in further analysis and/or computations, and/or reported to the user (e.g., on any of the displays 332-1, 332-2, etc.). As described herein, the different displays may be configured to be active (e.g., to display information) at different times depending on a detected condition or change of condition. In some embodiments, multiple displays may be active and/or display information concurrently. For example, one display (e.g., display 332-2) may provide one type of information (e.g., distance travelled and thus functioning as an odometer), while the other display (e.g., display 332-1) concurrently or on-demand responsive to pushing a button, provides a different type of information or functionality, such as displaying a time of day, information about incoming call or other notification (e.g., upcoming appointment) or alert (e.g., low battery), settings for reconfiguring functions, or any other interface related to functionality of the intelligence system, without interruption to or affecting the functionality or display on the first display. At least one of the displays (e.g., display 332-2) may be configured to display information thereon (e.g., an odometer reading) in a size suitable for consumption by the appropriate demographic of user. For example, the display may display the odometer reading (e.g., distance travelled) in a size which an elderly user can perceive without vision enhancement. The display font size may be adjustable by the user (e.g., by a user interface provided on the other display and/by an app on the user or caregiver's smart phone, which transmits the settings to the smart mobility aid device). The smart mobility device may be configured to track and optionally display odometer readings of different categories (e.g., a trip distance travelled, period distance travelled such as in a day, week, bi-week, a month, or any other period of time that may be set by the user or caregiver, or total distance travelled cumulative for all trips or periods of use of the smart mobility device after initial activation by the user). In addition to odometer readings, the display may provide other information related to distance travelled, such as congratulatory or encouraging messages, comparison to other users, comparison to a previous day or other period, and information about trends or combinations thereof (e.g., indicate an increase of walking as tracked over a week, month, etc., with a congratulatory or encouraging message).

Components used to obtain odometry measurements include, but is not limited to, mechanical mechanisms, video, electro mechanical sensors, optical, magnetic sensors. Distance tracking or odometry may be achieved, for example, using a mechanical odometer (e.g., a mechanical counter which uses a toothed ring and finger to count revolutions of a wheel or shaft), a magnetic sensor (e.g., a Hall effect sensor or other suitable magnetic sensor), an optical interrupt sensor, and/or any currently known or later developed computerized odometer (e.g., one using a magnetic sensor to count revolutions). One specific and non-limiting example of a magnetic sensor, which can provide suitable resolution, may be the TRIAXIS sensors provided by MELEXIS or other suitable miniaturized 3D magnetic sensor. The sensor may be located at a wheel or individual sensors located at each of the wheels of the mobility aid device, and the sensor data may be coupled to the processor 530, The sensor data may be coupled to other components of the intelligence system (e.g., processor 530) via any suitable communication link (e.g., individual/dedicated wiring or cable harness for each sensor, a common serial bus (e.g., a 1-wire two-way communication bus) or other suitable communication link. Utilizing two-way communication links to the location of sensors in the wheels may enable additional functionality such as providing light (e.g., LED) sources, buttons (e.g., emergency button), speakers, microphones or others to be located peripherally (e.g., on parts of the frame remote from the processor) and supported (e.g., electronically connected to the processor) by the same bus.

As described, distance travelled may be a useful bit of information, which can also be used in combination with other information to derive yet additional information or bio-metrics about the user (e.g., gait measurements). For example, the gait of a typical user when using a walker may be described as a rhythmic step and slide of the walker. The distance of the slide each time may have a specific character. If this character changes this may be an indication of a change in health status. Additional utility is achieved by including an odometer on both right and left wheels. Not only does it provide redundancy and double the data available, but it can also detect asymmetry of motion that may be indicative of particular health status change, including the onset of a stroke.

A smart mobility aid device may be configured to use a sensor to recognize an authorized user. Upon recognizing an authorized user, the smart mobility aid device may power up, unlock, display or play a welcome message or take other actions. For example, a smart mobility aid device may be configured to turn on and off automatically, e.g., responsive to a detected grip by the user or other contact or proximity of an authorized user with the mobility aid device. For example, the mobility aid device may include a grip sensor positioned in the handle to detect the handle being gripped. The grip sensor may be in communication with a processor configured to power up a display (e.g., either or both of the displays 330 or 332-2) responsive to the handle being gripped. One or more sensors, such as provided in a grip portion of a handle of the mobility aid device, may automatically turn the power on to one, some or all of the electronics on the mobility aid device, upon detection of the grip, contact, proximity, or other recognition of the user. In other examples, the detected grip, contact, proximity, or other recognition of the user may power or activate certain ones of the electronics or function (e.g., a camera and/or display, certain safety functions such as automated lighting functions, depending on ambient lighting conditions) but not others (e.g., communication functions such as to transmit user data and/or place voice/VIOP calls) until an authorized user has been authenticated by the device. As described further below, the smart mobility aid device may be configured for self-charging (e.g., via one or more energy harvesters) and/or equipped with a charging circuitry for receiving electrical power from an external source (e.g., via a wired or wireless connection to an external power source). Wireless charging of the mobility aid device may be achieved via any suitable wireless charging mechanism (e.g., via inductive charging, whether Qi compliant or not, via inductive radio or resonant charging). In some embodiments, a charging apparatus for a mobility aid device may be further configured to enhance the ease of use by including a magnetic coupling that assists with the alignment of the mobility aid device to the charger. In embodiments, the base of the mobility aid device may be configured to allow the user to tailor the device for different use conditions. For example, a component of the device that contacts the ground, such as the foot or tip of a cane or crutch or the wheels of a rollator, wheelchair, or walker may be interchangeable allowing the user to couple a different such component (e.g., wheel of different diameter or providing different level of cushion, or a tip with a different pliability or number of contact points) depending on the use condition.

FIGS. 1-12 illustrate views of a smart mobility aid device 100 according to the present disclosure, in this case configured as rollator 101. The rollator 101 includes a frame 110, which supports two handles 200, one or both of which may include electronic components for providing the enhanced functionality of a smart mobility aid device 100 according to the present disclosure. In the example shown, the frame is configured to be rolled along a support surface responsive to force applied by a user. The frame includes a plurality of wheels for rolling contact with the support surface, and a seat positioned above the plurality of wheels. For example, the rollator 101 includes a display 332-2 positioned on the frame to face the user's back when the user is seated on the seat. The rollator 101 includes a handle configured to be gripped by the user for applying the force. The display 332-2 may be powered on, responsive to the handle being gripped. As shown for example in FIG. 1 and described further below, the rollator 101 may include a user interface 300 at least some of the components of which are provided, in this example, on the handle 200. For example, the rollator 101 may include an additional display 330 arranged on the frame to be visible to the user when the user is seated on the seat. For example, the rollator 101 may include a display 330 located on the handle 200. Both the display and the additional display may be visible to the user when gripping the device for walking. The handle 200 may include one or more user controls (e.g., emergency button 310 and light controls 320) which may be implemented as mechanical user controls or as touch-sensitive controls which may be separate from or an extension of the display 330. User controls may be located on a side of the handle opposite the display. In some examples, the portion of the user interface 300 embedded in the handle may be provided substantially by a touch sensitive display, which provides both the display and control functionality associated with the intelligence system of the mobility aid device 100. As further described below, electronic components of the smart mobility aid device may be built into the handle 200 and/or frame 110. As will be appreciated, and while components of the handle 200 including user interface features of the mobility aid device, are described here with reference to a handle of a rollator, the handle 200 may have a different suitable shape and be provided on a different type of a mobility aid device, such as a crutch (as in the examples in FIG. 13-20) or another type of a mobility aid device including but not limited to canes, walkers, scooters and wheelchairs.

The frame 110 is configured to be rolled along a support surface (e.g., the ground) responsive to a force (e.g., pushing force) applied by a user. The frame 110 is thus provided with a plurality of wheels 114 for rolling contact with the support surface. In the example in FIG. 1, the rollator includes four legs 112 at the end of each of which is a wheel 114. In other examples, the mobility aid device 100 may include a greater number of wheels (e.g., in some cases, a plurality of wheels may be provided at the end of each leg) or a fewer number of wheels. In some examples, the mobility aid device 100 may be a walker and include fewer number of wheels than legs. In some examples, the wheels 114 may be arranged such that front wheels and the rear wheels of the mobility aid device 100 are substantially in-line. In other examples, the wheels may not be in-line. For example, as shown in FIG. 2, the rear wheels 114-R may be spaced farther apart from one another than the front wheels 114-F to define a wider base are the rear, which may provide a more stable base at the rear of the mobility aid device 100 where a substantial portion of the user's weight is applied.

Figure 2:
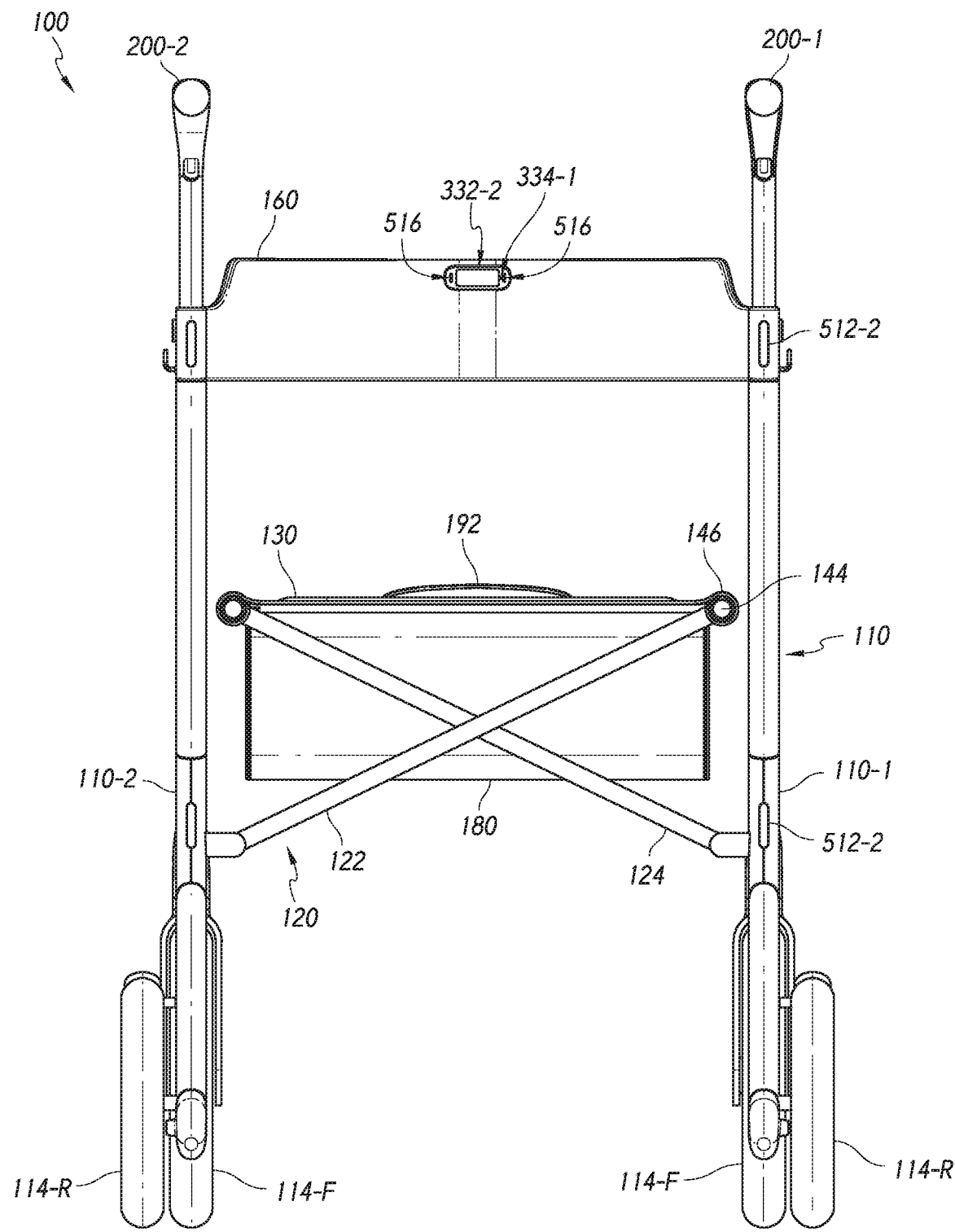
FIG. 2 shows a rear view of the mobility aid device of FIG. 1.

As further shown in FIG. 1, the frame 110 supports a seat 130 and at least one handle 200 configured to be gripped by the user, such as when walking with the assistance of the mobility aid device 100. In the example in FIG. 1, the frame 110 includes a left frame portion 110-1 and a fight frame portion 110-2, each of which is associated with a respective handle 200-1, 200-2. The frame 110 may be implemented using hollow tubular members. The hollow tubular member may have circular, oval, or circular-flattened, or a cross-section having other regular or irregular shape, as may be desired for function or aesthetics. The hollow interior of the tubular frame members may enable the installation of the wiring for connecting the various electronic components (e.g., sensors, display and/or processors) internally to the frame structure thereby concealing it from view, which may enhance the aesthetics of the mobility aid device 100. In the particular example shown in FIGS. 1-4, the right and left frame portions are symmetric and each includes an upper tubular frame member 117, which is coupled, via the frame junction 113, to a front lower frame member 119-F and a rear lower frame member 119-R, each of which terminates at a respective front and rear wheel 114-F and 114-R to define a front and rear leg of the mobility aid device 100. The frame 110 of the mobility aid device 100 may be adjustable to suit users of different stature. For example, a length of a portion of the frame, such as the length of each of the upper frame members 117 may be adjustable (e.g., via push buttons 115 shown in FIG. 4) to enable adjusting the height of the mobility aid device to suit different users. The height adjustability may be effected by the use of telescoping members for any of the frame members, such that depressing the push button allows the telescoping members to move relative to one another and releasing the push button locks out the telescoping members preventing relative movement. The frame may be adjustable at multiple locations, for example, at a location above the frame junction 113 (e.g., to adjust for different user heights) and at a location below the frame junction 113 (e.g., at a location along the front lower member 119-F such as to lengthen the member 119-F and thus increase the side of the base of the mobility aid device).

A variety of other adjustments may be provided to enable further tailoring of the mobility aid device to differently sized users.

Figure 3:
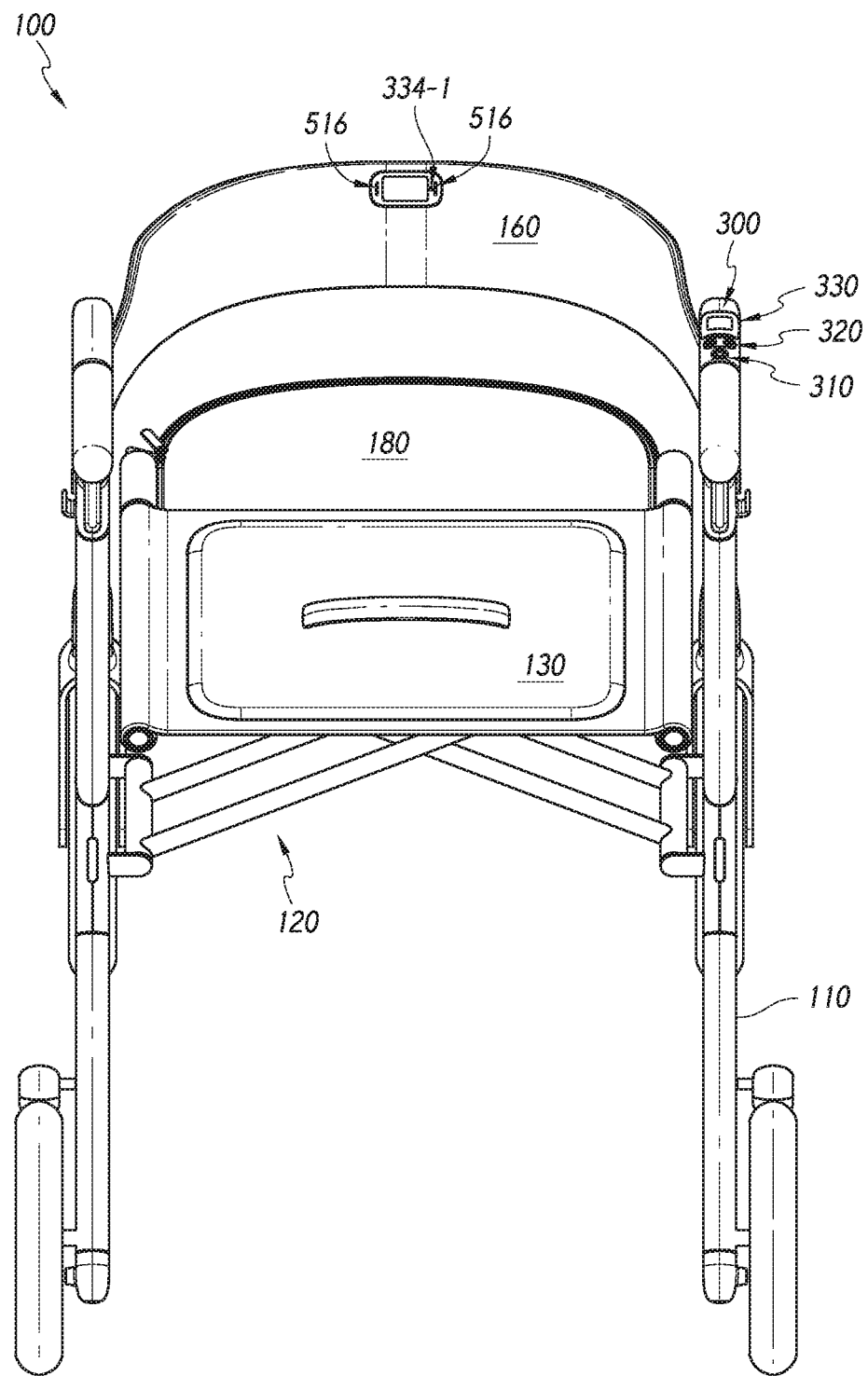
FIG. 3 shows another view of the rear of the mobility aid device of FIGS. 1 and 2.
Figure 4:
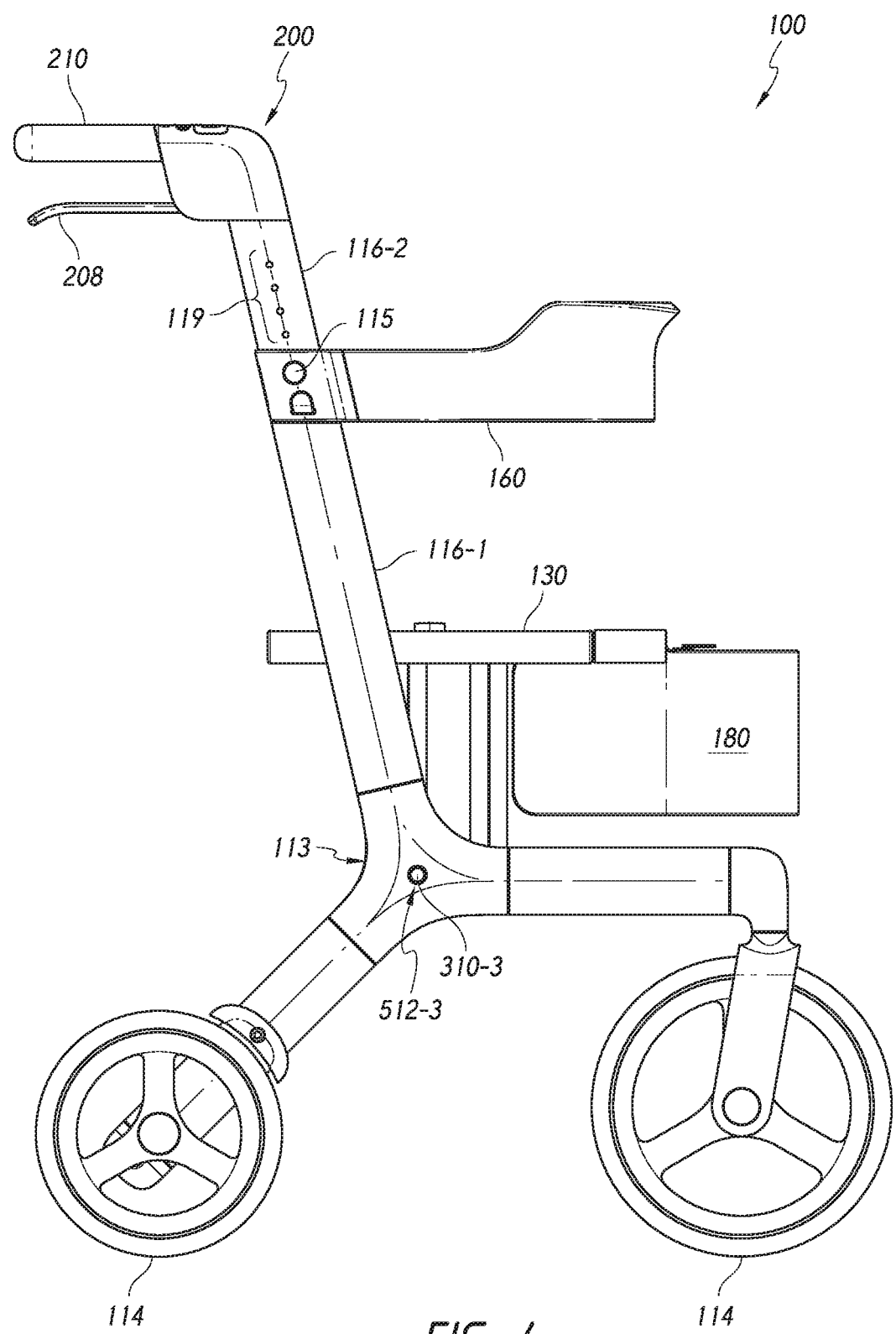
FIG. 4 shows a side view of the mobility aid device of FIG. 1.
Figure 5A:
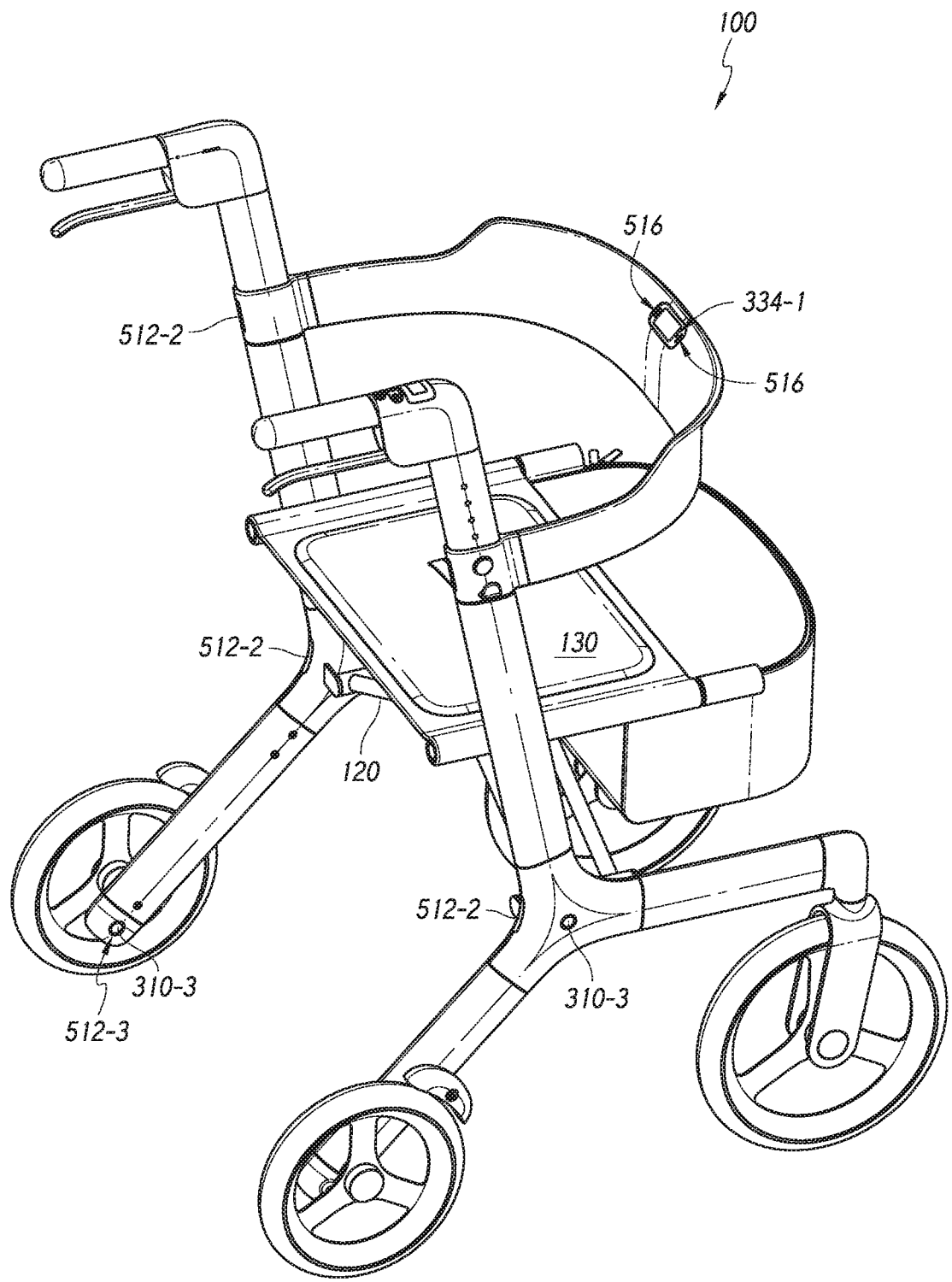
FIGS. 5A and 5B show rear isometric views of the mobility aid device of FIG. 1 in two configurations including a use configuration and a folded configuration, respectively.
Figure 5B:
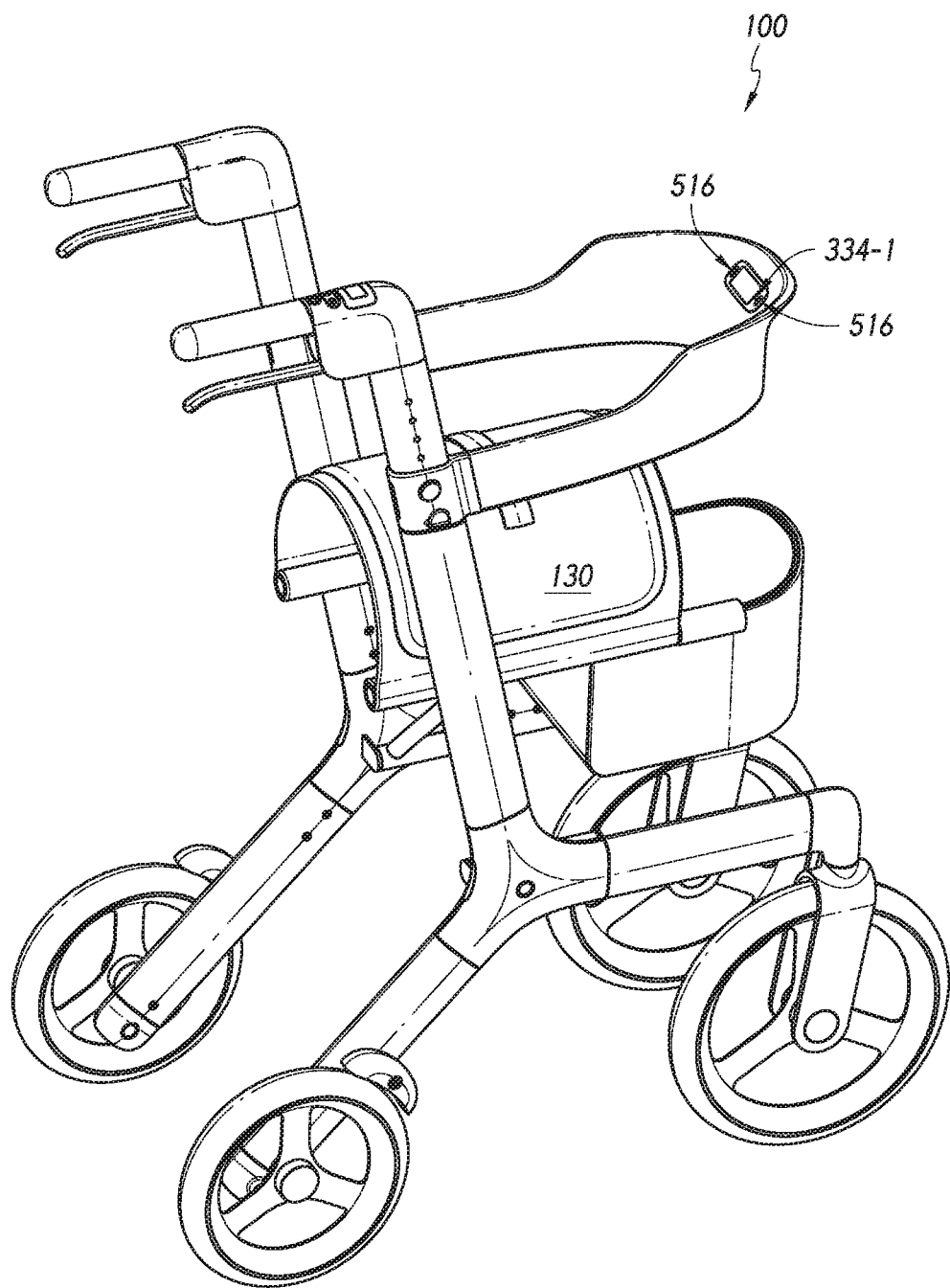

A mobility aid device may include a frame that is foldable such that the device can be provided into a storage configuration, which is more compact than a use configuration. For example, the left and right frame portions 110-1 and 110-2 may be movably coupled to one another to allow the mobility aid device 100 to be folded into a more compact configuration (e.g., for transport and/or storage), e.g., as shown in FIGS. 5A-5B. Referring also to FIGS. 2 and 3, the left and right frame portions 110-1 and 110-2 may be coupled together using a folding linkage 120. The folding linkage 120 includes a corresponding left link 122 pivotally coupled to the left frame portion 110-2 at a left pivot joint 126, and a right link 124 pivotally coupled to the right frame portion 110-1 at a right pivot joint 128. The left link 122 extends from the left frame portion 110-2, and specifically from the left pivot joint 126 toward the right frame portion 110-1, and the right link 124 extends from the right frame portion 110-1, and specifically from the right pivot joint 128 toward the left frame portion 110-2, The left and right links 122 and 124, respectively, are arranged to pivot with respect to one another about a mid-portion 121 of the folding linkage 120 so as to move in a scissor action when the frame 110 is folded (e.g., into the compact configuration) and unfolded (e.g., into the use configuration). While the links 122 and 124 pivot relative to one another, the links need not be pivotally coupled to one another. In an example arrangement shown in FIGS. 1-3, each of the links 122 and 124 is implemented using a plurality, in this case a pair, of parallel spaced-apart link members. Each set of link members is pivotally connected to the respective side of the frame via the respective left or right pivot joint, which in this example is implemented as a tubular member pivotally supported on a pin fixed to the frame. The spaced-apart left link members are interleaved with and do not contact the right link members.

The seat 130 is coupled to the frame 110 (either removably or fixedly) and operatively positioned above the wheelbase to support the user in a seated position. The seat 130 is supported on the frame between the left and right frame portions 110-1 and 110-2 in a manner, which does not impede the folding of the frame. In the present example, the seat 130 extends between the left and right frame portions, in some cases connecting the left frame portion to the right frame portion. In the present example, the spaced-apart link members provide a support for the seat 130. The seat support in the present example is implemented using a pair of left and right seat bars coupled to the free ends of the links 122 and 124 and extending generally horizontally from the rear towards the front of the rollator 101, with the seat being connected to span the distance between the two seat bars. In other examples, the seat may be differently supported on the frame, such as being fixed directly to the frame or coupled to support structures fixed to the frame. The seat can be made of any suitable material such as fabric, leather, plastic, and/or composite materials. In some examples, at least a portion of the seat, such as a middle portion, may be flexible to allow the seat to bend or fold (e.g., as shown in FIG. 5B), enabling the folding of the mobility aid device 100.

The seat 130 may include one or more load sensors, e.g., one or more load cells or strain gauges. The load sensors may be configured to measure the weight of the user in a sitting position and transmit information associated with the user's weight to the processor (e.g., processor 530). The processor may be configured to display the information on at least one of the displays (e.g., display 332-1 or 332-2). One or more load cells or other load measuring devices operatively associated with the seat may be used to track the user's "seated weight" over time. While the "seated weight" may not be indicative of the user's actual weight, tracking of the user's "seated weight" over time can be used to derive trends (e.g., weight loss or weight gain, leg strength increase or loss based on a decreasing seated weight measurement). In some examples, a seated weight measurement (or an average over a period of time such as over the duration of time during which the seat is in continuous use in a given instance) may be automatically recorded each time the user is detected to be in a seated position. The seated weight measurements over a day, a week, or another duration of time may be collected and analyzed for trends, either by the processor of the mobility aid device, or by a remote processor such as a processor of a computing device of the user or another person associated with the user.

Figure 6A:
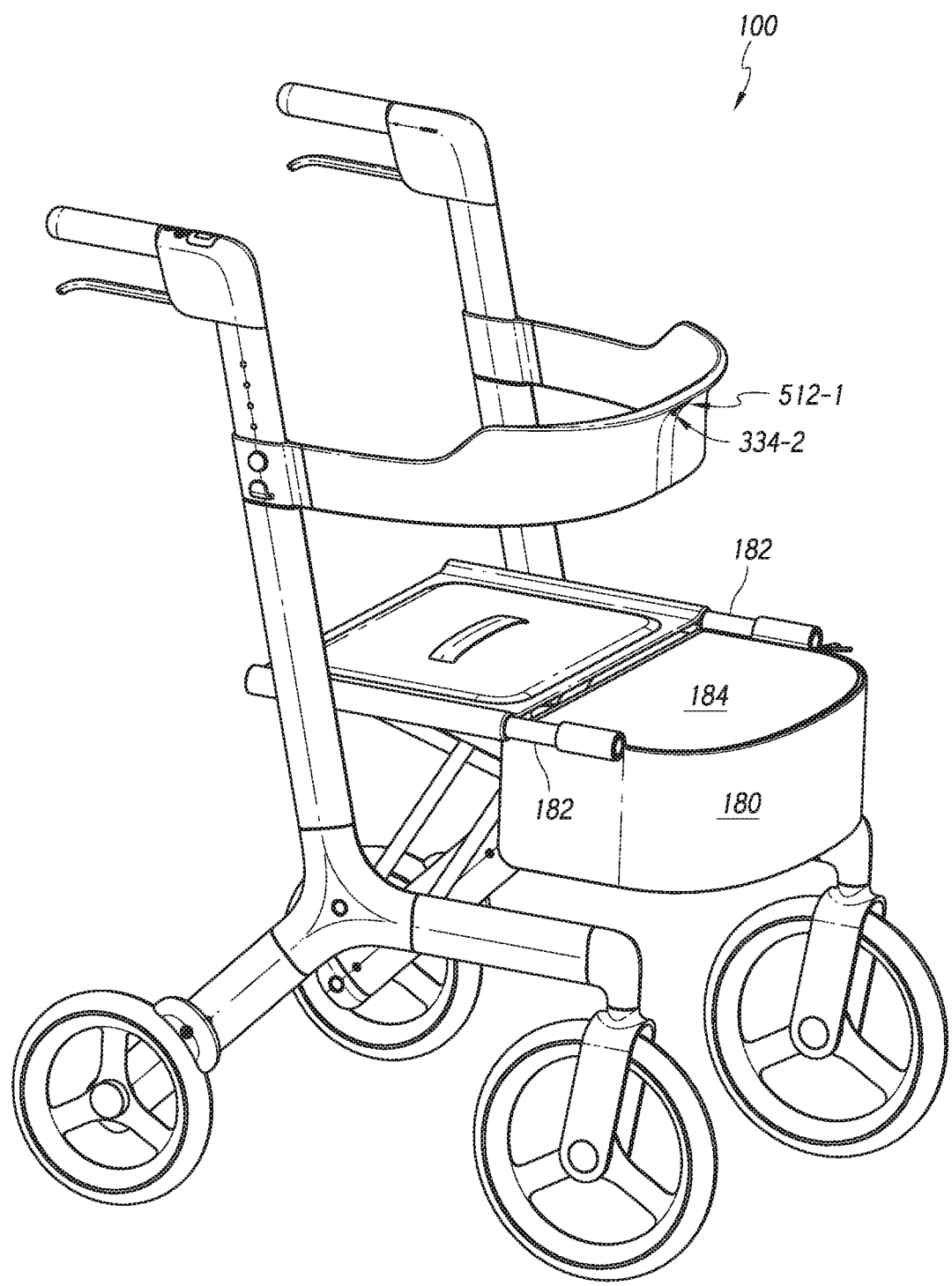
FIGS. 6A and 6B show front isometric view of a mobility aid device with a removable storage container, shown attached and detached, respectively, from the mobility aid device.
Figure 6B:
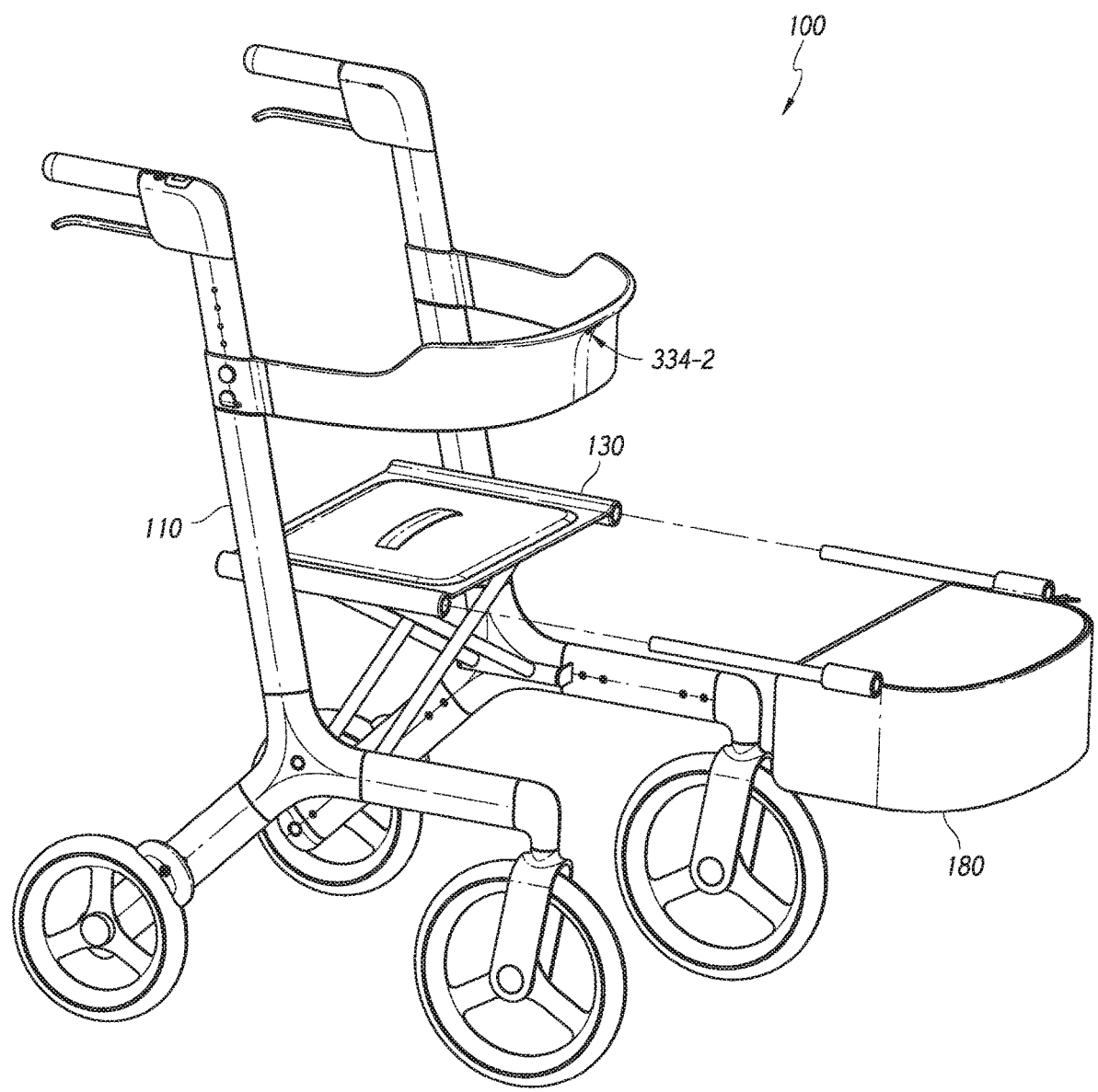
Figure 7:
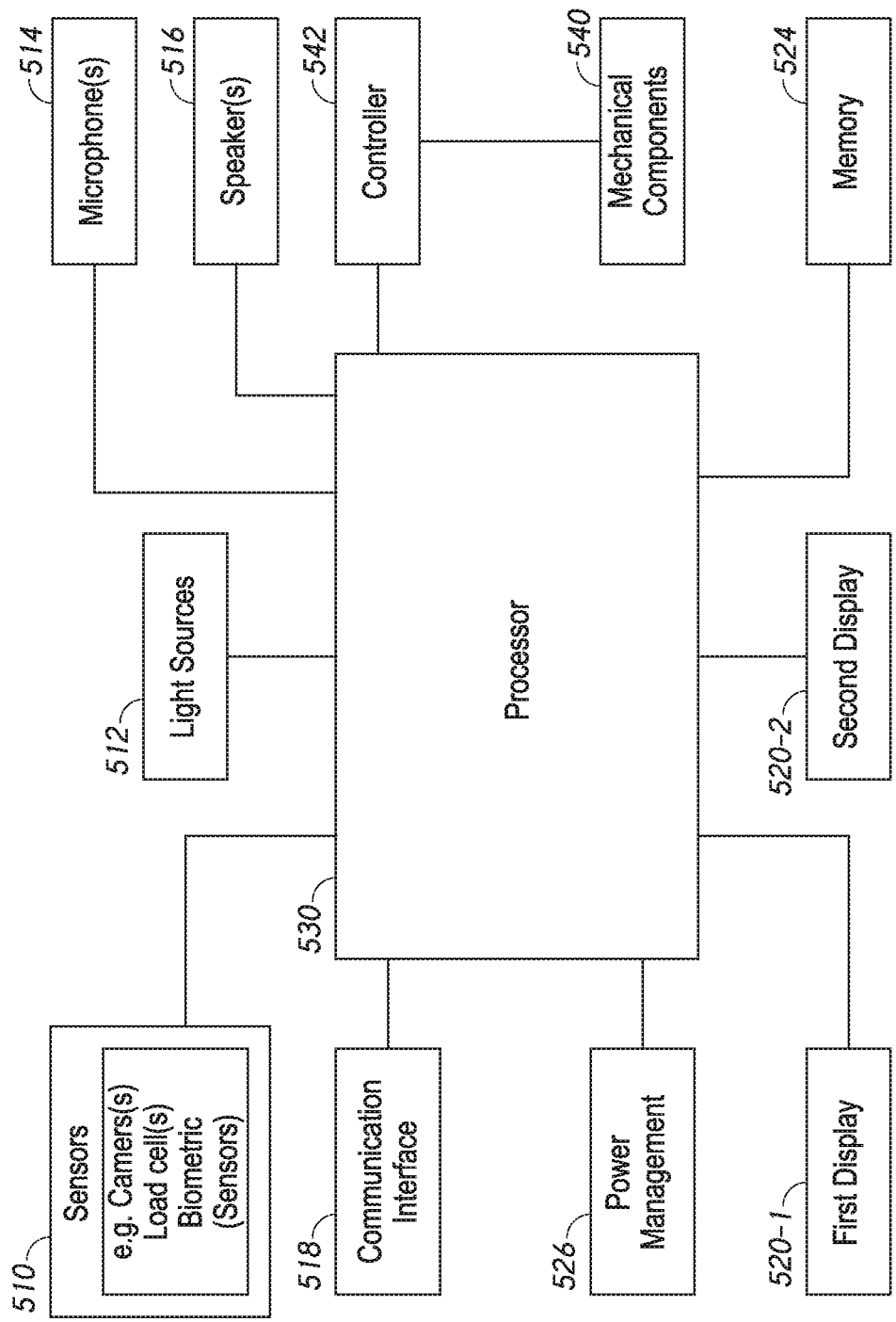
FIG. 7 shows a block diagram of an intelligence system of a smart mobility aid device according to the present disclosure.
Figure 8:
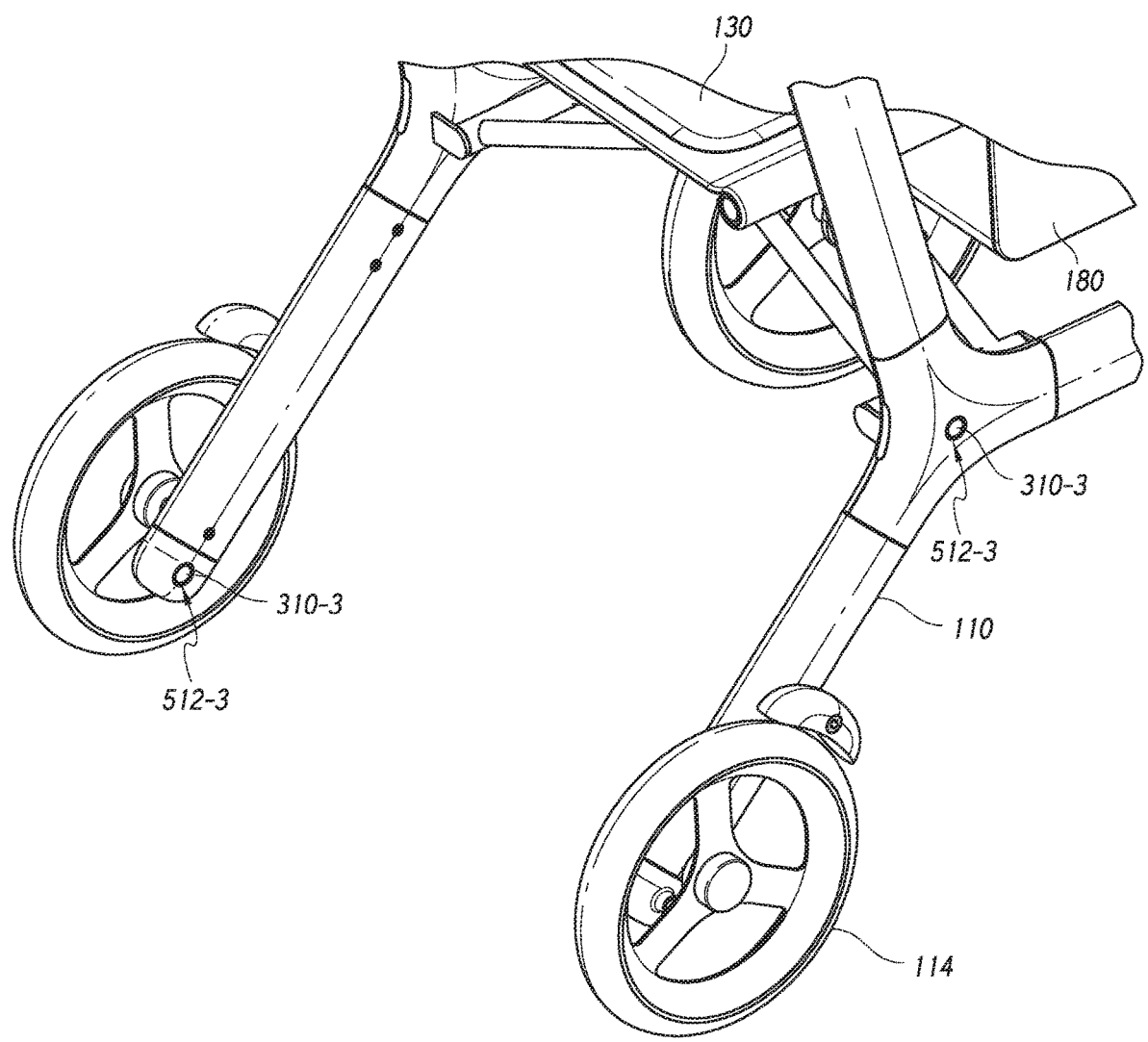
FIG. 8 shows a partial view of the base of a mobility aid device illustrating functionality of the smart mobility aid device including enhanced safety and connectivity features of the mobility aid device.
Figure 9:
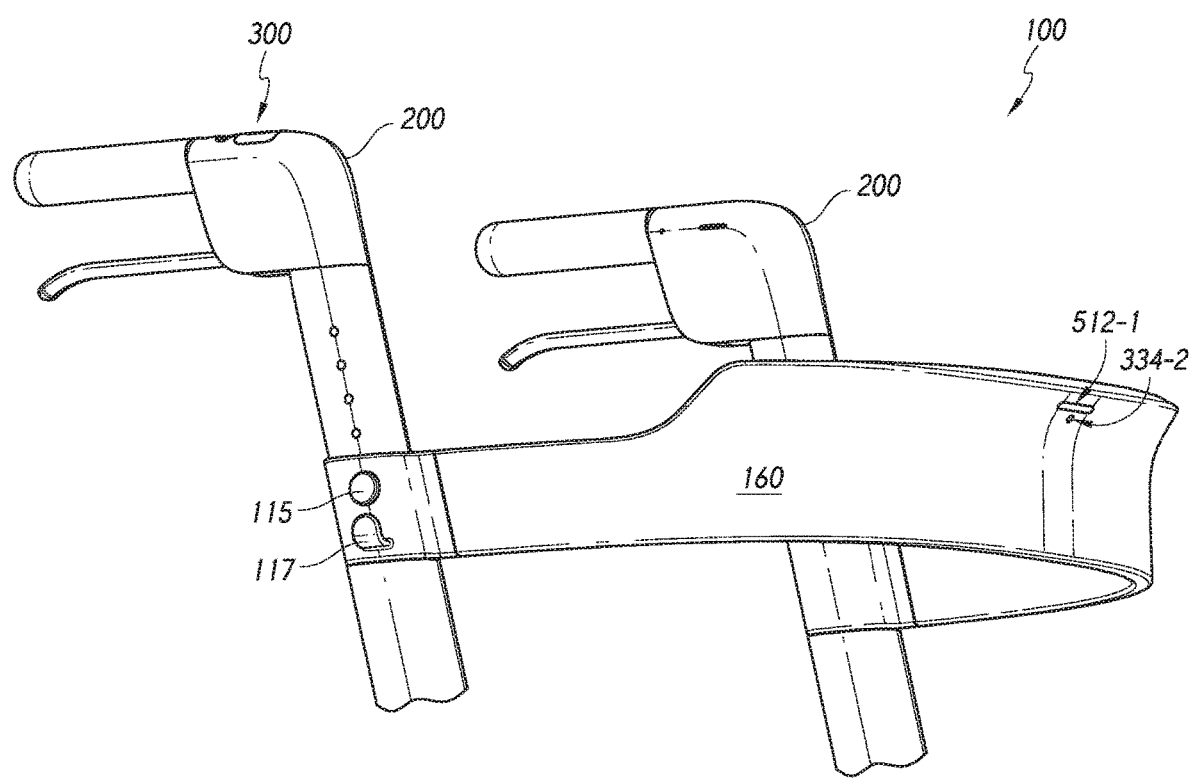
FIG. 9 shows a partial view of an upper portion of a mobility aid device including the backrest and illustrating functionality of the smart mobility aid device including enhanced safety, connectivity and adjustability features of the mobility aid device.

The mobility aid device 100 may be provided with a folding handle 192, which may in some cases be provided on the seat 130. In the example, in FIG. 3, the folding handle 192 is generally centrally positioned on the seat 130 to allow the user to grasp the folding handle 192 lifting the seat 130 away from the support surface. As the seat is lifted away from the support surface, the lower portion of the frame of the mobility aid device 100 pulls to the ground causing the folding linkage to scissor and fold the mobility aid device 100, e.g., as shown in FIG. 6B. As shown in FIG. 6B, the left and right frame portions are closer to one another than in the use configuration, thus the frame and correspondingly the whole mobility aid device 100 is provided in a more compact configuration. Components of the smart mobility device that may be frequently touched, such as the handle or components thereof (e.g., the grip portions and/or brake levers), the folding handle, and various touch sensors on the frame, may be provided with a self-cleaning feature (e.g., a UV cleaner, which may be embedded in the handle or in the charging apparatus for cleaning the mobility aid device while charging), which can be particularly useful in use cases where the same mobility aid device is shared among users, such as in a hospital or other care facility.

As further shown, e.g., in FIG. 2, the mobility aid device 100 may also include a backrest 160 and a storage container 180, each of which may be connected between the left and right frame portions. For example, the backrest 160 may connect the right frame portion to the left frame portion. The backrest 160 may be provided by any suitable structure positioned elevationally above the seat such as to provide support for the user's back when the user is seated. Thus, the backrest 160 may be ergonomically shaped to define a curve between the left and right frame portion. In some examples, the frame includes left and right frame portions arranged symmetrically on opposite sides of the seat, and a backrest extending between the left and right frame portions, and display built into the backrest. Similar to the seat, the backrest, or at least one or more portions thereof, may be formed of a relatively flexible material, which is easily flexible (e.g., without permanent deformation) to enable folding of the mobility aid device 100. Some of the enhanced functionality of the smart mobility aid device (e.g., a display, camera, light source, microphone, or others) may be integrated into the backrest of the mobility aid device 100, as will be further described.

The mobility aid device 100 includes at least one handle 200 configured to be gripped by the user during use of the mobility aid device 100. In the case of a rollator or walker, the mobility aid device 100 preferably includes two handles 200, one for each of the left and right hands of the user. As described, the mobility aid device 100 may be a smart mobility device and may thus be equipped with electronics, at least some of which may be located in or proximate to the handle 200. In examples of mobility devices, which include more than one handle, such as in a walker, rollator, or a set of crutches, the electronics enabling enhanced functionality of the mobility aid device may be provided in only one of the two handles, with the other being essentially a "dumb" handle, that is a handle without any enhanced functionality associated with biometric monitoring, communications or display of data. In yet other examples, one of the pair of handles may be provided with limited functionality, such as biometrics monitoring, while the other handle may include the full functionality of the multi-functional mobility aid device and/or house the electronic components that enable the various smart functions of the mobility aid device, such as connectivity (e.g., external communication), display functions, processing of user data, etc.

In mobility aid devices of certain types, for example a rollator 101, a wheelchair or other mobility aid device with one or more wheels, the handle 200 may include a grip portion 210 and a brake lever 208. In other examples, the handle 200 may not be provided with a brake when the handle is on the end of a leg that is not equipped with a wheel, such as in the case of a walker, crutches or a cane. The grip portion 210 may extend from a handle housing 220 and may be configured to be gripped by the user. The handle housing 220 may enclose one or more of the electronic components (e.g., one or more sensors, a processor, at least a portion of the display, and other circuitry for implementing the enhanced functionality) of the mobility aid device 100.

The handle (e.g., handle 200 of mobility aid device 100 or handle 800 of the mobility aid device 700) may include one or more of the electronic components that provide the intelligence system of a smart mobility aid device according to the present disclosure. The processor may be communicatively coupled to one or more sensors operatively arranged on the frame to detect a change of condition. The smart mobility device may include a light source (e.g., lights 512-1 or 512-2 of the rollator 101 or light 804 of the mobility aid device 700) configured to operate in one of a plurality of illumination modes based on the change of condition. For example, the handle may include health-monitoring sensors, sensors that detect biometrics of the person using the mobility aid device, a grip detection sensor, a light sensor, a finger print sensor, a GPS component, a mobility aid device user health status indicator, a load cell, a strain gauge, a camera, a proximity sensor, or a touch sensor. For example, one or more of the above sensors may be configured to communicate sensor data to the processor, and the processor may be configured to generate a seated mode signal upon determination, based on the sensor data, that the user is seated on the seat. A seated mode signal may cause a display (e.g., the display 332-2) to power down responsive to the seated mode signal. The handle may include a main user interface of the device, although additional user interface components such as additional displays, emergency buttons, speakers, microphones and or indicator lights may be provided at other locations on the frame. Health-monitoring and biometric sensors may include but are not limited to sensors operatively arranged on the handle to monitor parameters associated with the user's health or biometrics (e.g., for user identification) while the user is using the mobility aid device such as sensors capable of measuring blood and/or heart-related information such as blood pressure, blood sugar, heart rate, oxygen level/rate, an ECG sensor (e.g., using a single or pair of electrodes, each in the respective handle in the case of two-handle mobility aid devices), fingerprint sensor, etc. A status indicator of the smart mobility device, e.g., in the form of a light, vibration or an audible sound, may be used to indicate a normal status of the user (e.g., a green light), or an emergency status (e.g., an elevated heart rate, low blood sugar, irregular ECG, etc.), for example via a different colored light (e.g., a red light), an audible alert or a vibration of a component of the mobility aid device such as the handle. An emergency status may also be used to initiate an emergency protocol of the mobility aid device such as automatically sending an emergency transmission (e.g., test or initiating a call for help) or providing a recommendation to the user to seek help.

The smart mobility aid device may be configured to use one or more of the above sensors and/or additional sensors to track user activity such as to help the user improve their health. For example, the smart mobility aid device may alternatively or additionally include one or more additional sensors selected from an accelerometer, a gyroscope, a MEMS magnetometer, a barometric pressure sensor, a temperature sensor, an IMU, or load cells, and the like. The sensor data recorded by any of the sensors of the smart mobility device may be coupled to a processor (e.g., processor 530) which may be configured (e.g., via rule-based or machine-learning algorithms) to analyze the sensor data and extract information about the user's activity and health trends.

In some embodiments, electronic components associated with the intelligence system of a smart mobility device (e.g., the one or more sensors, processor, memory and/or external communication interface) may alternatively or additionally be provided elsewhere on the frame. For example, the electronics for a smart mobility aid device may be provided in the base (e.g., removable tip) of a mobility aid device, which may enable a conventional (e.g., "dumb") mobility aid device such as a cane or a crutch to be retrofitted with a "smart" base and thus reconfigured into a smart mobility device. While such reconfiguration may not provide the reconfigured mobility aid device with a display, the display function may be provided by the user's mobile phone or other smart wearable device, such as a smart watch a fitness tracker or the like. As described, the intelligence system of a smart mobility device of the present disclosure may be equipped with an external communication interface using one or a plurality of different types of electronic communication components) to enable communicatively coupling the smart mobility device to other electronic devices.

As shown, e.g., in FIGS. 1 and 8A-8B, the mobility aid device 100 may include a storage container 180, which in some cases may be removably coupled to the frame 110, so as to provide the mobility aid device 100 with a modular storage capability. The modular storage capability may enable the user to quickly and easily re-configure the storage area of the mobility aid device 100 for different use cases. For example, a storage container having different properties, such as being made from different fabrics, having different sizes or durability, and/or in some cases having integrated cooling (e.g., for storing groceries or other items that may require cooling or maintaining a cooler temperature than the ambient temperature), may be configured to be interchangeably removably attachable to the frame for easily changing the functionality and/or aesthetics of the mobility aid device 100. The removable storage container 180 may be attachable to and detachable from the frame 110 using any suitable mechanical or electro-mechanical mechanism. For example, the storage container 180 may be fixed to a set of elongate members (e.g., left and right posts 182), each of which is removably insertable into a respective passage in the seat frame. Different attachment mechanisms, additionally or alternatively including rails, hooks, mechanical or magnetic latches or other types of locking mechanisms, may be used to secure the storage container to the frame. For example, the folding linkage may removably support the storage container. In some examples, the seat is coupled to the frame using left and right bars extending from the left and right frame portions, respectively, and the storage container is silidably coupled to the left and right bars. The storage container may be provided with a cover 184, which may be partially or fully removable (e.g., via a zipper, buttons, Velcro, etc.) to expose the interior of the storage container 180. At least a portion of the storage container 180, for example a middle portion, may be flexible to accommodate the folding of the mobility aid device 100. In other examples, when the device is utilized with a generally rigid storage container, the storage container 180 may be removed before folding the mobility aid device 100.

As described, a mobility aid device according to the present disclosure (e.g., rollator 101) may have enhanced capability in that the mobility aid device may provide a variety of additional functions beyond simply mobility assistance. To that end, the mobility aid device, also referred to as a smart mobility device, according to any embodiment in the present disclosure may include an intelligence system 500, described now further with reference also to FIG. 5. The intelligence system 500 maybe configured to record data (e.g., sensor data), which may be used to monitor the user's activities, which may be used for detecting emergency conditions (e.g., a fall of the user). The intelligence system 500 may include one or more electronic components (e.g., sensors, a processor, memory, etc.) iintegrated into the mobility aid device 100 to provide one or more of the additional functions of the mobility aid device 100. For example, as shown in FIG. 5, the intelligence system 500 may include the one or more sensors 510, such as one or more cameras, motion and/or acceleration sensors (e.g., accelerometers and/or inertial measurement units (IMUs), proximity sensors (e.g., an optical proximity sensor), touch sensors (e.g., capacitive, resistance, or piezo switches and/or pressure sensitive capacitive sensors, etc.), load or pressure sensors (e.g., a load cell), and/or other types of sensors, one or more of which may be configured as biometric sensors. The intelligence system 500 may also include one or more light sources 512, microphones 514, speakers 516 and/or other feedback devices. The system may also include one or more displays (e.g., first and second display 520-1 and 520-2), non-volatile memory 524, an external communication interface 518, and a processor 530 in communication with the various electronics for controlling or performing the functions of the intelligence system 500. While the processor 530 is illustrated, in block diagram form as a single component, it will be understood that multiple processor circuits may be used to implement the various computational and/or control functions of the processor 530. The processor 530 may be implemented using any suitable combination of hardware and software components. The processor 530, which may be implemented as a single or a plurality of operatively arranged integrated processing circuits (e.g., CPUs, GPUs), application-specific integrated circuits (ASICs), microcontrollers, or any combination thereof, may include or be communicatively coupled to one or more additional controllers 542 configured to drive mechanical components 540 of the system 500, such as brakes, rotational drives, pumps or others as may be used for autonomous operation of the mobility aid device 100, or for other functions). The processor 530 may also be in communication with a power management component 526, such as for automatic powering up and down of the various electronic components, as described herein.

The mobility aid device 100 may include an audio system including at least one speaker integrated into the mobility aid device 100, which may be activated during a voice call and/or for audio playback. The intelligence system 500 of the mobility aid device may also include an external communication interface 518, which may be implemented using any suitable electronic communication component such as Bluetooth, ZigBee, WiFi, or a cellular (e.g., 4G, 5G, LTE) communication component, or any other suitable wireless communication link currently known or later developed. The mobility aid device 100 may utilize the external communication interface 518 for various functions such as to transmit data (e.g., user activity data) recorded by the device to an external computing device (e.g., the user's or a caregiver's laptop, cellphone, or other electronic device), to receive data such as to stream audio from a service provided, to place phone calls and/or send text messages, and others. The external communication interface 518 may be configured for establishing a link between the mobility aid device 100 and other wireless communication enabled devices of the user, such as the user's hearing aid, cell phone, etc. in which scenarios, the mobility aid device 100 may function as an intermediate node in the network of connected user devices. For example, the mobility aid device 100 may be configured to receive streamed audio (e.g., from a service provider or during a phone call) and either playback the audio (via the speakers of the device) or transmit the audio to the user's hearing aid, which can be based upon a user preference and/or the toggling of a switch on the device. To preserve the small form factor of the mobility aid device and still enable communication via a plurality of different methods (e.g., Bluetooth, ZigBee, WiFi and/or cellular), one of the handles may include an electronic communication component of a first type (e.g., a Bluetooth or a WiFi communication component), while the other handle may include an electronic communication component of a second different type (e.g., a WiFi or a cellular communication component).

As described, the mobility aid device 100 (e.g., rollator 101) may be configured to detect a fall of the user. The processor 530 may use sensor data from one or more of the sensors 510 embedded into the mobility aid device 100 to determine whether the user has fallen. For example, the mobility aid device 100 may include a sensor near the base to detect a fall of the user, and the processor may be configured to generate an emergency transmission signal responsive to a detected fall. For example, the processor 530 may be configured to receive image data from at least one camera, which has a field of view including an area around the base of the mobility aid device 100, and the processor 530 may analyze the image data (e.g., using any suitable image processing technique such as image segmentation and/or an appropriately trained machine-learning model) to identify an object near the base of the mobility aid device 100 that could indicate that the user has fallen (e.g., an object matching a portion of a person's upper body, which in normal circumstances would not be located near the base of the mobility aid device 100). In some examples, the processor may perform image data analysis for fall detection only when the processor fails to detect contact of the user with the device, such as lack of touch or force being applied to the handles, to the frame or the seat. The mobility aid device may utilize any number of operatively arranged cameras, including a rear-facing, a forward-facing, or peripherally facing cameras for image data collection.

In some examples, a mobility aid device (e.g., the rollator 101, a smart wheelchair, or the mobility aid device 700) may include passive fall detection components. For example, a mobility aid device may contain an emitter that emits a radio frequency signal and receives and analyzes backscattered energy from that signal. Such components may be able to detect a user's fall even when the user is not in contact with or in close proximity to the mobility aid device. For example, a mobility aid device may include an Ultra Wide Band (UWB) radio emitter and detector and/or a Frequency Modulated Continuous Wave (FMCW) continuous wave radar backscatter emitter and detector configured to detect a fall of a user. Illustrative examples of such components include the fall detection sensor by Totemic Labs, Inc., as described for example in U.S. Pat. No. 10,617,330, or the device by Vayyar Imaging Ltd., as described for example in International Patent Pub. No. WO 2020/008458.

The image data from the camera(s) may alternatively or additionally be used by the processor 530 for other functions, such as to identify a user in a multi-user setting (e.g., when the same mobility aid device may be used by different users such as in a hospital or elderly care facility). For example, the processor of the smart mobility device may be configured to identify the user based on image data captured by a camera, (e.g., rear-facing camera 334-1) and unlock the smart mobility device for use upon identification of an authorized user. Responsive to identification of the user, the system 500 may unlock the mobility aid device 100 for use (e.g., by unlocking the brakes and/or unlocking the electronic features of the device) and retrieve and applying user-specific settings for the mobility aid device 100, such as illumination level settings, volume settings, emergency contacts, autonomous control parameters (e.g., speed, braking force level, etc.). For example, the processor may be configured to automatically apply user-specific settings to the smart mobility device based on recognizing an authorized user. In some such examples, the mobility aid device 100 may include at least one camera which is operatively arranged on the frame (e.g., positioned and/or oriented) to include in its field of view an area that is expected to include a portion of the user's upper body, particularly a portion that is expected to include the user's head, particularly when the user is positioned proximate the mobility aid device 100 with the user's hands generally in position to hold the handle(s). In some examples, instead of cameras, a different type of sensor, or a combination of sensors may be used to identify a user in proximity, or a specific user, and to unlock and/or apply user-specific settings. For example, a proximity sensor (e.g., in a suitable location in the frame or associated with the user interface 300) or touch sensor (e.g., in the grip portion 210 or associated with the user interface 300) may be used to detect a user in proximity or touching, respectively, the mobility aid device 100, responsive to which the intelligence system 500 may unlock the device for use. A variety of other sensors, alternative to a camera or in addition thereto, may be used to identify a specific user, such as biometric sensors (e.g., a fingerprint reader, which can be embedded into the grip portion or elsewhere on the handle, such as on a functional button that's part of the user interface 300).

The image data from the camera(s) may additionally or alternatively be used for deriving gait measurements. To that end, a rear-facing camera 334-1 may be operatively arranged on the frame (e.g., positioned and/or oriented) to include in its field of view an area that is expected to include a portion of the user's body (e.g., the lower body, the user's legs and/or feet). For example, the rear-facing camera 334-1 may be positioned to include feet of the user within the field of view of the rear-facing camera 334-1, and the processor may be configured to generate a stride length measurement based on a distance between the feet as detected by the rear-facing camera 334-1. The image data from such camera(s) may be processed by the processor 530 to extract a distance between the user's feet while walking, which may be averaged over a period of time and/or a plurality of steps, to generate a gait measurement (e.g., a gait length, gait speed, etc.). Short-term gait trends may be used to identify an emergency condition. For example, if the user's gait, analyzed over a short period of time such as during 5-10 minute intervals, shows variations of statistical significance, this may indicate that the user is experiencing loss of balance, which may be a precursor to a fall. An alert may be generated, which may be externally transmitted to a caregiver, and/or a suggestion may be provided (via voice or display) to the user to call for help. The gait measurements may be further analyzed by the processor 530 or an external device (e.g., on a longer-term basis, such as daily, weekly, or other periodic basis) for monitoring the user's health. As an example, a trend indicating a narrowing of the user's gait may indicate declining health, while a steady or increasing gait length may indicate a stable or improving lower body strength of a user and thus consistent or improving health. Gait measurements may be obtained from other sensor data, alternatively or additionally to image data from the camera(s). For example, other sensors, such as load cells, pressure sensors, accelerometers, IMUs, rotation sensors associated with a wheel, etc., may be used to identify a gait or step cadence. For example, a smart mobility device may include a sensor operatively associated with a wheel of the plurality of wheels to measure rotation of the respective wheel, and the processor may be configured to generate a gait measurement based on the measured rotation. The cadence may be used, in combination with distance traveled, such as may be obtained from sensors that monitor rotation of the wheels (e.g., rotary position or revolution count sensors, like Hall effect or optical interrupt sensors), or from a GPS or other geolocation sensor that more globally monitors distance traveled, to derive a gait measurement (e.g., by dividing the distance traveled by the number of steps to determine a distance per step, and thus obtain a gait length or gait speed measurement).

In some examples, the smart mobility device can capture other data related to the user's physical movement or position and can use that data as a basis of other indications of user health. For example, a camera of the smart mobility device may be used capture posture data of the user. For example, the rear-facing camera 334-1 can capture image data including a portion of the user's body (e.g., an upper portion of the user's body. to the processor can generate a posture measurement based on image data captured by the rear-facing camera 334-1. The processor can use posture data as an indication of the user's health and may develop trends of posture over time which may indicate improving or declining user health.

In some examples, the camera(s) and/or other types of sensors (e.g., a proximity sensor) may be used for obstacle detection. Particularly in scenarios when the mobility aid device 100 is used with a storage container 180, a significant portion of the area in front of the device may be blocked from view, thus obstacle detection and avoidance or alerting by the mobility aid device 100 may be advantageous. For example, a forward-facing camera 334-1 may be operatively arranged on the frame (e.g., positioned and/or oriented) to include in its field of view an area in front of the device and in some cases, specifically focusing the view ahead of the base of the device. Image data processing, as described above, can be used to detect objects in the path of the rollator 101. In the case of autonomous or semi-autonomous rolling of the rollator 101, the object detection may be used for steering for obstacle avoidance, in manual mode, the object detection may be used to provide an alert to the user. For example, a forward-facing camera 334-1 arranged on the frame for detecting obstacles in a path of the smart mobility device, may communitive to the processor configured to generate a warning upon detection of an obstacle in the path of the smart mobility device.

The mobility aid device may be equipped with at least one emergency button 310, and in some examples a plurality of emergency buttons, which the user can activate to send a distress or emergency signal, such as if the user falls, feels in danger, or requires assistance. In the example rollator 101, at least one emergency button is provided in at least one of the handles, in this example in the right handle but in other cases, the button may be in the left handle, or an emergency button may be provided on both handles, which can be useful if one of the user's hands is injured or has reduced dexterity. In yet other examples, one or more additional emergency buttons may be provided elsewhere on the device, such as peripherally on the frame (e.g., at the frame junctions 113), near or integrated into one or more of the wheels, etc. While the term button is used to refer to component 310, it will be understood that the button may be physical/mechanical button, or a soft control or button, such as one implemented by a touch sensor (e.g., capacitive, pressure, pressure-sensitive capacitive, or other suitable touch sensors) programmed to effect the function associated with the emergency button responsive to a detected touch.

In some examples, the mobility aid device may include one or more touch sensors embedded at various locations on the frame, and programmed such that when touched by the user, they invoke a particular response such as indicating an emergency condition. Different touch sensors may be differently configured. For example, touch sensors located near the handles may be programmed (e.g., by the user or caregiver) to invoke non-emergency functions such as turning on a light, while touch sensors near the base may be programmed to invoke emergency functions, such as initiation an emergency transmission (e.g., a text message, a call) and/or activating emergency lighting of the device. In some examples, an emergency function such as an emergency transmission may require user verification, for example via voice command. In other words, a touch of the emergency button or other emergency touch sensor may activate an appropriately located microphone (e.g., a microphone near the button/touch sensor engaged by the user) to receive the appropriate voice command, such that an emergency transmission may not be initiated until a confirmation is received via the microphone. In some examples, the user may need to follow a voice prompt and provide commands to the mobility aid device 100 via the microphone. Upon confirmation of the emergency condition (e.g., a fall of the user), the device may engage the pre-programmed emergency protocol for the specific emergency condition, e.g., activate its sound system, which may include a combination of microphone(s) and/or speakers, to alert other users and seek help, activate emergency lighting, initiate an emergency transmission via the electronic communication component, etc. In some embodiments, the mobility aid device may be configured to automatically activate one or more microphones of the mobility aid device upon detection of an emergency condition such as a fall and may be further configured, upon detection of the user's voice via the microphone, to automatically initiate an emergency transmission (e.g., a voice call based on the audible information detected via the microphone, a text message of the audible information detected by the microphone, etc.). For example, the mobility aid device 100 may include a plurality of microphones including a first microphone located elevationally closer to the handle than a second microphone located elevationally closer to the plurality of wheels, and the second microphone may be automatically activated upon detection of a fall.

A mobility aid device (e.g., the rollator 101 or the mobility aid device 700 described below) may use a microphone to capture voice commands from the user to activate or de-activate any of the functions of the respective devices. For example, the rollator 101 or a wheelchair may take voice commands to control brakes, rotational drives, pumps or other components as may be used for autonomous operation of the mobility aid device 100. For example, the rollator 101 could respond to spoken command such as "stop", "left", "right", "back", faster", "slower", or the like by taking the corresponding action. A mobility aid device may take voice commands related to making a phone call or performing speech-to-text functions such as drafting a text message, email, or other communication. A mobility aid device may take voice commands to initiate an emergency response. The mobility aid device may take voice commands to control the playback of media, such a responding to commands such as "louder", "quieter", "next song", "last song" or the like.

As described, the mobility aid device 100 may be configured to detect a fall of the user, and in such cases, the mobility aid device 100 may be configured to automatically trigger the distress or emergency signal, which may involve the transmission of a message (e.g., text message), the initiation of a call to emergency response and/or another designated person (e.g., a caregiver), the sounding of an audible alarm, activation or lights, or any combination thereof. In some embodiments, the mobility aid device may include a plurality of user interface components at various locations of the mobility aid device (e.g., near the top or handles of the mobility aid device, near the bottom or base of the mobility aid device), and the mobility aid device may be configured to intelligently power up or activate an appropriate user interface component based on the detected condition, such as by activating a microphone, speaker or emergency button near the base of the mobility aid device upon detecting that the user has fallen. For example, the mobility aid device 100 may include a plurality of speakers including a first speaker located elevationally closer to the handle than a second speaker located elevationally closer to the plurality of wheels, and the second speaker may be configured to automatically activate upon detection of the fall. In some cases, the mobility aid device 100 may be configured for a tiered response, where certain non-normal conditions (e.g., a true emergency like a fall) triggers an automated response, while other non-normal conditions (e.g., a predicted emergency condition, such as if the mobility aid device detects the user or the mobility aid device is unstable based on the sensor data, the user is overexerted, overheated, dehydrated, or likely to lose balance), a near-emergency or distress response may be triggered, where the mobility aid device may suggest to the user to press the emergency button (e.g., by illuminating it in a steady or flashing manner) but may not automatically activate the emergency protocol.

In some instances, if an emergency or distress condition is detected, the intelligence system of the mobility aid device 100 may provide additional or different responses, tailored to the specific scenario. For example, and as previously described, the mobility aid device may be equipped with a plurality of microphones at various locations, such as at elevationally lower locations (e.g., near the base, such as near or embedded in the wheels), and elevationally higher locations (e.g., near the upper part of the frame, such as near or integrated into the handles). One or more of the microphones may be automatically and intelligently activated upon the detection of an emergency condition such as a fall. For example, if a fall is detected, the system may activate the microphone nearest the fallen user. In some cases, a plurality of microphones closest to the user may be activated to enhance the likelihood of the user being heard on the other side of the call. One or more of the microphones may additionally or alternatively be configured for manual activation. For example, a microphone built into the handle may be configured to be manually activated, while any of the microphones located elevationally lower than the handle may be configured primarily for automatic activation. The manual vs. automatic activation of microphones may be controllable by the user and stored into memory 524 as a user preference or setting.

The mobility aid device 100 may include at least one light source, which may function as a flash light, and in some embodiments, a plurality of light sources may be arranged on the mobility aid device to serve a variety of functions. As shown also in FIG. 9, the mobility aid device 100 may include a light source (e.g., light 512-1) on a forward facing part of the mobility aid device 100, for example on the forward-facing side of the backrest, on a forward-facing side of the handles or the frame, or other suitable location. In some examples, one or more of the light sources may be manually activated by a light switch (e.g., switch 320, which can be a mechanical button or switch or a soft control, such as a touch sensor). A single light switch may activate all of the lights sources (forward-facing and rear-facing), or independent switches e.g., one on one handle and one on the other or both co-located on the same handle) may be provided for different ones of the lights. The switch may also be operable to toggle among different light settings (e.g., different levels of illumination being provided by the light sources at different settings), and toggle to an OFF setting, which can be used to turn off the lights, irrespective of whether operating in a normal mode or emergency mode.

The light source may be operatively associated with a sensor configured to detect ambient light conditions. The light source may be configured to activate automatically upon detection of low light conditions, for example corresponding to light conditions at dawn, dusk, evenings and nights, and/or dim indoor lighting conditions. In some examples, the sensitivity of the ambient light sensor may be configurable by the user to allow the user to increase or decrease the level of lighting that triggers automated activation of the light source, such as to enhance the user's visibility when using the mobility aid device or preserve battery power, when ambient lighting is sufficient. In some examples, the light source may be operatively associated with a controller that automatically activates the light source based on location or time of day, in addition to or alternatively to ambient light conditions. The time of day and/or location that triggers activation of the light source may be programmed by the user, and in some cases associated with the user's profile such that when a particular user is identified as using the mobility aid device 100, the appropriate user settings are automatically invoked. In yet other examples, the lights may not turn on automatically but the ambient light sensor and/or user settings may instead trigger an alert to be automatically generated to remind or suggest to the user to turn on the lights, which alert may be displayed on any one of the displays and/or provided via a different feedback mechanism (e.g., a voice alert).

As described, a plurality of lights sources may be located on the mobility aid device (e.g., operatively arranged at various locations around the frame) for providing a variety of functions including for enhancing the user's visibility of his or her surroundings (e.g., functioning as a flash light) and/or making the mobility aid device and thus the user more visible to others. As another example, one or more light sources 512-2 may be located on a rear-facing part of the mobility aid device, such as embedded into or otherwise coupled to the rear-facing sides of the left and right frame portions, a rear-facing portion of the seat frame (e.g., at the ends 144 of the bars 146), or other suitable location. The rear-facing lights may be used for visibility (e.g., to enhance the visibility of the mobility aid device, and thus its user, to others, including cars, pedestrians, etc.). Any of the light sources of the mobility aid device may also provide an alert function. For example, one or more of the forward-facing light sources (e.g., light 512-1), rear-facing light sources (e.g., lights 512-2), or other light sources arranged around the frame of the mobility aid device (e.g., 512-3) may be configured to operate at different frequencies or illuminate in different colors. For example, a light may be configured to operate at a first frequency or have a first illumination color when an emergency condition has been detected and to operate at a second frequency or have a second illumination color when no emergency condition has been detected. For example, the light sources may flash (turn on and off intermittently) at a lower frequency in normal conditions, such as when the user is walking. The light sources may be configured to automatically switch to a higher frequency of flashing upon detection of an emergency condition. In some scenarios, the light subsystem may be configured to activate more sources of light as ambient light decreases and/or upon detection of an emergency condition. In the case of the latter, the frequency and/or color of the lights (e.g., changing from yellow/white to red or orange, or for rear-facing lights changing from a red to orange or remaining at red but flashing at different frequency) may automatically change upon the detection of the emergency condition. As illustrated, the light sources may be arranged at various suitable locations around the frame, e.g., as shown by lights 512-3, which are embedded at the frame junction components 113 of each of the left and right frame portions 110-1 and 110-2, on the wheels and/or the wheels' rims, on the seat or storage container frames, handles, etc. In yet further examples, the lights may be configured to illuminate in different patterns based upon the condition. For example, in normal condition, lights may illuminate in an alternating pattern between the lower and upper positioned lights (e.g., illuminating the lower lights while turning off the upper ones, then switching to the upper and turning off the lower, and then repeating). In an emergency condition, as an example, the lights may be illuminated in a pattern such that they appear to circle around the frame, similar to an emergency rotating light. A variety of other suitable patterns may be used to indicate the change in condition. In addition, one or more of the light sources (e.g., light 512-3) may be integrated with other intelligence system components (e.g., with a respective button 310-3, microphone and/or other user interface components located peripherally on the frame and separated from the main interface on the handle). As such, the lights 512-3 may also serve to illuminate to the user other controllable locations on the mobility aid device, e.g., for making an emergency transmission (e.g., for sending a text or initiating a phone call) or for speaking into the microphone/audio system of the mobility aid device. In yet further embodiments, the light sources associated with peripheral interface (e.g., communication) components may be configured to pulse or otherwise indicate to the user that they are receiving input (e.g., voice input) from the user, which can provide a piece of mind for a user that may have fallen and needs some assurance that his or her distress call is being heard.

A mobility aid device according to the present disclosure (e.g., rollator 101 or the mobility aid device 700 described below) may include one or more biometric sensors, which can be used for user identification, for measuring biological information and/or tracking user activity. As described above, one or more biometric sensors may be used to automatically identify a user when the user makes contact with the mobility aid device to unlock the mobility aid device for use. A mobility aid device may include a sensor configured to measure biometric data associated with the user, and a memory for storing the biometric data onboard the smart mobility device. In addition, heart rate, ECG, blood pressure, oxygen level, hydration level, temperature, grip force, and pressure or weight applied to the handles/frame of the mobility aid device and other biological information may be measured, recorded, and in some cases used to derive information about the user's health. Heart related measurements (e.g., heart rate) may be measured, while the user is gripping the handle, using a plate sensor, an optical sensor, or other suitable sensor positioned on any suitable side of the handle such as on the top or bottom side of the handle. Biological information, in some cases may be used in combination with user identification data (e.g., a fingerprint scan, picture or the like) or in some cases in place of user identification data to identify the user and unlock the mobility aid device. For example, a measured heart rate, grip strength or grip configuration or mechanics, pressure/weigh applied to the mobility aid device, or any suitable combination of biological measurements may be used by the processor for identifying the user by matching the measurements to stored information about authorized users (e.g., of stored user profiles). Measured and/or derived biological information may be stored onboard the mobility aid device 100 (e.g., in a memory 524) and in some cases transmitted to an external device, such as a computing device of the user, a caregiver or healthcare provider. For example, a smart mobility device (e.g., rollator 101 or the mobility aid device 700) may include an electronic communication component configured to communicatively couple the smart mobility device to an external computing device, and the electronic communication component may automatically, periodically transmit information about the user to the external computing device. In some examples, the memory 524 may include a removable component, such as an SD card, a flash drive, or other removable data storage device. In yet other examples, a SIM card may provide at least a portion of the memory 524. Whether the processor stores the recorded and derived information locally or remotely may be a setting controlled by the user (and stored as a user setting), such as programming a periodicity for automatic upload of user data onto an external storage device. In scenarios in which the same mobility aid device is shared among multiple users, the upload of user activity data and/or biological information may occur automatically when the mobility aid device no longer detects that the user is using the mobility aid device.

Figure 10:
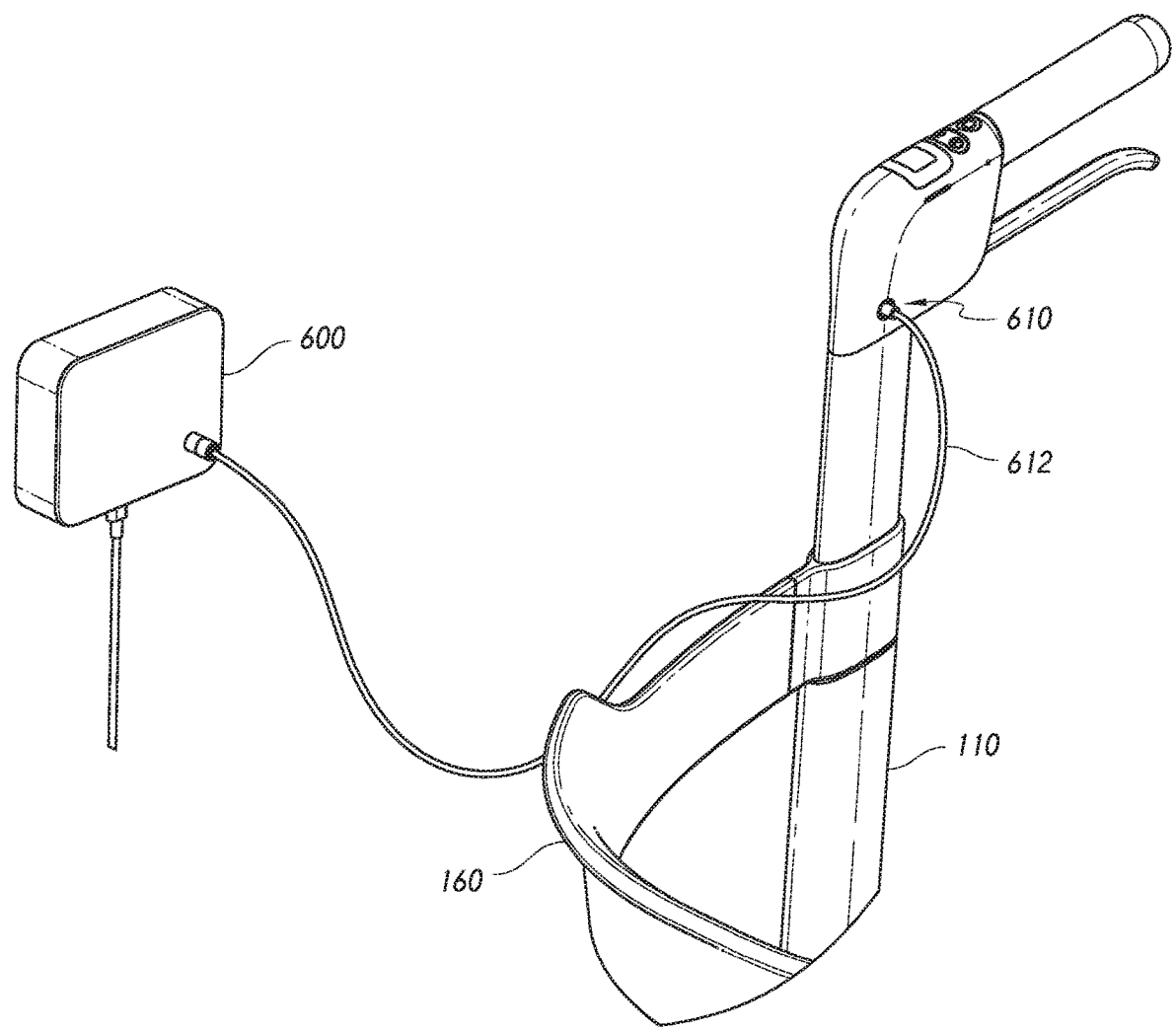
FIG. 10 shows a portion of the mobility aid device including a handle with electronic components of the mobility aid device and a charging assembly for the mobility aid device.
Figure 11:
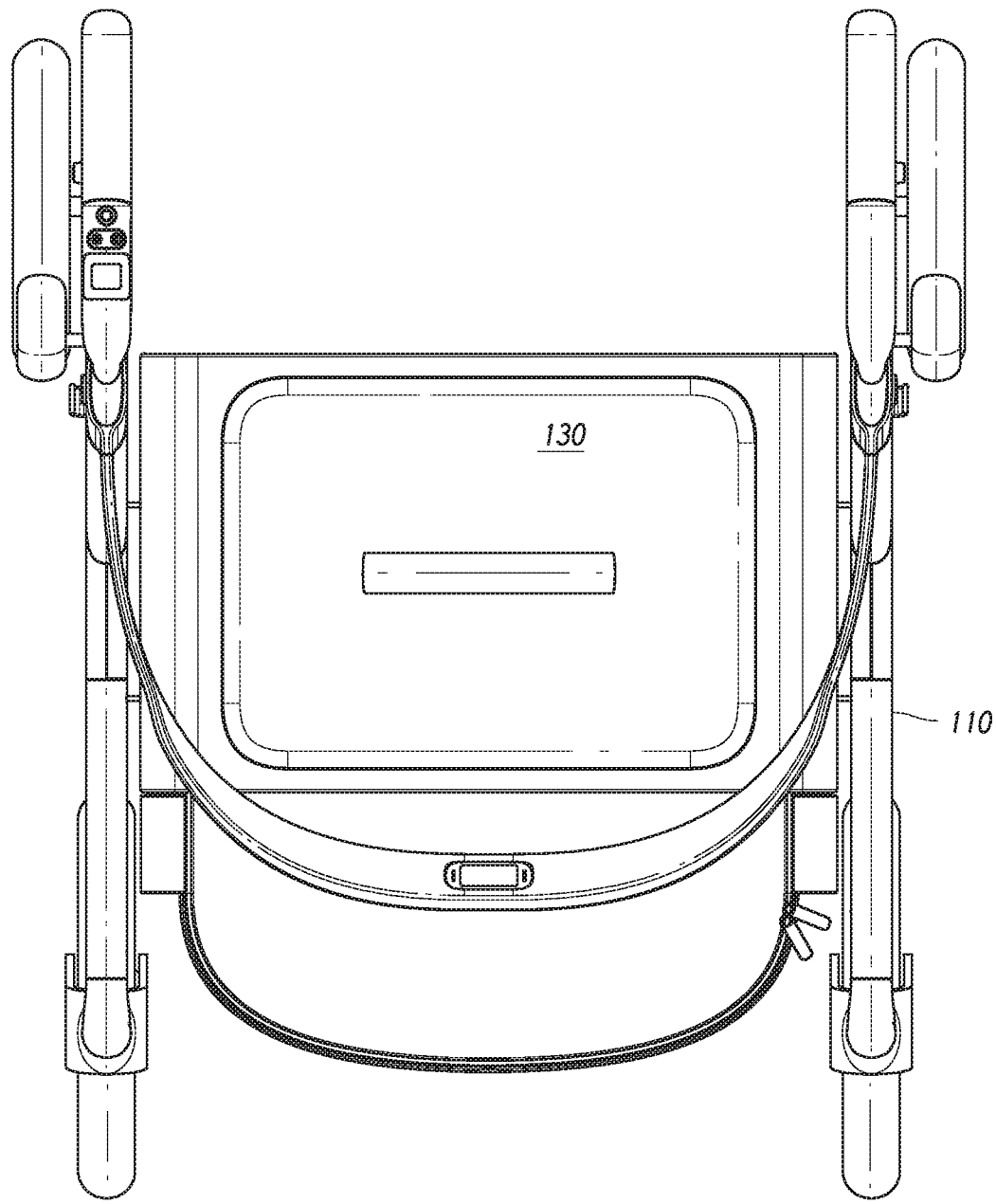
FIGS. 11 and 12 show a top and a bottom view, respectively of the mobility aid device of FIG. 1 showing additional functional and aesthetic elements.
Figure 12:
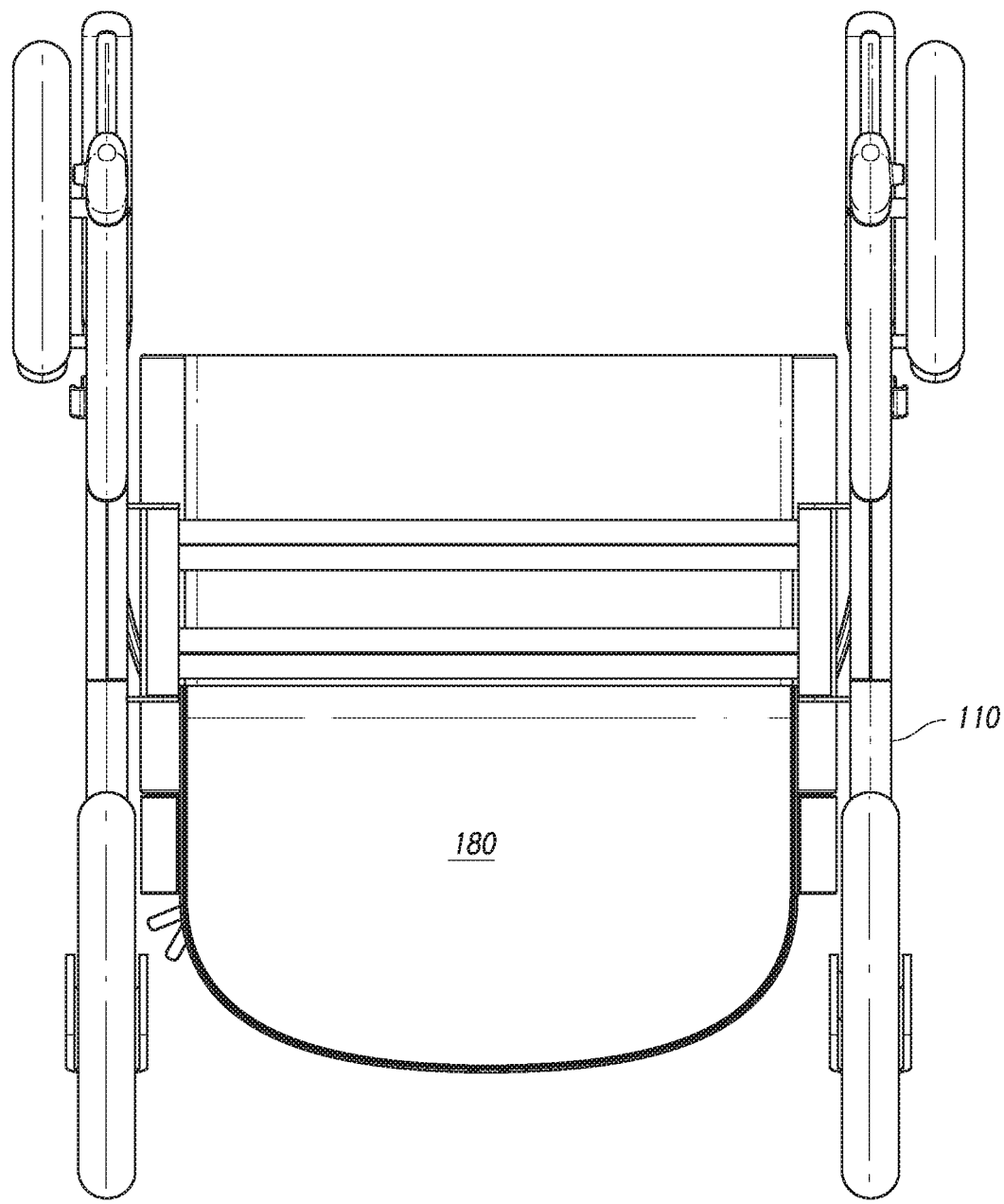

The mobility aid device (e.g., rollator 101) may be recharged by any suitable means. For example, as shown in FIG. 10, the mobility aid device 100 may be equipped with a power plug 610 for insertion of a charging cable 612, which is configured to draw power from an external power source 600. The power plug may be connected to the processor 530 and/or the power management circuit 526 for determining the amount of power to be drawn from the external power source to recharge the onboard power source (not shown). In the illustrated examples, the charging interface (e.g., power plug 610) is located on the handle. This configuration may be particularly well suited for embodiments in which most of the electronics including the processor are located in the handle. This configuration may also provide for an ergonomic placement of the charging interface as a location conveniently positioned for the user (e.g., so as to not require the user to bend down to plug the mobility aid device into power). However, it will be appreciated that the charging interface may, in other examples, be located elsewhere, such as near the base of the mobility aid device. In some examples, the mobility aid device may be wirelessly charged, for example via inductive charging through one or more coils operatively arranged on the frame 110. For example, the mobility aid device may be placed on a charging mat and use wireless power transfer between the mat and coils in the wheels or at the base of the mobility aid device. In yet other examples, the coil(s) may be placed elsewhere such as within the frame components, in the backrest 160, the seat or elsewhere, and be configured to wirelessly re-charge the mobility aid device when the mobility aid device is positioned near a wireless charging unit, such as one mounted on a wall or otherwise positioned at the appropriate height to inductively couple to the coil(s) in the mobility aid device 100. Other charging mechanisms including but not limited to, wireless charging, inductive charging, and conductive charging, may be used. The mobility aid device 100 may utilize a re-chargeable battery or any suitable battery technology for on-board power. In some examples, the mobility aid device 100 may include a re-chargeable battery, such as a lithium ion battery. In some examples, the mobility aid device 100 may additionally or alternatively include a non-rechargeable battery (e.g., a back-up battery). In some cases, the back-up battery and/or the re-chargeable battery may be located in a compartment within the body of the mobility aid device, which is accessible (e.g., through an access port or cover) to the user for replacing the battery without having to replace the entire mobility aid device. In some examples, the battery may be integrated into a component less expensive to replace than the full mobility aid device, such as a removable base of the mobility aid device. The battery may also be located in a removable base in examples in which the intelligence system is implemented as a "smart" base for retrofitting a "dumb" mobility device.

In yet further examples, the mobility aid device 100 may be rechargeable through use (e.g., while the user is walking). The mobility aid device may include one or more energy harvesting devices, which convert, for example the rotary motion of the wheels into electrical energy. As described, in some examples, one or more of the wheels may be motorized (e.g., for autonomous or semi-autonomous assisted driving), and when the wheels are not being power for assisted driving, the motorization mechanism may operate in reverse to harvest power. The mobility aid device may include other energy harvesting devices. For example, a non-rollable mobility aid device may include a shock harvester or a swing harvester, which convert the kinetic energy of the various motions experienced by the mobility aid device into electrical energy, which is in turn used to recharge the battery of the mobility aid device 100.

Figure 13:
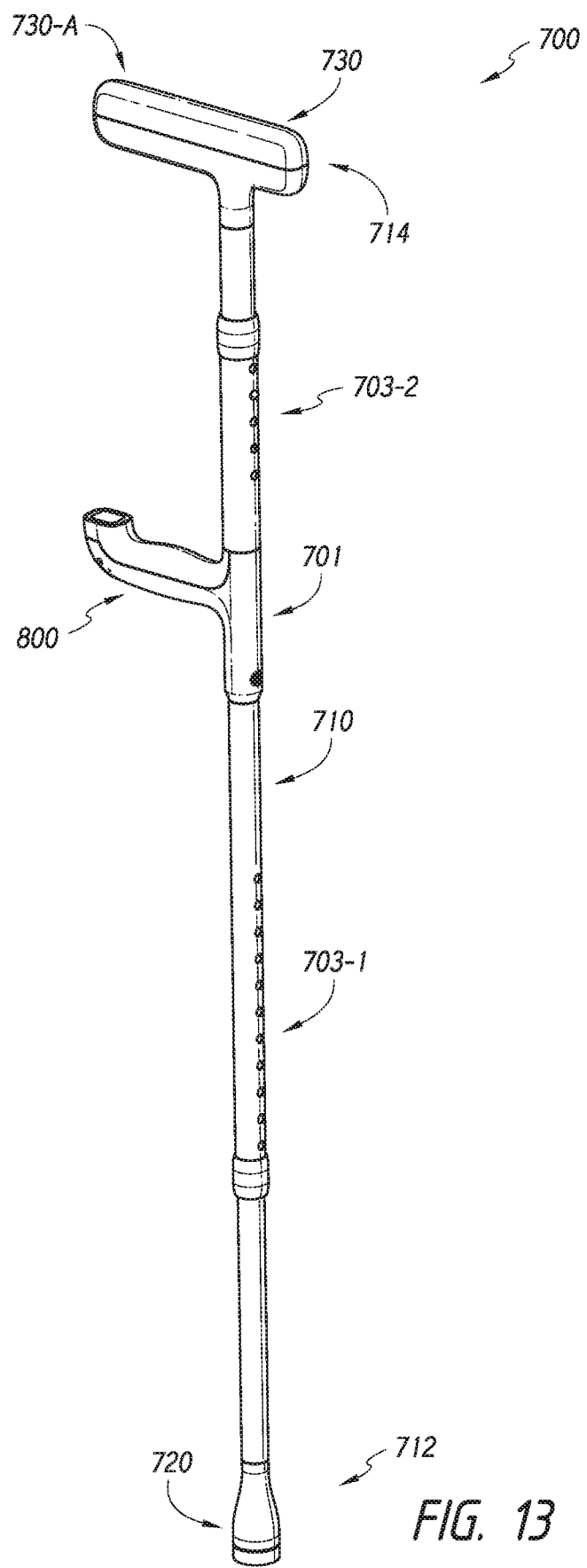
FIG. 13 shows an isometric view of a mobility aid device according to further examples of the present disclosure.

FIG. 13 shows a mobility aid device in accordance with further embodiments of the present disclosure. The mobility aid device 700 (or simply smart mobility device), shown in this example as a crutch 701, has a single leg provided by an elongate body 710. The body 710 can be implemented using one or more elongate tubular members. The body 710 has a first end and 712 a second end 714 that define a length therebetween. The length may be adjustable at one or a plurality of distinct locations on the body 710 (e.g., first adjustment location 703-1 below the handle 800 and second adjustment location 703-2 above the handle 800). For example, the length of the body may be adjustable, and the device includes a first adjustment portion of the body above the handle and a second adjustment portion of the body below the handle. A base 720, shown here as a single-foot tip, may be coupled to one end of the body. The base 720 may be of a different configuration in other embodiments, such as in the form of a multi-foot tip (e.g., a tripod tip). In some embodiments, the base 720 may be removably coupled and/or interchangeable with bases of different configurations, such as with a multi-foot tip. The mobility aid device may, in some cases, be provided to the user as a kit including a plurality of different bases for each leg, which in the case of crutches may be typically provided as a set of left and right crutches. In one example, the smart mobility device 700 includes a handle configured to be gripped by a hand of a user; a body having a first end, a second end, and a length defined between the first end and the second end; a base coupled to the first end; a body portion support coupled to the second end. The handle is coupled to the body at a location between the base and the body portion support; and a plurality of electronic components integrated into the smart mobility device including: a display built into the handle such that the display is visible to the user while the user is gripping the handle, a sensor configured to detect a grip of the hand by the user, and a processor in communication with the display. The processor automatically powers up the display, if unpowered, responsive to sensor data indicating that the handle is being gripped.

A mobility assistance kit may be implemented including a smart mobility device 700 as described above, and a second crutch with only some or none of the electronic components of the smart mobility device 700. In some examples, one of the crutches may include a sensor and an electronic communication component (such as Bluetooth, ZigBee, WiFi, or a cellular (e.g., 4G, 5G, LTE) or the like) communicatively coupling the sensor to the processor of the first crutch or to a memory device separate from the mobility assistance kit. In some examples, one of the first and second crutches includes an electronic communication component of a first type and the other one of the first and second crutches includes an electronic communication component of a second type different from the first type. For example, one crutch may include a WiFi electronic communication component and the other crutch may include a Bluetooth electronic communication component. In some examples, the display of the first crutch is configured to display other sensor data acquired by sensors on either the first or the second crutch, and wherein the display is configured to indicate with which crutch the other sensor data is associated. In some examples, at least one of the first and second crutches in a mobility assistance kit includes a power management circuit configured to cause electrical power to be transmitted from one of the first and second crutches to the other one of the first and second crutches.

Figure 14:
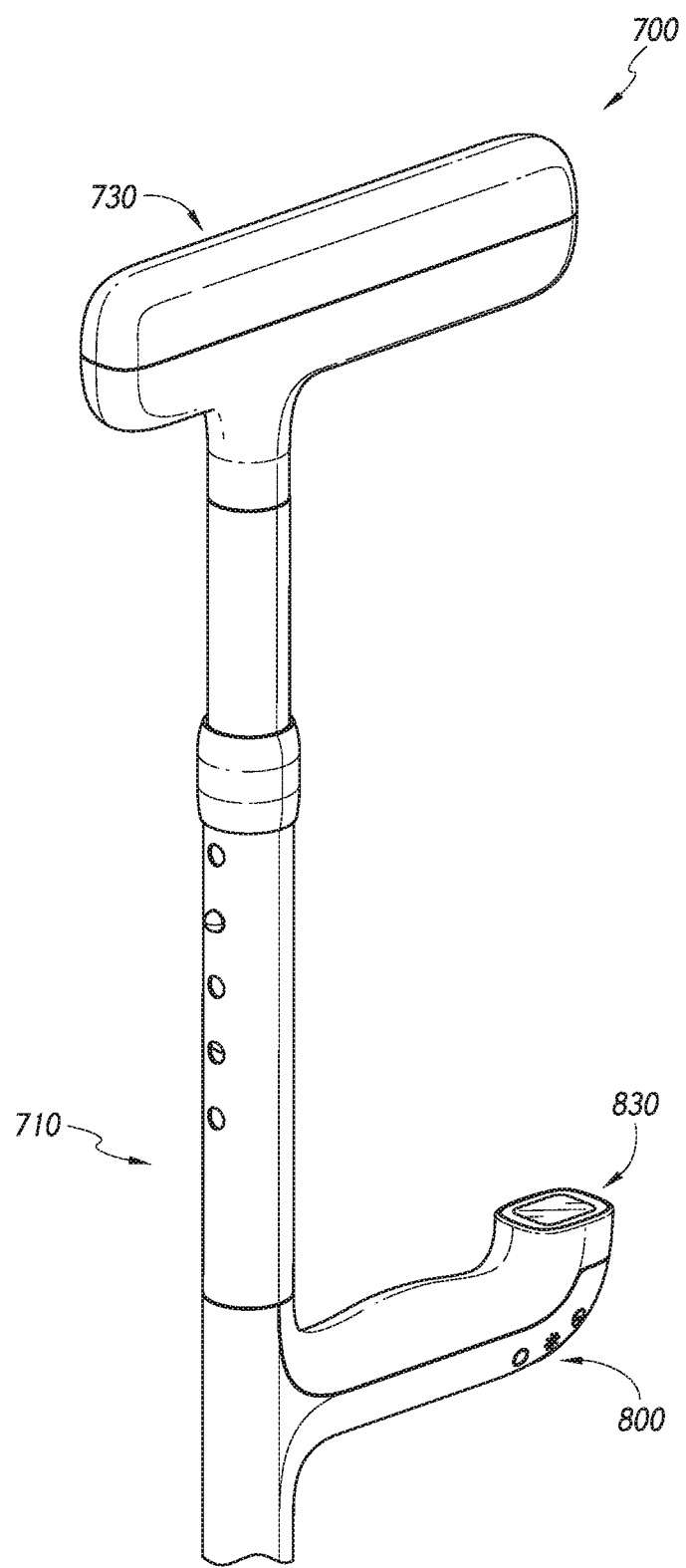
FIG. 14 shows an upper portion of the mobility aid device of FIG. 13, illustrating components and enhanced functions of a smart mobility aid device according to the present disclosure.

Similar to mobility aid device 100, a handle 800, which may provide at least some of the intelligence or enhanced functionality of the mobility aid device 700 (e.g., for safety, connectivity, and or user/activity tracking) may be coupled to the body 710 at a location spaced apart from the base 720. In some examples, such as in the case of a cane, the handle may be coupled to the upper and of the body. In other examples, the handle 800 may be coupled to a location between the two ends 712 and 714 of the body 710. The second or upper end 714 of the body 710 may be equipped with a body portion support 730, with the handle being spaced apart (in opposite directions) from the base 720 and the body portion support 730. The body portion support 730 may be implemented as an axilla support configured to contact the user's armpit or axilla during use as shown in FIGS. 13 and 14. In some such examples, the body portion support 730 may include a support member 732, which extends substantially perpendicular to the body 710 and/or parallel to the handle 800. The body portion support 730 may be implemented as an arm support, e.g., as in the example shown in FIGS. 18 and 19. In some such examples, the body portion 730' may be configured to at least partially encircle the user's arm, such as the user's forearm.

Figure 16:
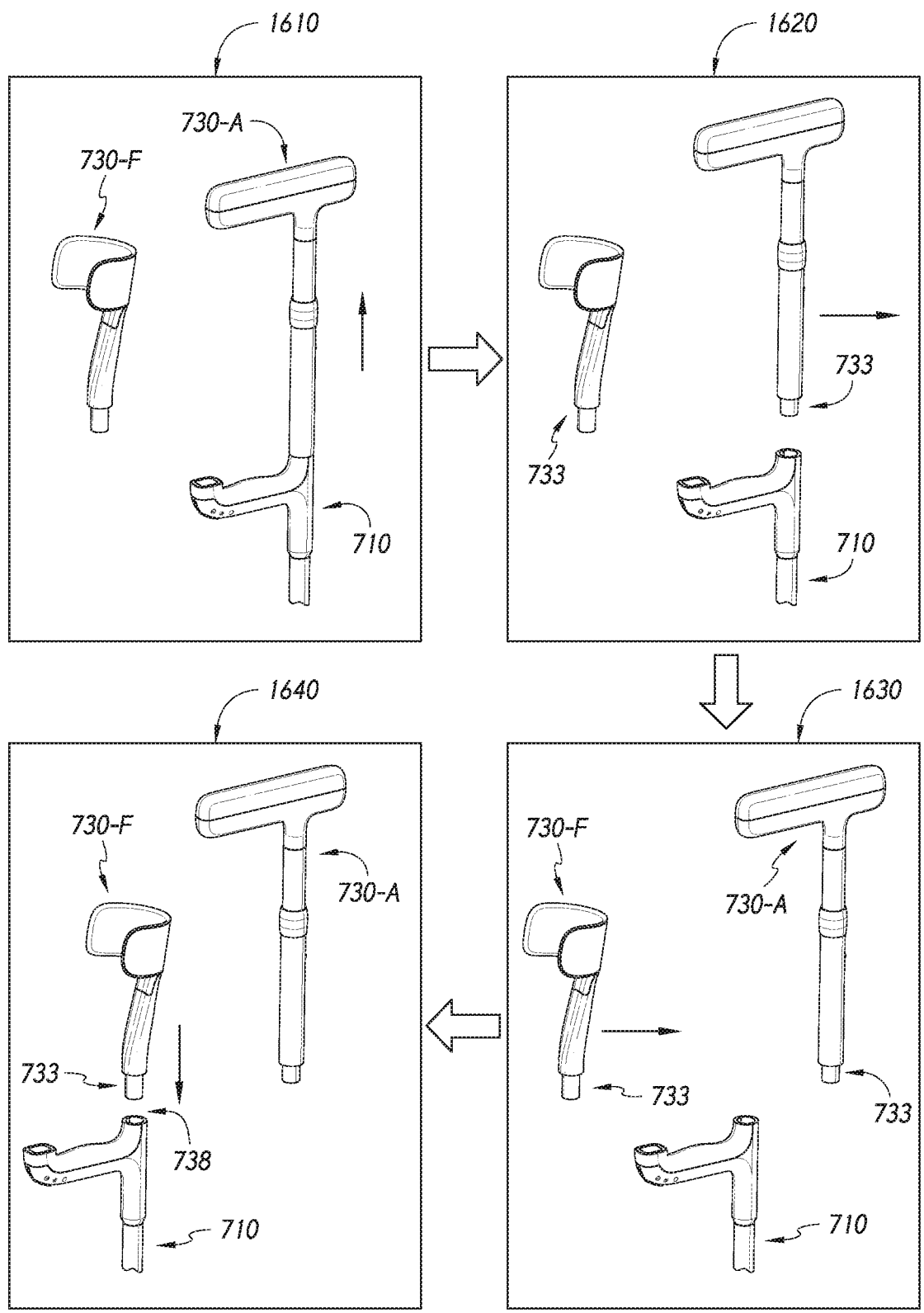
FIG. 16 shows a sequence for interchanging the body portion support of a mobility aid device according to some examples of the present disclosure.
Figure 17:
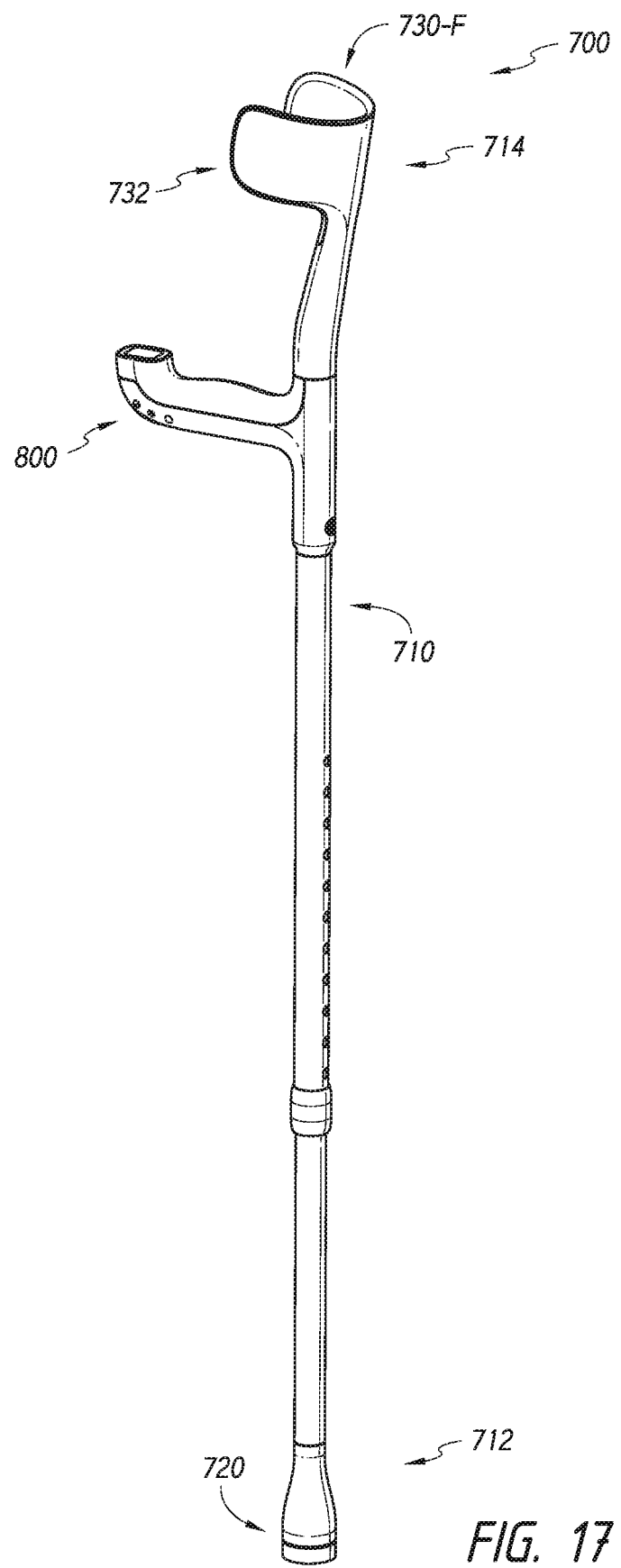
FIG. 17 shows an isometric view of the mobility aid device of FIG. 13 but with a different body portion support provided at the upper end of the body of the mobility aid device.
Figure 18:
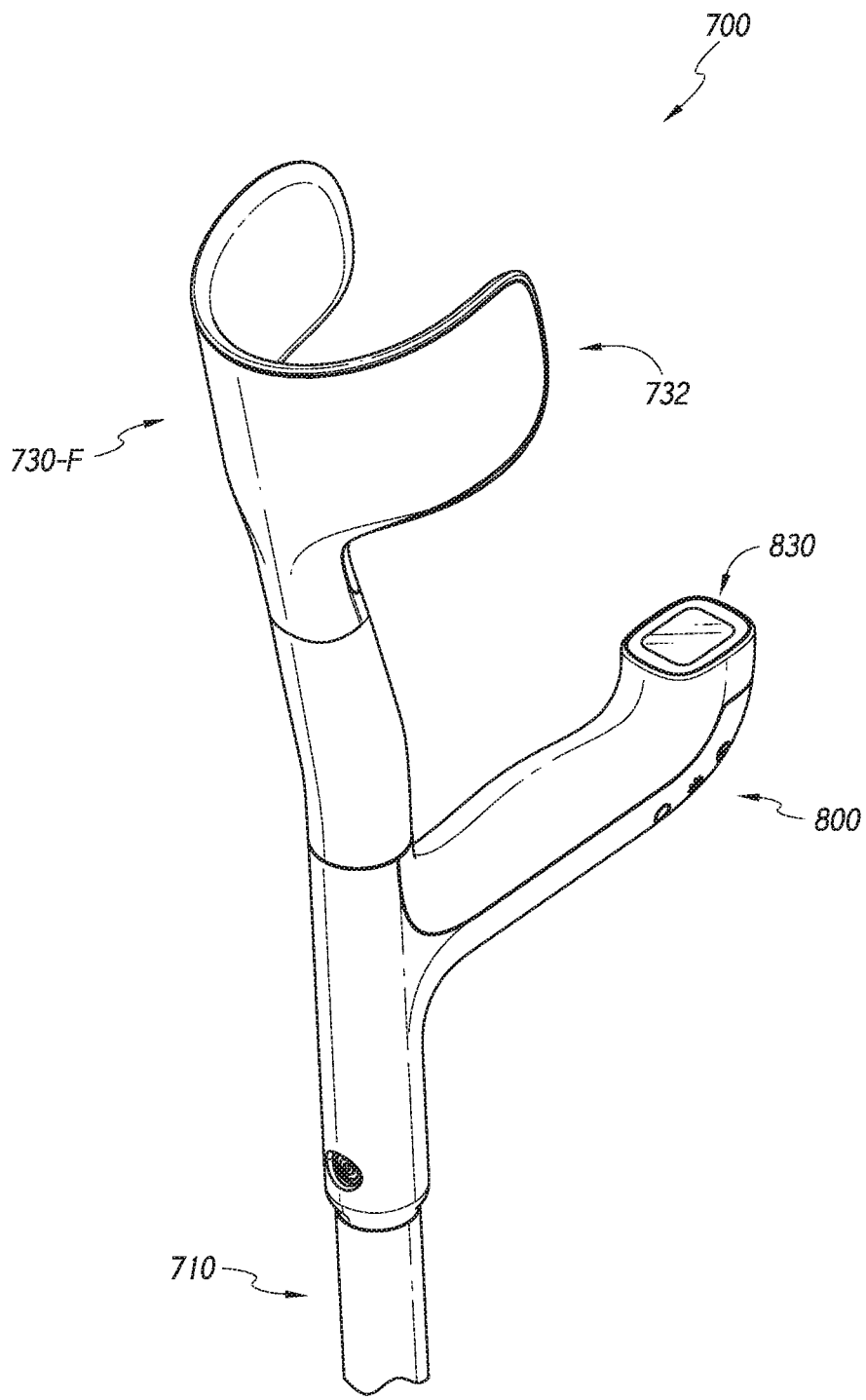
FIG. 18 shows an enlarged partial view of the arm support and handle of the mobility aid device of FIG. 17.

Referring now also to FIGS. 16 and 17, the body portion support 730 may be removably coupled to the body 710 in some examples, such as to allow the user to interchange the body portion support 730. For example, a crutch kit may include one or a pair of crutches, each of which may be provided with two sets of body portion supports 730 of different configuration (e.g., an axilla support 730-A and a forearm support 730-F, each of which may be connected to a coupling structure having the same configuration for interchangeably coupling either of the supports 730 to the body 710. As shown in blocks 1610-1640, the axilla support 730-A and the forearm support 730-F may include a coupling structure, in this case a post 733 of substantially the same diameter to allow of insertion of the post 733 of either of the axilla support 730-A and the forearm support 730-F into an aperture 738 in the body 710. The mobility aid device 700 may include a base 720 coupled to the bottom end (e.g., end 712) of the body 710 with the handle being spaced apart from the base. The base 720, shown in this example as a single-foot tip, may be removably and in some cases interchangeably coupled to the body 710 to allow the user to reconfigure the mobility aid device for a different use case by attaching a different type of base.

Similar to mobility aid device 100, the mobility aid device 700 may include electronic components embedded within the mobility aid device 100, e.g., within the body and/or handle 200, to provide a variety of functions such as those described above with respect to the mobility aid device 100 and intelligence system 500. For example, the mobility aid device 700 may include any suitable combination of sensors, such as a proximity sensor, a touch sensor, a grip sensor, a motion and/or force sensors (e.g., load cells, pressure sensors, accelerometers, and/or IMUs). The handle 800 may include one or more buttons 810, 820, a display 830, and at least one contact sensor 840 (e.g., a biometric sensor such as a heart rate sensor). In some examples, a biometric sensor is located on the side of the handle opposite the display. The buttons may include at least one emergency button (e.g., button 810) and/or at least one functional control button 820 (e.g., to control volume, lighting, to scroll through display features, etc). In some embodiments, the functionality of any of the buttons 810, 820 may be reconfigurable by the user, or automatically and intelligently by the smart mobility aid device. For example, the functional control button 820 may be configured to control volume when the smart mobility aid device is providing an audio service or function (e.g., during a voice call, or audio streaming). The processor of the smart mobility aid device may automatically assign the functional control 820 to a different function, such as to control lighting level upon the initial activation of the lighting system of the smart mobility aid device.

The functional control button 820 may be configured to control the function of scrolling through options, items in a user's electronic shopping cart, a playlist or other selectable items (e.g., contact), when the smart mobility device is performing a function associated with a respective service, e.g., setting up settings of the mobility aid device, communicating with the user's shopping cart, digital play list, or phone book. In some embodiments, an On/Off button, such as the button 810 may at some times, such as upon detection of an emergency or near-emergency condition, perform emergency functions, while at other time, such as during non-emergency conditions, perform a "select," "accept," or "confirm" function. For example, the button 810 may perform the click of a "one-click" shopping function. The "select," "accept," or one click function assigned to button 810 may automatically be assigned by the system (e.g., intelligence system 500 of the smart mobility device) based on the time of day, the location, sensor data, mode of operation, or other inputs. For example, the one-click function of button 810 may be automatically assigned to perform a specific function, e.g., call a taxi, upon detection of the mobility aid device outside of the user's home or at some other specified location. The one-click function may be automatically assigned to checkout function (e.g., with saved payment method of the user) upon detection of the user in the grocery store, etc. In some cases, the one-click function may operate in conjunctions with an automatically re-configurable display, which automatically displays an icon indicative of the one-click function assigned to button 810. For example, when the one-click function is a transportation function (e.g., calling a taxi or Uber), the icon displayed on the display 830 may show a transportation icon such as a car or taxi.

Figure 15A:
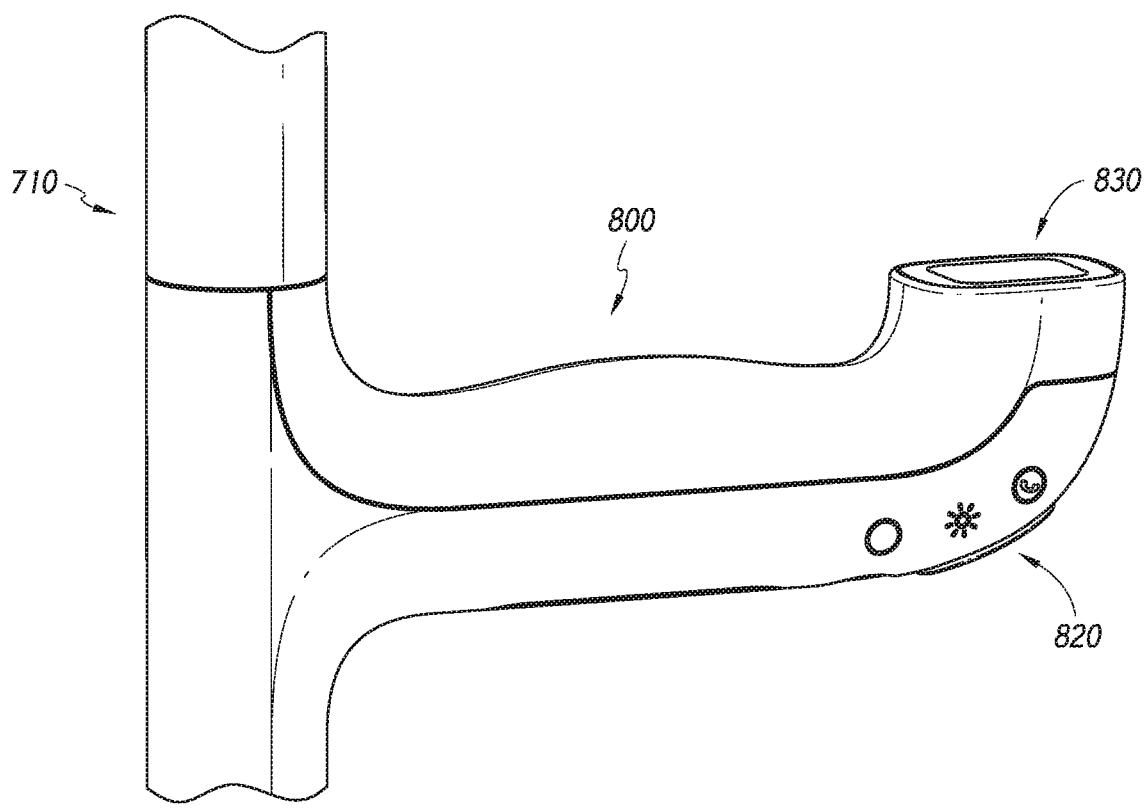
FIGS. 15A and 15B show examples of a handle of a smart mobility aid device according to the present disclosure.
Figure 15B:
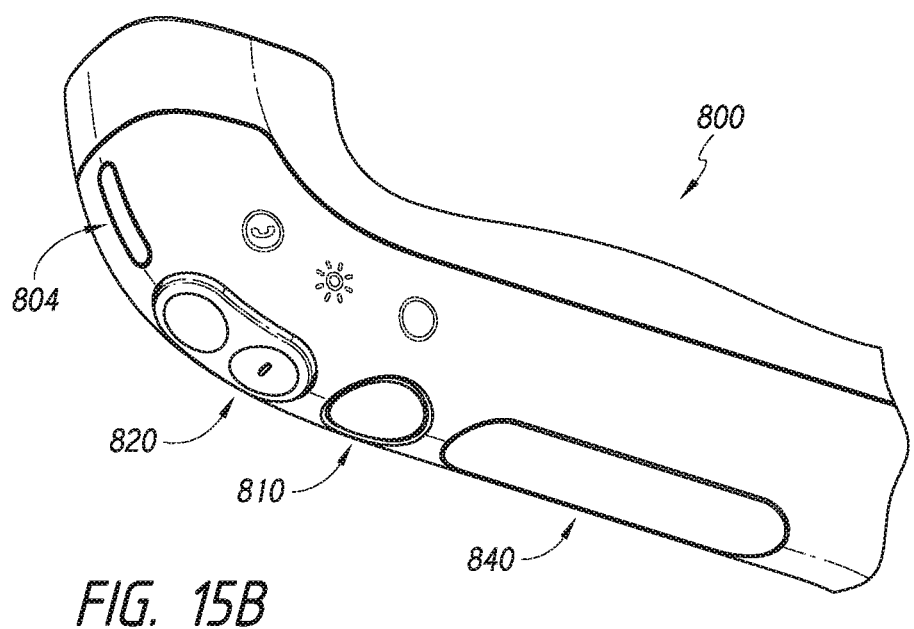

Other examples of re-configurable functions may include an emergency function (e.g., emergency text or call) upon detection of an emergency condition such as a fall, a reminder function (e.g., a reminder that the user has a doctor's or other appointment, or a medication reminder) upon detection of an appointment in the user's calendar, a checkout or other payment function (e.g., upon detection of the user in a store, or when the mobility aid device is electronically connected to a shopping site), an automatic re-order function (e.g., for groceries, food delivery, or some other service), a periodic check in function with a caregiver, e.g., to confirm that the user is in a non-emergency status, and many others. In some cases, the icon indicating the function may be displayed on the side of the handle, near the button whose functionality has been re-assigned based upon a detected condition or environment, as shown in FIG. 15A, or on a surface of the button itself, as shown in FIG. 15B. In some examples, one or more of the controls, such as the functional control 820, which may include a switch (physical or soft control) with a plurality of different selectable states, may have fixed functions, e.g., an emergency function and a setting control function, while another control of the user interface (e.g., button 810) may be reconfigurable (e.g., by the user or automatically by the system) as described herein. In yet further embodiments, the functionality of physical buttons may be set, while re-configurable functionality may be provided with one or more touch-sensitive surfaces on the mobility aid device 700, such as via a touch-sensitive display for the display 830. The handle 800 may also include additional components associated with smart mobility aid device intelligence system, for example one or more intelligently activated lights 804, speakers (not shown), and touch sensor areas.

As with other examples of a smart mobility aid device, the mobility aid device 700 may include at least one light 804. At least one of the lights may be operatively positioned on the body 710 (e.g., directed in combination of forward and downward direction) to illuminate the user's path) or may be otherwise position to serve as a flash light, such as being directed straight ahead. The mobility aid device 700 may include at least one a microphone, a speaker, and other electronic components (e.g., external communication components) for providing one or more of the functions of a smart mobility aid device described herein.

A smart mobility device (e.g., the rollator 101, the mobility aid device 700) may include one or more activity tracking components carried by the smart mobility device for collecting information about a daily activity of the user, and an electronic memory for storing the collected information about the daily activity. A smart mobility device may include an electronic communication component for communicatively coupling the smart mobility device to an external computing device. The processor may be configured to automatically and periodically transmit, via the electronic communication component, the collected information to an electronic memory external to the smart mobility device. As previously described, the mobility aid device (e.g., the smart mobility device 700 shown as crutch in FIGS. 13-20) may be configured to record and track user activity, such as via the use of one or more sensors, at least some of which may be located in the handle 800. The handle 800 may include one or more of the features and/or functions of the handle of the mobility aid device 100, such as grip detection for automatic activation of components, user authentication, biometric measurements, etc.

As with handle 200, the handle 800 may be configured to be gripped by the hand of a user. To that end, the handle 800 may be shaped for an ergonomic fit with a person's hand. As shown in FIG. 14 for example, the handle 800 may include a display 830 configured to be visible to the user when the user's hand is gripping the handle. One or more electronic components associated with an intelligence system of the smart mobility device (e.g., system 500) may be housed within the handle 800 or body 710. For example, the handle 800 may include components of a user interface similar to the user interface 300, including at least one display and at least one user control (e.g., buttons 810, 820). While the components 810 and 820 are referred to herein as buttons, the term button will be understood to include any form of a user control (e.g., a physical or mechanical button or software based control) that allows the user to invoke, activate, or deactivate a function of the smart mobility aid device.

Figure 19:
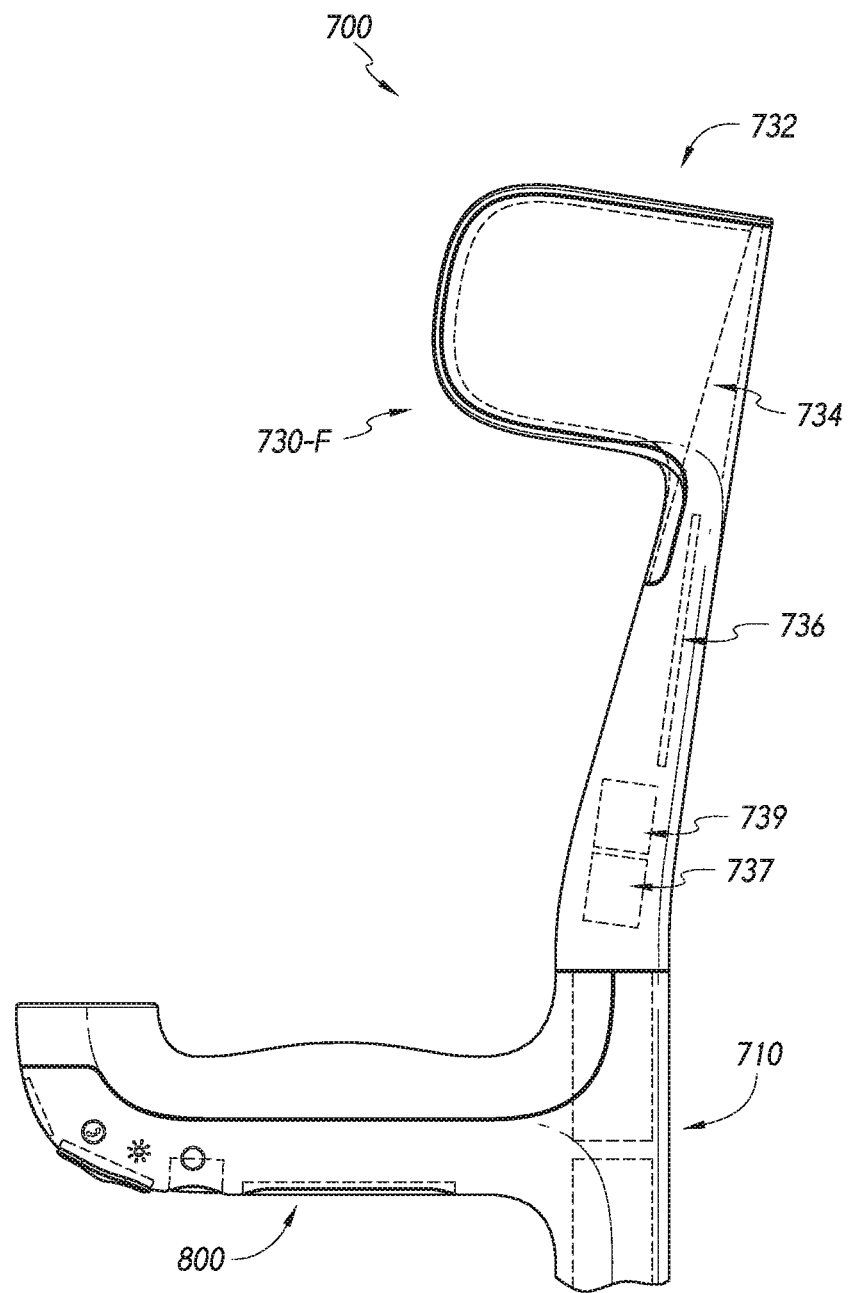
FIG. 19 shows components of a blood pressure sensing assembly integrated into a cuff of the mobility aid device of FIG. 17.

In the example of a crutch, yet additional functionality, e.g., related biometric measurement or tracking of user health information or trends, may be embedded in the smart mobility device. As described, the mobility aid device 700 may be configurable as a crutch with an arm support 730-F which includes a cuff 732 configured to at least partially encircle the user's arm (e.g., the user's forearm). A cuff-type blood pressure sensor assembly may be embedded in the arm support 730-F, e.g., as shown in FIG. 19. The cuff 732 may include an inflatable portion 734 configured to inflate and deflate responsive to a controller circuit 736 (e.g., embodied in an ASIC or PCB). The controller circuit 736 may control the operation of a motor 737 (e.g., an electric motor), which drives a pump 739 (e.g., a pneumatic pump) to inflate the inflatable member 734 in the cuff 732. In some examples, the arm support includes the pump which is operatively coupled to the inflatable member to inflate the inflatable member. In some examples, the mobility aid device 700 includes a blood pressure sensor operatively associated with the inflatable member, a controller in communication with the blood pressure sensor and the pump, to cause the pump to inflate the cuff and the blood pressure sensor to automatically acquire a blood pressure measurement responsive to inflation of the cuff. For example, the processor of the intelligence system of the smart mobility device 700 may cause the controller circuit 736 to periodically (e.g., one per hour, every two or more hours, once per use session, etc.) inflate the inflatable member 734 for automatic period blood pressure measurements of the user by the smart mobility device. In some cases, a push of a button or a squeeze on the handle (e.g., detected by a grip sensor) may cause the automatic taking of a measurement such as a blood pressure measurement, and thus may initiate the sequence of inflating and operatively deflating the cuff to take the blood pressure measurement.

Figure 20:
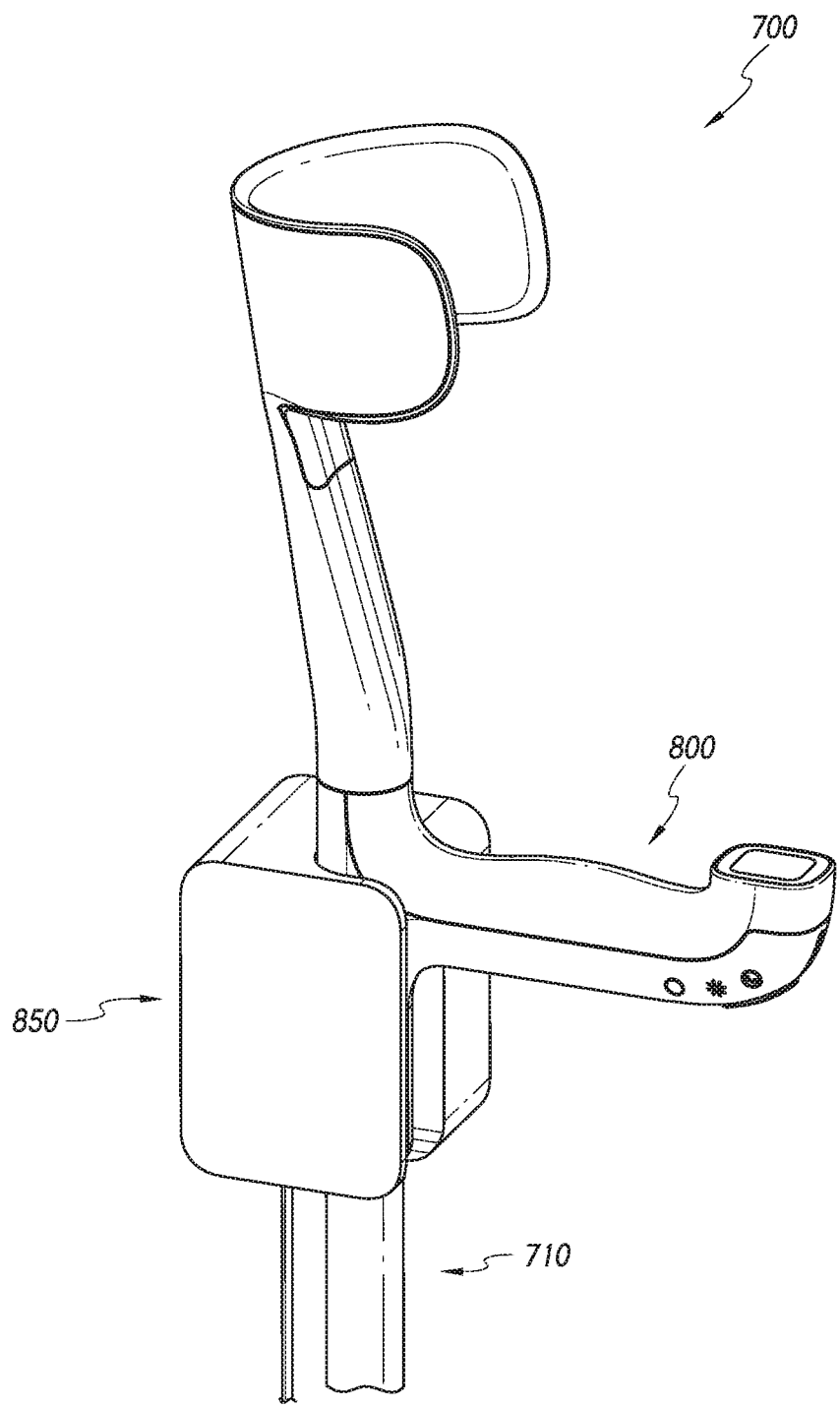
FIG. 20 shows a charging apparatus for charging a smart mobility device according to the present disclosure.

As also described, a smart mobility device (e.g., mobility aid device 700) may be re-chargeable by placing the mobility aid device 700 in or on a charger 850, which in the example in FIG. 20 is also configured as a holder for conveniently and neatly storing the mobility aid device 700 while not in use. The charger 850 may thus include a charging circuitry integrated therein. The mobility aid device 700 may be recharged wirelessly such as via a coil in the charger 850 operatively positioned to couple (e.g., inductively, resonantly) to a coil in the body 710 of the mobility aid device 700 near the handle 800. In other examples, the charging may be via a wired connection and the mobility aid device 700 and charger 850 may include cooperating male and female connectors to establish a wired connection. In some examples, the wired charging may be through electrical contact of conductive surfaces, without necessarily plugging male and female connectors together. The charger 850 may include a holding cavity, which may be provided with one or more magnetic couplings for magnetically aligning and/or retaining the mobility aid device 700 to the charger 850. In some examples, the holding of the mobility aid device may alternatively or additionally be mechanical means (e.g., a hook, clamp, interlocking surfaces, a ledge, or other suitable structure(s)). While the charger 850 is shown to interface with the mobility aid device 700 at a location near the handle, in other examples, the charging components (e.g., coil or plug for wired charging) may be located elsewhere on the body 710 such as closer to the tip. In some such cases, the mobility aid device may be suspended or held upside down in the charger 850.

To preserve the small form factor of the mobility aid device and still enable communication via a plurality of different methods (e.g., Bluetooth, ZigBee, WiFi and/or cellular), one of the handles may include an electronic communication component of a first type (e.g., a Bluetooth or a WiFi communication component), while the other handle may include an electronic communication component of a second different type (e.g., a WiFi or a cellular communication component).

Figure 21:
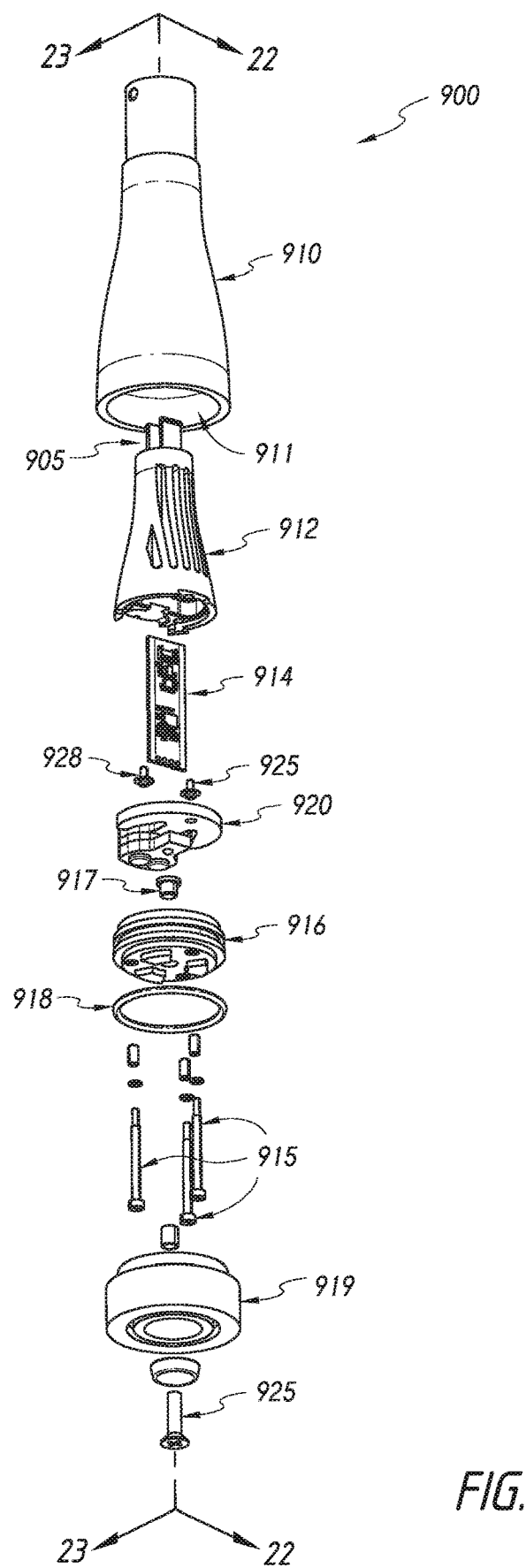
FIG. 21 shows a partial exploded view of a smart tip for use with a mobility aid device.
Figure 22:
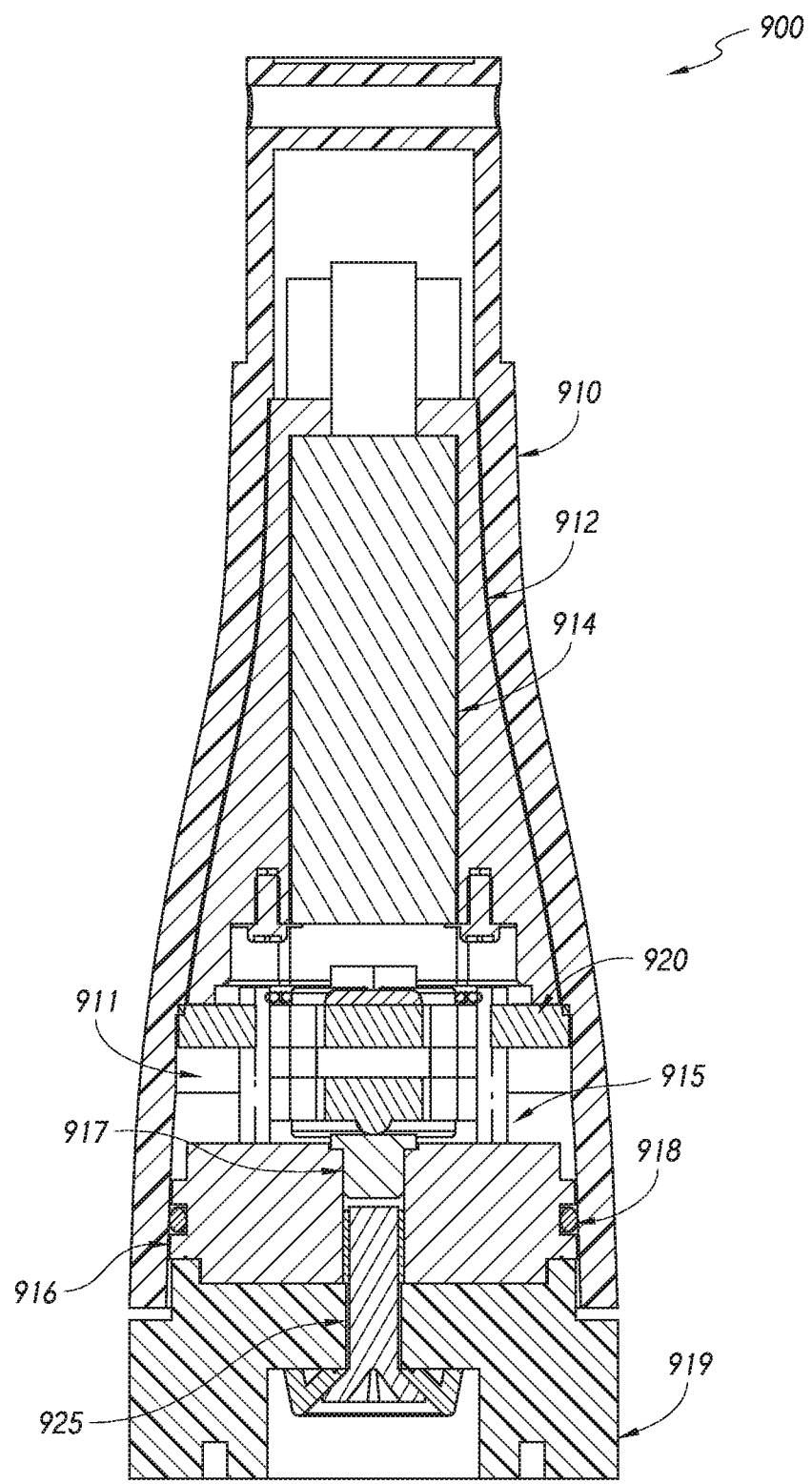
FIG. 22 shows a section view of the smart tip of FIG. 21 taken along section line 22-22 of FIG. 21.
Figure 23:
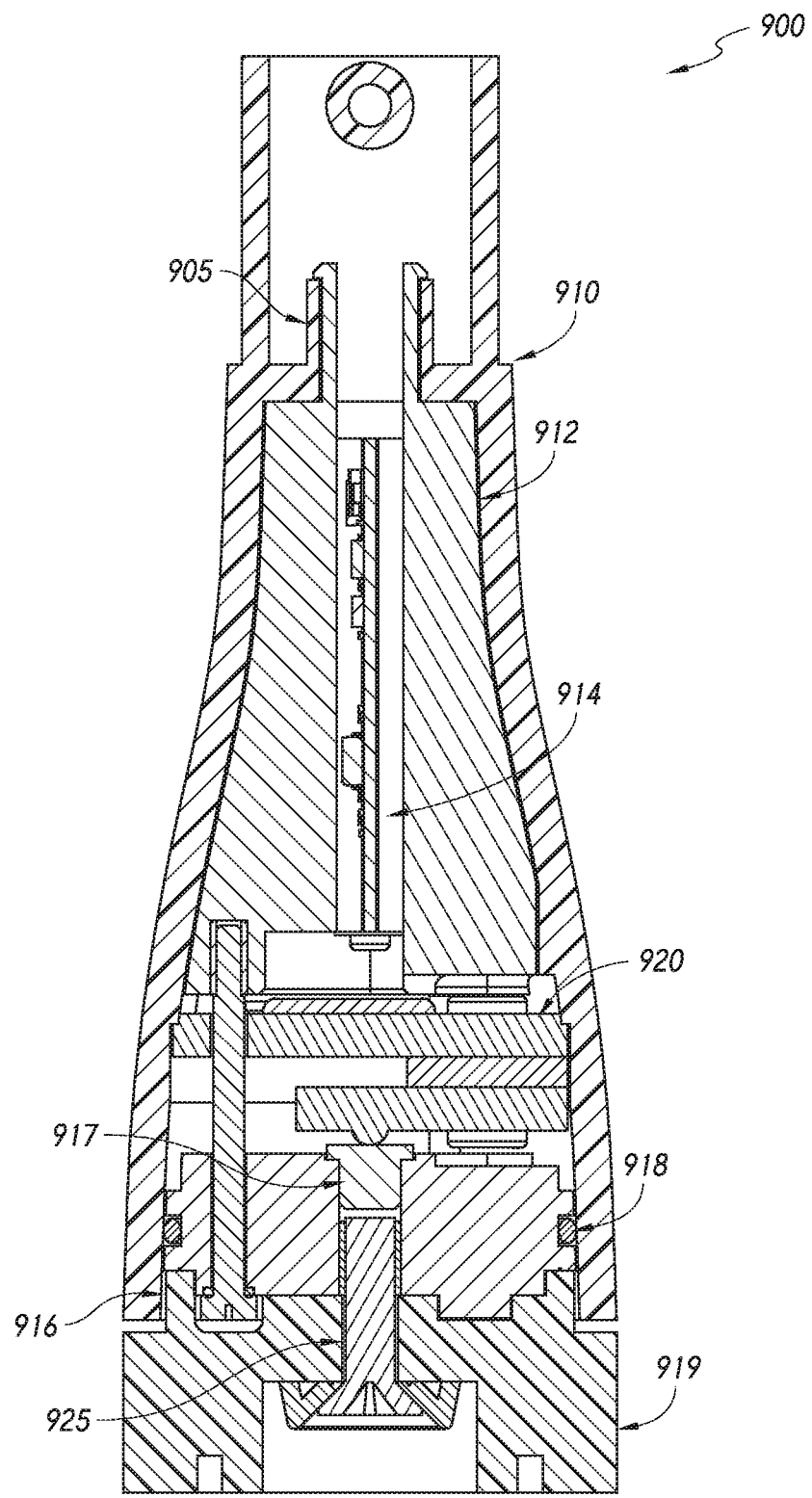
FIG. 23 shows a section view of the smart tip of FIG. 21 taken along section line 23-23 of FIG. 21.

FIGS. 21-23 and 25A-26C illustrate examples of a sensor assembly that may be located in the base (e.g., tip 720) of a smart mobility aid device, such as a smart cane, a smart crutch, or a rollable device. FIG. 21 shows an exploded view of a smart tip 900 and FIGS. 22 and 23 show two orthogonal section views of the smart tip 900. FIG. 25A shows an elevation view of a smart tip 2500 in a first configuration. FIG. 25B shows the smart tip 2500 in a second configuration, where a flexible coupling enables feet of the smart tip to tilt relative to a portion of a mobility aid device. In some embodiments, the smart tip 900 includes a flexible coupling as described with respect to the smart tip 2500. The smart tip 900 and/or the smart tip 2500 may be used to implement the base 720 of the crutch 701 described with reference to FIGS. 13-18 or the base of another smart mobility aid device of the present disclosure.

The smart tip 900 and/or the smart tip 2500 includes a sensor assembly that may be used to obtain various sensor data, such as strain data, motion data, or other, such that any suitable combination of the sensor data may be used to derive additional information about the use of the smart mobility aid device (e.g., trends in load applied by the user). In some embodiments, a smart tip (e.g., smart tip 900 as shown in FIGS. 21-23 and/or the smart tip 2500 shown in FIGS. 25A-26C) may be used to retrofit a conventional (or dumb) mobility aid apparatus, as the smart tip may include the electronics necessary to track and record data representative of the use of the device, which data may then be transmitted (e.g., via a communication component in the smart tip) to another computing device for further analysis. In some such examples, a smart tip may include a power source, which may be rechargeable, for powering the electronic components. In some examples, the electronics suite (e.g., the sensor assembly) in the smart tip 900 and/or 2500 may communicate the recorded data to a processor onboard the smart mobility device, such as a central processor (e.g., processor 530) located elsewhere in the body (e.g., in the handle or elsewhere proximate to a display) of the smart mobility aid device. In some such examples, the power source for the electronics in the tip may reside in the tip or it may be transmitted to the tip, e.g., via a wire harness connecting the smart tip to the main electronics assembly (e.g., in the handle).

Referring now to FIGS. 21-23, a smart tip 900 may include an inner body 912, which supports the electronics of the smart tip 900 including the one or more sensors (e.g., load cell 920). In the illustrated example, the inner body 912 is enclosed within an outer housing 910, which may be made of any suitable rigid material, such as metal, rigid plastic or a composite material, and which serves to enclose and protect the internal electronics of the smart tip. While shown as separate components (e.g., for ease of manufacture), the inner body 912 and the outer housing 910 may, in some examples, be integrally formed, such as through a suitable casting and/or machining process(es). In some examples where two separate components are used to provide the inner body and outer housing combination, the two may be coupled using any suitable coupling means, such as fusing, welding, bonding, fastening, and/or otherwise mechanically attaching the two components, such as via a male-female snap connector 905.

Coupled to the body 912 and housing 910 are a load cell 920, which in the illustrated example is fastened to the body 912 via fasteners 928, and a circuit board 914, which is in electronic communication with the load cell 920. The load cell 920 may be configured to track user activity or derive information pertaining to the user's health, as previously described. For example, the load cell 920 may generate gait or stride measurements, and may measure a load imparted to a smart mobility device by a user. The load cell 920 may enable a processing element to develop trends in load imparted to the smart mobility device to correlate to the user's health. For example, if a user applies less load to the smart mobility device over time, that trend may be indicative of an improvement in the user's ability to walk with less reliance on a smart mobility device. Likewise, a trend of increasing load may indicate the user is more reliant on the smart mobility device and be indicative of a decline in health. In the present example, the body 912 defines a cavity configured to accommodate circuitry of the smart tip (e.g., provided on a circuit board 914). The circuit board 914 may be substantially rigid and is arranged substantially vertically within a cavity of the inner body 912. However, in other examples, the electronic circuits associated with the sensor suite in the tip may be provided on one or more flexible circuit boards, which may be differently arranged in the body of the smart tip 900.

In this embodiment, the smart tip includes a load cell 920, such as a strain gauge load cell. The load cell 920 may be a full Wheatstone bridge strain gauge. However, in some examples a half (i.e. two strain gauges) or a quarter bridge (i.e. single strain gauge) may be used. The load cell 920 may provide an output strain signal, typically an analog signal, which may be coupled to an amplifier circuit that resides, for example, on the circuit board 914. The measured strain signal may be applied to improve the resolution of the signal as the amplitude of the measured strain signal may be too low (e.g., on the order of millivolts) to effectively analyze the signal. In some examples, the amplified signal may be further coupled to a filter for reducing the noise component of the signal and/or to an analog-to digital converter (ADC) which converts the analog strain measurement signal to a digital strain measurement signal. The digitized signal may then be coupled to a processor circuit for determining the load applied to the smart tip based on the strain measured by the load cell 920. The processor circuit, which may be located in the tip 900 or be part of the main or central processor (e.g., in the handle) may perform this determination using calibration data that maps applied load to resulting strain signal output, and which may be stored onboard the smart mobility device.

On the opposite side of the load cell 920 is a presser plate 916, which is operatively associated with the load cell 920 (e.g., via a pin 917) to transfer the load applied by the user to the load cell 920 for sensing. The outer housing 910 defines an opening to the cavity 911, e.g., to enable installation of the internal electronics, and the opening to the cavity 911 may be capped by a tip end body 919, which effectively seals the electronics within the interior cavity 911 of the tip 900. In some embodiments, to better seal the cavity 911 from water, dust, or other debris, one or more sealing components may be used. For example, a sealing element 918 (e.g., o-ring) may be provided circumferentially on the presser plate 916 to prevent the passage of water and debris into the portion of the cavity 911 containing the electronics. The tip end body 919 may be formed of a resilient material, such as rubber (natural or synthetic) or other non-resilient material that provides a sufficient amount of traction with the ground. The tip end body 919 may be rigidly attached (e.g., by fastener 925) to the presser plate 916, such that displacement of the tip end body 919 is transferred to the presser plate 916, which transmits, via the interaction between the pin 917 and the pin seat in presser plate 916, a corresponding displacement to the load cell 920. The load cell 920 and presser plate 916 are aligned to the inner body 912 and movably coupled thereto via shoulder screws 915. The shoulder screws not only allow relative movement of the load cell 920 and presser plate 916 relative to the inner body 912 and housing 910 but may also act as an alternate load path to prevent excessive load from being applied to the load cell. For example, the load applied to the load cell may be limited to below the ultimate tensile strength or below the yield strength of the strain gauge(s) (e.g., up to about 300 lbs).

In some embodiments, the smart tip 900 may include one or more additional sensors, such as an integrated position and orientation sensor (e.g., IMU), a motion sensor, accelerometer, or others, which may be provided on the circuit board 914. The measurements from the additional sensors may be used independently from the strain data to obtain other information about the use of the mobility aid device, such as distance travelled and/or to detect a fall. In some cases, the measurements from the additional sensors may be used in conjunction with the load data for deriving further information (e.g., trends) relating to the loading of the device.

The smart tip 2500 may include components and functionality also included in the smart tip 900, as previously described. For example, in some embodiments, the outer housing 910, sealing element 918, load cell 920, the presser plate 916, the circuit board 914, and screws 915 of the smart tip may be similar to, or the same as, elements described with respect to the smart tip 900. The smart tip 2500 and/or the smart tip 900 may be adapted to be associated with (e.g., attached to or formed with) a portion, such as an elongate element 710, of a mobility aid device. The elongate element 710 may have a longitudinal axis 2536 that runs along its long dimension, and may have a transverse axis 2538 running substantially perpendicular to the longitudinal axis 2536.

As shown for example in FIGS. 25A-26C, the smart tip 2500 may have one or more feet 2524. The foot 2524 may be spaced apart from a longitudinal or central axis of an elongate member 710 or a body of a mobility aid device. The foot 2524 may increase the stability of a mobility aid device. For example, the foot 2524 may increase the stability of the mobility aid device when used by a user to ambulate by giving the user more points of contact, a broader base of contact, or by adapting to uneven or rough surfaces. Additionally, the foot 2524 may allow a mobility aid device such as a cane or crutch that would normally not be free-standing to stand on its own (e.g., as shown in FIG. 25A), thereby positioning the mobility aid device for easy retrieval by the user. In various examples, the smart tip 2500 may include two, three, four, five, or more feet.

Figure 26A:
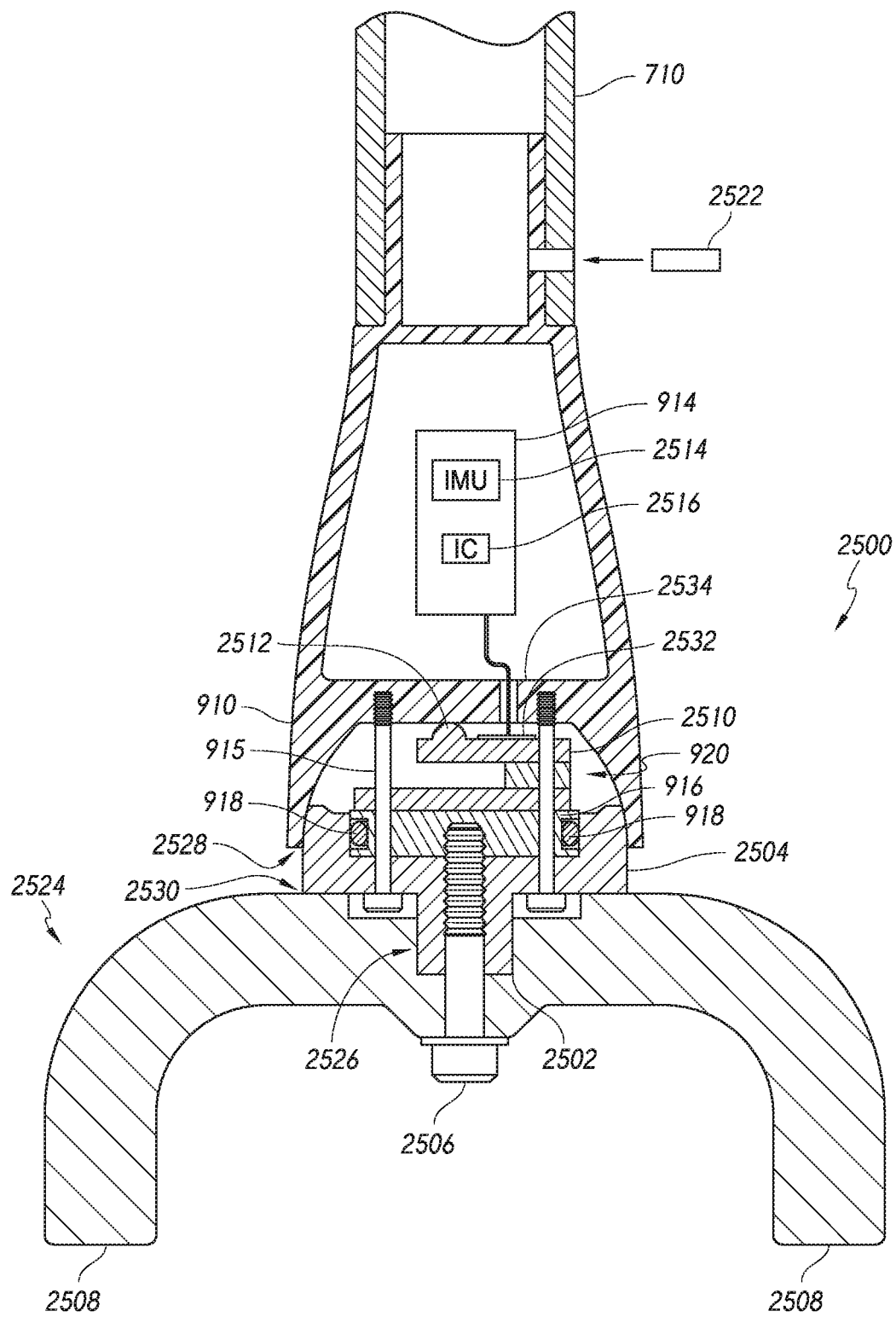
FIG. 26A shows a cross section of the smart tip of FIG. 25A taken along section line 25B-25B of FIG. 25A.

FIGS. 25B and 26A show a cross section of an embodiment of the smart tip 2500. Each of the one or more feet 2524 of the smart tip 2500 has a respective tip end portion 2508 adapted for contact with a support surface 2501 such as the ground or a floor. The tip end portions 2508 may include anti-slip, anti-skid, or friction enhancing features, coatings, or elements to reduce slippage of the end portions relative to the support surface. When more than one foot is used, the feet 2524 may be separate components, or may, as shown in FIG. 26A, be elements of a unitary piece. The foot 2524 may be operatively coupled to a flexible coupling 2504.

The one or more feet 2524 are adapted to contact a support surface 2501. The one or more feet 2524 are operatively coupled to the smart tip 2500 by a flexible coupling 2504 such that the one or more feet 2524 can tilt with respect to the body of the smart mobility device. The flexible coupling 2504 may be coupled to the foot 2524 by a fastener 2506. The fastener 2506 may pass through an aperture in the flexible coupling and engage with a presser plate 916 disposed at an opposite side of the flexible coupling 2504 from the head of the fastener. In some embodiments, the flexible coupling 2504 may be attached or affixed to the foot 2524 by other suitable structures, with adhesives, or may be molded, cast or unitarily formed with the foot 2524. The flexible coupling 2504 may be fastened to an outer housing 910 with one or more fasteners 915. A portion of the flexible coupling 2504 may be received in a portion of the outer housing 910. For example, the outer housing 910 of the smart tip 2500 may form a cavity 911 that receives a portion of the flexible coupling 2504. The outer housing 910 may have an interior wall 913 adapted to cooperate with an outer wall 2515 of the flexible coupling 2504. For example, the interior wall 913 may have an arcuate shape within which the outer wall 2515 of the flexible coupling 2504, which may have a corresponding arcuate shape, may pivot or flex to further help simulate the natural motion of a user's foot and/or ankle. The fasteners 915 may pass through apertures in the flexible coupling, apertures in the presser plate, apertures in a load cell 920, and/or engage with apertures in the outer housing 910. The fasteners 2506 and/or 915 may be screws, bolts, rivets, or other suitable fasteners. The fasteners 915 may act as guides and/or may transmit force through the smart tip 2500. The outer housing 910 may be adapted to be coupled with a portion of a mobility aid device, for example with a tube, shell, or other structure such as an elongate element 710. For example, the outer housing 910 may include a collar adapted to be received within an inner portion of the elongate element 710, as shown in FIG. 26A. In some embodiments, the outer housing 910 may be adapted to receive an outer portion of the elongate element 710. For example, the outer housing 910 may include an aperture adapted to receive the elongate element 710. The outer housing 910 may be secured to the elongate element 710 by a fastener 2522, such as a shear fastener, pin, screw, rivet, bolt, or the like.

FIG. 25B shows an example of a flexible coupling enabling relative tilt between the foot 2524 and an elongate element 710 of a mobility aid device, as indicated for example by the arrow 2533 and/or the tilt angle θ1. Relative tilting of the foot 2524 and the body of a mobility aid device may help simulate the natural motion of a foot and ankle and may aid a user while walking with a mobility aid device including the smart tip 2500. As shown in FIG. 25A, the tip end portions may be at rest against a support surface, and the elongate element 710 (e.g., a shaft of a cane or crutch) may be substantially normal to the support surface. In this configuration, the longitudinal axis 2536 of the elongate element 710 and a longitudinal axis 2540 of the smart tip 2500 may be substantially aligned, as shown in FIG. 25A. In FIG. 25B, the smart tip 2500 is shown disposed with a foot 2524 in contact with the support surface 2501 and another foot 2524 above the support surface 2501, such that the longitudinal axis of the foot 2524 forms an angle θ2 with respect to an axis normal to the support surface 2501. Such a disposition may occur as a user walks with a mobility aid device including a smart tip 2500 and the foot 2524 tilts with respect to the elongate body 710 simulating natural ankle and foot movement. The angle θ2 may be exaggerated as shown in FIG. 25B and may be more or less than as shown, Such a disposition may induce a force or moment between the foot 2524 and the elongate member 710 such that the flexible coupling 2504 enables the foot 2524 and the elongate member 710 to tilt a tilt angle θ1 relative to one another. For example, as shown in FIG. 25B, the longitudinal axis 2536 of the elongate element 710 is flexed at a tilt angle θ1 with respect to the longitudinal axis 2540 of the foot 2524. A tilt angle θ1 may also be induced between the foot 2524 and the elongate element 710 when the foot 2524 of the smart tip 2500 is in the configuration shown in FIG. 25A with the feet in in contact with the support surface 2501, as indicated by the arrow 2533. Such a configuration may occur when a user uses the mobility assistance device to transition from standing and seated positions, and flexes the elongate body 710 relative to the foot 2524, while the foot is in contact with the support surface 2501.

The flexible coupling 2504 may be implemented as a rocker or damper that enables tilting movement of the smart tip 2500 relative to a portion of a mobility aid device such as an elongate element 700. The flexible coupling 2504 may be made from a deformable material such as a material that can be deformed elastically under typical forces imparted to the coupling while in use by a user using a smart tip 2500 with a mobility aid device. The flexible coupling may allow the foot 2524 to tilt in any radial direction (e.g., along any transverse axis to the longitudinal axis 2536 of the elongate element 710, 360° around the elongate element 710). Further, the flexible coupling 2504 may allow the radial direction of the tilt angle θ1 to roll or point to other radial directions while tilted. In some embodiments, the material of the flexible coupling 2504 may be an elastomer for example a natural or synthetic rubber, EPDM, neoprene, polyurethane, silicone, nitrile, or the like. The flexible coupling 2504 may deform or flex under load, but return to substantially its original shape and/or size when unloaded. Elastic tilting of the foot 2524 relative to the elongate element 710 may simulate a natural movement of a user's ankle, and this assist the user to walk. The flexible coupling 2504 may impart a restoring force to either or both the foot 2524 and the elongate member 710 that tends to restore the alignment of the foot 2524 and the elongate member 710. The more the flexible coupling is flexed (i.e., the larger the tilt angle θ1), the larger the restoring force may be.

The tilt angle θ1 or movement of the smart tip 2500 relative to a portion of the mobility aid device (e.g., the elongate element 710 or body) may be limited by a tilt limiter. For example, as the flexible coupling 2504 deforms, allowing relative tilt between the outer housing 910 and the foot 2524, and an increasing angle θ1, an upper tilt limiter 2528 positioned for example at a lower end of the outer housing 910 may come into contact with a lower tilt limiter 2530 positioned on a portion of the smart tip, such as the foot 2524. Contact of the upper and lower tilt limiters may prevent tilt of the foot 2524 to a tilt angle θ1 greater than desired. For example, tilt limiters 2528, 2530 may limit the tilt angle θ1 to less than about 5°, 10°, 15°, 20', or even less than 45°. Other suitable structures for limiting the tilt angle θ1 may be used.

Figure 26B:
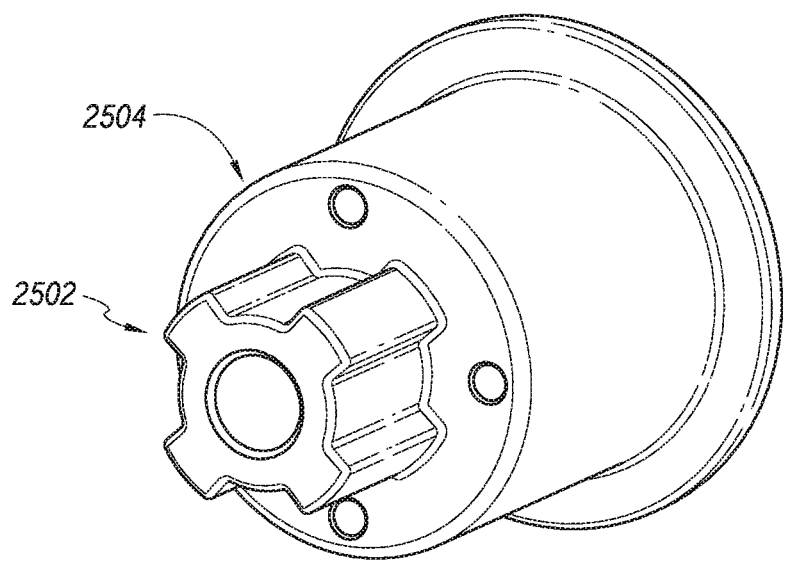
FIG. 26B shows an isometric view of an example of a flexible coupling of the smart tip of FIG. 25A.
Figure 26C:
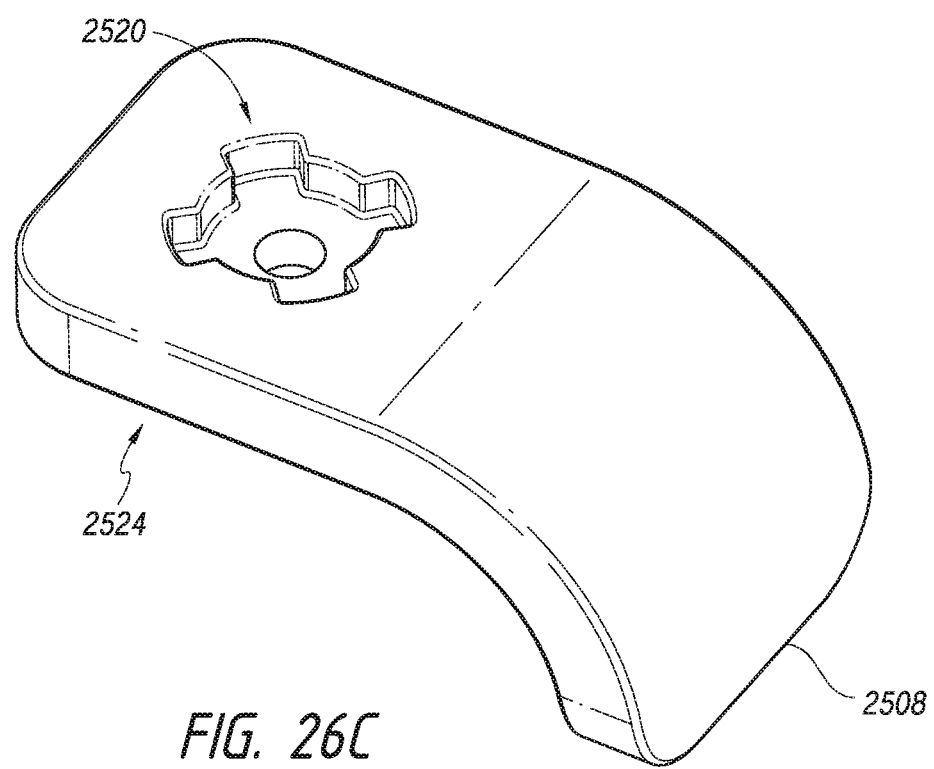
FIG. 26C shows an isometric view of an example of a foot element of the a of FIG. 25A.

The flexible coupling 2504 may include a non-rotatable coupling 2526 that prevents or limits relative rotation of the foot 2524 and a portion of a mobility aid device (e.g., the elongate element 710). For example, the non-rotatable coupling 2523 may limit rotation or spinning of the foot 2524 about the longitudinal axis 2540 of the smart tip 2500 and/or a portion of a mobility aid device, such as the elongate element 700. FIG. 26B shows an isometric view of an embodiment of a flexible coupling 2504 including a protruding portion 2502 of the non-rotatable coupling 2526. FIG. 26C shows an embodiment of a receptacle 2520 adapted to receive the protruding portion 2502 and together form a non-rotatable coupling 2526. The protruding portion 2502 shown for example in FIG. 26B is implemented as a spline with a plurality of teeth separated from one another by a tooth space. The receptacle 2520 likewise includes a plurality of teeth separated from one another by a tooth space. The teeth of the protruding portion 2502 are adapted to be received in the tooth spaces of the receptacle 2520, and the teeth of the receptacle 2520 are adapted to be received in the tooth spaces of the protruding portion 2502. Thereby, the protruding portion 2502 and the receptacle 2520 can engage to form the non-rotatable coupling 2526. The teeth and the tooth spaces of the protruding portion 2502 and the receptacle 2520 may be of any suitable shape or profile, (e.g., involute, parallel key, crowned spline, serrations, helical spline, or the like). Either of the protruding portion 2502 or the receptacle 2520 may be associated with either of the flexible coupling 2504 or the foot 2524. Other suitable non-rotatable couplings may be used, including for example gears; keyed connections; integral forming of the flexible coupling 2504 with the foot 2524 (e.g., molding, overmolding, or the like); an adhesive; or unitary forming of the flexible coupling 2504 and the foot 2524.

The non-rotatable coupling 2526 may allow limited twisting of the foot 2524 relative to a portion of the mobility aid device. For example, the flexible coupling 2504 may provide a limited amount of elastic torsional strain such that the foot 2524 may flex or twist relative to the longitudinal axis 2536 a limited amount relative to an elongate element 710 of a mobility aid device while still preventing spinning of the foot 2524. Thus, the non-rotatable coupling 2504 may increase the stability and adaptability of a mobility aid device.

As described with respect to the smart tip 900, the smart tip 2500 may include a sensor assembly and electronics suite that may be used to obtain sensor data, such as strain data, motion data, tilt data, flex data, or other data related to the use of the smart tip 2500 of a smart mobility device. A circuit board 914 may be included in the smart tip 2500. The circuit board 914 may include an IMU, such as a gyroscope, accelerometer, or other suitable position and orientation sensor.

The smart tip 2500 may include a load cell 920 similar to the load cell in the smart tip 900. The load cell 920 may be positioned between the presser plate 916 and a bulkhead or wall 2534 of the outer housing 910. For example, the load cell 920 may include a deflection member 2510 that bends elastically under an applied load. The load cell 920 may include a load contact 2512 disposed on, or formed with, the deflection member 2510 and in contact with the bulkhead 2534. A strain sensor 2532 such as a strain gauge may be associated with the deflection member 2510 and configured to detect a strain or deflection of the deflection member 2510, as previously described with respect to the smart tip 900. The strain gauge may be adhered, attached, or formed with the deflection member. A strain of the deflection member 2510 may be correlated to an applied force on the smart tip 2500. The load contact 2512 may be movable about the surface of the bulkhead 2534 with which the load contact 2512 is in contact. Relative motion of the load contact 2512 about a face of the bulkhead 2534 may reduce or eliminate biasing of readings of the load cell caused by lateral forces imparted on the smart tip 2500, such as when the smart tip is flexed at a tilt angle θ1 relative to the mobility aid device. For example, the load contact 2512 may be in the shape of a hemisphere or other suitable shape that allows the load contact 2512 to slide laterally (e.g., side to side, front to back, or a combination thereof) across the bulkhead 2534 when a tilting load is applied to the smart tip 2500, thus reducing bias or measurement errors of the load cell 920. The load contact 2512 may transmit force (e.g., a weight or force imparted by a user using a mobility aid device including a smart tip 2500 for example along a longitudinal axis of a mobility aid device) from the bulkhead 2534 to the load cell 920. The load cell 920 may be positioned in a position other than as shown in FIG. 26A. For example, the load cell 920 could be inverted from the position shown, such that the load contact 2512 is in contact with the presser plate 916 and a base of the load cell 920 is in contact with the bulkhead 2534. The bulkhead 2534, the presser plate 916, and the load cell 920 may be made of any suitable material, such as steel or other metals, plastic, fiber reinforced composites, or the like. Other suitable arrangements of load cells may be used.

The strain sensor 2532 and/or the IMU 2514 may be in electrical communication with a processing element 2516 and/or a power source of the circuit board 914. The processing element 2516 may receive signals from, and/or provide power to, the IMU 2514 and/or the strain sensor 2532, or another circuit in the load cell 920. These data may be used as described with respect to other smart mobility devices of the present disclosure (e.g., detecting gait, stride, falls, use strength, and the like). Additionally or alternately, data from the IMU 2514 may be used with data of the load cell 920 to correct load cell 920 data for bias caused by lateral loading.

Figure 24A:
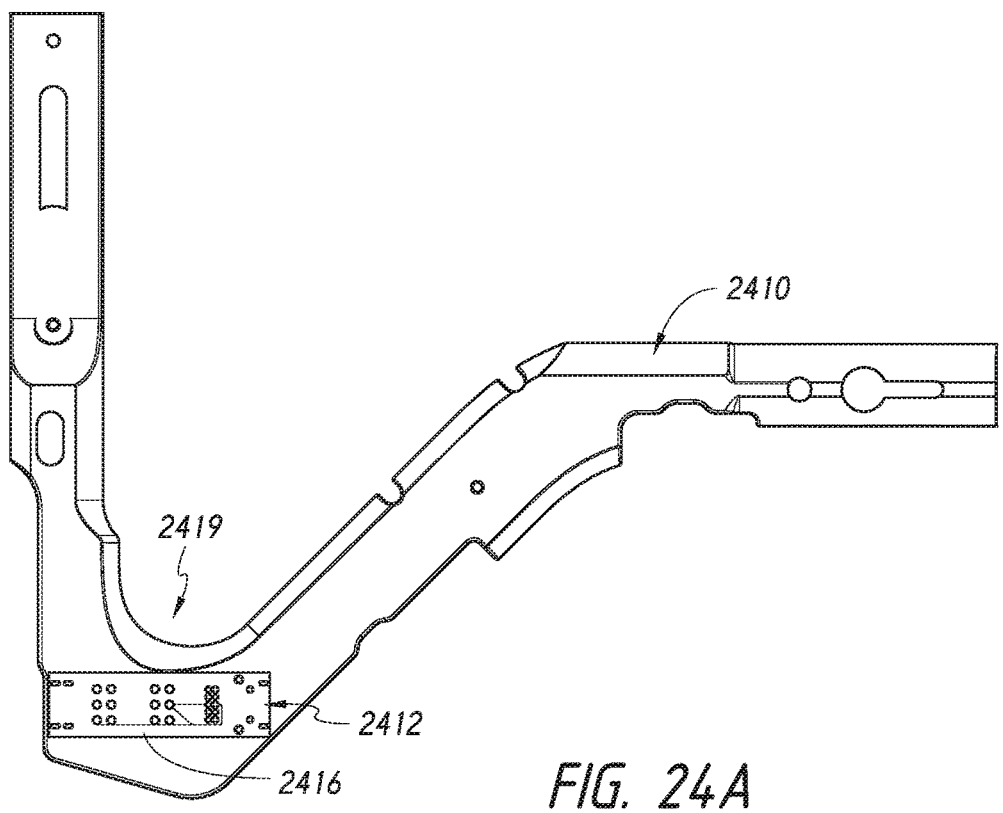
FIGS. 24A and 24B show an example of a load bearing structure of a mobility aid device, such as the mobility aid device of FIG. 13, including a load sensor in a first configuration and a second configuration, respectively.
Figure 24B:
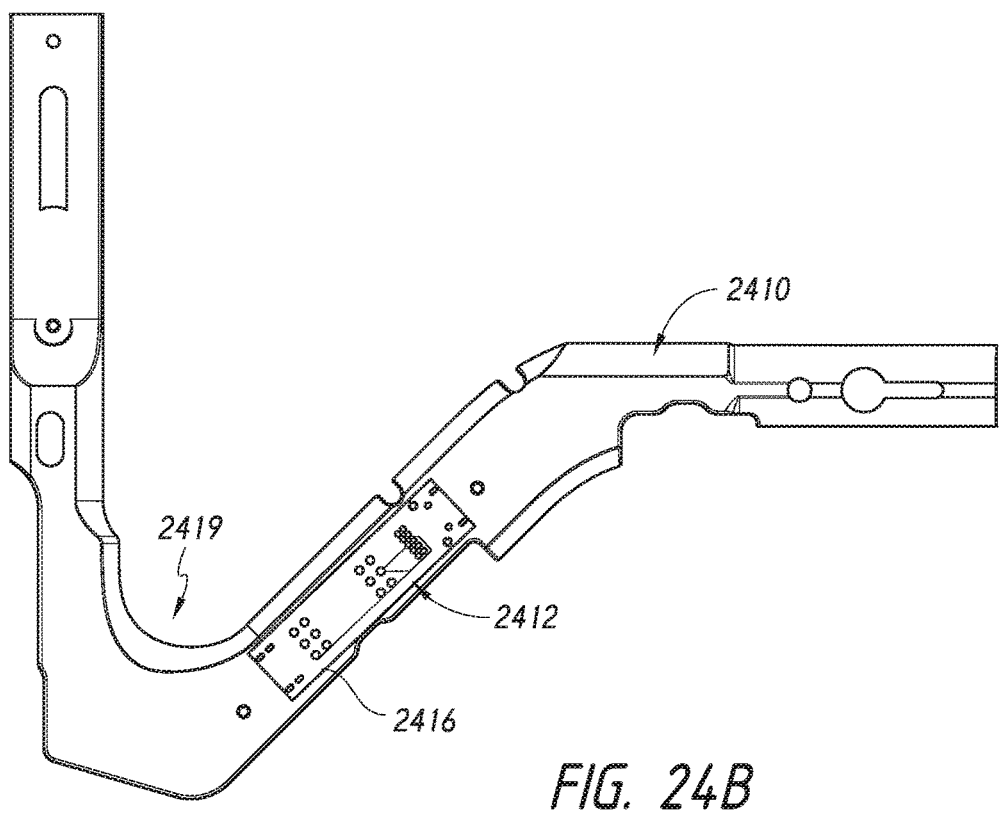

In other examples, load sensing may be achieved differently. For example, one or more strain gauges may be placed at various locations on the body of the smart mobility aid device (e.g., a rollator 101, a mobility aid device 700, a wheelchair, or the like), such as on a load-bearing component e.g., the structural core, also referred to as spine, of a handle, as shown in FIGS. 24A and 24B, of a cane a crutch or other mobility aid device. FIGS. 24A and 24B show an example of a spine 2410 suitable for use in a handle of a cane or crutch, for example, a handle 800 of a the mobility aid device 700. Other, similar structures could be used in an body portion support 730 of the mobility aid device 700, or a handle 210 of the rollator 101. The spine 2410, which may be the main load-bearing element of the handle that is responsible for supporting the load and offloading substantially all or much of the stress from the plastic and electronic components in the cane, may be manufactured from any suitable material for load bearing, such as metal (aluminum, steel, titanium, etc.), composite, or other. As such, the spine 2410 provides a support structure for coupling other components thereto including electronic components and/or the outer shroud of the handle, and all of the load applied to the handle by a user may be transmitted to the spine 2410, which transmits the load to the ground. Certain areas of the spine may experience higher stress, for example at the bend 2419 (see FIG. 24B) between the handle end and the vertical portion of the stem, and may thus provide suitable locations for load sensing. One or more strain gauges 2412, for example a strain gauge using a Wheatstone bridge (e.g., a full, half or quarter bridge) circuit, which may be provided on a circuit board 2416, may be operatively coupled to the structure (e.g., to the spine 2410) to sense deflection and thus strain experienced by structure. The strain gauge may be oriented in any suitable orientation, for example such that it is vertical as shown in FIG. 24A when the mobility aid device is in use, or such that it is at an angle to the vertical as shown in FIG. 24B when the mobility aid device is in use. While the examples in FIGS. 24A and 24B, as well as the discussion of the load sensor at the tip of the device illustrate two examples of locations where load sensing can be performed, load applied to the smart mobility device can be measured at virtually any other location along the load path of the device (e.g., the path along which the load travels from where it is applied by the user to where it is reacted by the ground).

As will be appreciated, enhanced functionality mobility aid devices may be provided in accordance with the examples of the present disclosure, which mobility aid devices provide one or more features to improve the safety, connectivity, and/or activity tracking of the user.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions.

For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A smart mobility device comprising:
   a frame configured to be rolled along a support surface responsive to force applied by a user, wherein the frame comprises:
      a plurality of wheels for rolling contact with the support surface, and
      a seat positioned above the plurality of wheels;
   a first display positioned on the frame to face the user's back when the user is seated on the seat;
   a handle configured to be gripped by the user for applying the force, wherein the first display is powered on responsive to the handle being gripped; and
   a second display arranged on the frame to be visible to the user when the user is seated on the seat, wherein both the first and second displays are visible to the user when gripping the device for walking.

2. The smart mobility device of claim 1, wherein the second display is located on the handle.

3. The smart mobility device of claim 1, wherein a grip sensor is positioned in the handle to detect the handle being gripped, and wherein the grip sensor is in communication with a processor configured to power up at least one of the first and second displays responsive to the handle being gripped.

4. The smart mobility device of claim 3, wherein the processor is communicatively coupled to one or more additional sensors operatively arranged on the frame to detect a change of condition.

5. The smart mobility device of claim 4, wherein the one or more additional sensors include at least one of a load cell, a strain gauge, a camera, a proximity sensor, and a touch sensor, configured to communicate sensor data to the processor, and wherein the processor is configured to generate a seated mode signal upon determination, based on the sensor data, that the user is seated on the seat.

6. The smart mobility device of claim 5, wherein the first display is configured to power down responsive to the seated mode signal.

7. The smart mobility device of claim 4, further comprising a light source configured to operate in one of a plurality of illumination modes based on the change of condition.

8. The smart mobility device of claim 7, wherein the light source is configured to operate at a first frequency or have a first illumination color when an emergency condition has been detected and to operate at a second frequency or have a second illumination color when no emergency condition has been detected.

9. The smart mobility device of claim 4, further comprising:
   a base; and
   a sensor near the base to detect a fall of the user, and wherein the processor is configured to generate an emergency transmission signal responsive to a detected fall.

10. The smart mobility device of claim 3, further comprising a sensor operatively associated with a wheel of the plurality of wheels to measure rotation of the respective wheel, and wherein the processor is configured to generate a gait measurement based on the measured rotation.

11. The smart mobility device of claim 3, further comprising a forward-facing camera arranged on the frame for detecting obstacles in a path of the smart mobility device, and wherein the processor is configured to generate a warning upon detection of an obstacle in the path of the smart mobility device.

12. The smart mobility device of claim 3, further comprising a rear-facing camera operatively positioned on the frame to include at least a portion of the user's body within a field of view of the rear-facing camera.

13. The smart mobility device of claim 12, wherein the rear-facing camera is positioned to include feet of the user within the field of view of the rear-facing camera, and wherein the processor is configured to generate: a stride length measurement based on a distance between the feet as detected by the rear-facing camera, a posture measurement based on image data captured by the rear-facing camera, or both.

14. The smart mobility device of claim 12, wherein the processor is configured to identify the user based on image data captured by the rear-facing camera and unlock the smart mobility device for use upon identification of an authorized user.

15. The smart mobility device of claim 14, wherein the processor is configured to automatically apply user-specific settings to the smart mobility device based on the authorized user.

16. The smart mobility device of claim 1, further comprising a sensor configured to measure biometric data associated with the user, and a memory for storing the biometric data onboard the smart mobility device.

17. The smart mobility device of claim 1, further comprising an electronic communication component configured to communicatively couple the smart mobility device to an external computing device, and wherein the electronic communication component automatically periodically transmits information about the user to the external computing device.

18. The smart mobility device of claim 1, wherein the frame is foldable such that the device can be provided into a storage configuration, which is more compact than a use configuration.

19. The smart mobility device of claim 1, wherein the frame includes left and right frame portions arranged symmetrically on opposite sides of the seat, and a backrest extending between the left and right frame portions, wherein the display is built into the backrest.

20. The smart mobility device of claim 1, further comprising a storage container removably coupled to the frame.

21. A smart mobility device comprising:
a frame configured to be rolled along a support surface responsive to force applied by a user, wherein the frame comprises:
a plurality of wheels for rolling contact with the support surface, and
a seat positioned above the plurality of wheels;
a display positioned on the frame to face the user's back when the user is seated on the seat;
a handle configured to be gripped by the user for applying the force, wherein the display is powered on responsive to the handle being gripped;
a plurality of microphones including a first microphone located elevationally closer to the handle than a second microphone located elevationally closer to the plurality of wheels;
a grip sensor is positioned in the handle to detect the handle being gripped;
a processor in communication with the grip sensor and configured to power up the display responsive to a determination that the handle is gripped; and wherein the frame comprises a base, and wherein a sensor is provided near the base to detect a fall of the user, and wherein the second microphone is automatically activated upon detection of the fall.

22. The smart mobility device of claim 21, further comprising a plurality of speakers including a first speaker located elevationally closer to the handle than a second speaker located elevationally closer to the plurality of wheels, and wherein the second speaker is automatically activated upon detection of the fall.

* * * * *